(12) United States Patent
Hong et al.

(10) Patent No.: US 11,179,440 B2
(45) Date of Patent: *Nov. 23, 2021

(54) PHARMACEUTICAL COMPOSITION CONTAINING FGF21 MUTANT FUSION PROTEIN AND METHOD FOR TREATING HEPATITIS, HEPATIC FIBROSIS, AND HEPATIC CIRRHOSIS

(71) Applicant: YUHAN CORPORATION, Seoul (KR)

(72) Inventors: Han Na Hong, Gunpo-si (KR); Jun Hwan Kim, Seoul (KR); Hyun Ho Choi, Suwon-si (KR); Dohoon Kim, Yongin-si (KR); Taewang Kim, Yongin-si (KR); Se Woong Oh, Suwon-si (KR); Moo Young Song, Suwon-si (KR); Jong Gyun Kim, Anyang-si (KR)

(73) Assignee: YUHAN CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/348,249

(22) PCT Filed: Nov. 10, 2017

(86) PCT No.: PCT/KR2017/012726
§ 371 (c)(1),
(2) Date: May 8, 2019

(87) PCT Pub. No.: WO2018/088838
PCT Pub. Date: May 17, 2018

(65) Prior Publication Data
US 2019/0314452 A1 Oct. 17, 2019

(30) Foreign Application Priority Data
Nov. 10, 2016 (KR) .......................... 10-2016-0149866

(51) Int. Cl.
A61K 38/18 (2006.01)
A61P 1/16 (2006.01)
A61K 38/17 (2006.01)
A61K 38/26 (2006.01)

(52) U.S. Cl.
CPC ...... *A61K 38/1825* (2013.01); *A61K 38/1703* (2013.01); *A61K 38/26* (2013.01); *A61P 1/16* (2018.01)

(58) Field of Classification Search
None
See application file for complete search history.

(56) References Cited

U.S. PATENT DOCUMENTS

| 5,851,800 | A | 12/1998 | Adamson et al. |
| 9,023,791 | B2* | 5/2015 | Boettcher ................. A61P 3/06 514/9.1 |
| 9,434,778 | B2* | 9/2016 | Morin ........................ A61P 1/00 |
| 9,441,030 | B2 | 9/2016 | Song et al. |
| 2012/0172298 | A1 | 7/2012 | Andersen et al. |
| 2012/0238496 | A1 | 9/2012 | Fan et al. |
| 2013/0129724 | A1 | 5/2013 | Boettcher et al. |
| 2014/0213512 | A1 | 7/2014 | Ellison et al. |
| 2014/0243503 | A1 | 8/2014 | Belouski et al. |

FOREIGN PATENT DOCUMENTS

| CN | 102558358 A | 7/2012 |
| CN | 105288592 A | 2/2016 |
| EA | 020843 B1 | 2/2015 |
| EP | 0 306 968 A2 | 3/1989 |
| EP | 2 548 570 A1 | 1/2013 |
| WO | 90/02175 A1 | 3/1990 |
| WO | 2003/011213 A2 | 2/2003 |
| WO | 03/059934 A2 | 7/2003 |
| WO | 2005/000892 A2 | 1/2005 |
| WO | 2005/091944 A2 | 10/2005 |
| WO | 2009/020802 A2 | 2/2009 |
| WO | 2010/065439 A1 | 6/2010 |
| WO | 2010/091122 A1 | 8/2010 |
| WO | 2010/129503 A1 | 11/2010 |
| WO | 2010/129600 A2 | 11/2010 |
| WO | 2010/142665 A1 | 12/2010 |
| WO | 2011/020319 A1 | 2/2011 |
| WO | 2011/089170 A1 | 7/2011 |

(Continued)

OTHER PUBLICATIONS

Justin D. Schumacher et al., "Regulation of Hepatic Stellate Cells and Fibrogenesis by Fibroblast Growth Factors", BioMed Research International, Jan. 2016 (Posted on ResearchGate), 21 pages, vol. 2016.

(Continued)

Primary Examiner — Christine J Saoud
(74) Attorney, Agent, or Firm — Sughrue Mion, PLLC

(57) ABSTRACT

A fusion protein containing a biologically active protein and an FGF21 mutant protein, a pharmaceutical composition containing the fusion protein, and their uses are disclosed. The fusion protein and the pharmaceutical composition are effective in treating a liver disease including hepatitis, hepatic fibrosis, and hepatic cirrhosis. The fusion protein has effects of inhibiting proliferation of inflammatory cells and fibroblasts, and thus can be effectively used for treating hepatitis, hepatic fibrosis, and hepatic cirrhosis.

21 Claims, 38 Drawing Sheets

Specification includes a Sequence Listing.

(56) References Cited

FOREIGN PATENT DOCUMENTS

| WO | 2012/010553 | A1 | 1/2012 |
|---|---|---|---|
| WO | 2012/066075 | A1 | 5/2012 |
| WO | 2012/170438 | A2 | 12/2012 |
| WO | 2013/033452 | A2 | 3/2013 |
| WO | 2013/131091 | A1 | 9/2013 |
| WO | 2013/188181 | A1 | 12/2013 |
| WO | 2014/130659 | A1 | 8/2014 |
| WO | 2015/038938 | A1 | 3/2015 |
| WO | 2017/074117 | A1 | 5/2017 |
| WO | 2017/074123 | A1 | 5/2017 |
| WO | 2018/166461 | A1 | 9/2018 |
| WO | 2018/194413 | A1 | 10/2018 |

OTHER PUBLICATIONS

H. Kahal et al., "Glucagon-like peptide-1 analogue, liraglutide, improves liver fibrosis markers in obese women with polycystic ovary syndrome and nonalcoholic fatty liver disease", Clinical Endocrinology, 2014, pp. 523-528, vol. 81.

Hecht et al., "Rationale-Based Engineering of a Potent Long-Acting FGF21 Analog for the Treatment of Type 2 Diabetes", PLOS ONE, Nov. 2012, vol. 7, Issue 11, e49345, pp. 1-14 (total 14 pages).

Alexei Kharitonenkov et al., "FGF-21 as a novel metabolic regulator", The Journal of Clinical Investigation, Jun. 2005, pp. 1627-1635, vol. 115, No. 6.

Jie Huang et al., "Development of a Novel Long-Acting Antidiabetic FGF21 Mimetic by Targeted Conjugation to a Scaffold Antibody", The Journal of Pharmacology and Experimental Therapeutics, Aug. 2013, pp. 270-280, vol. 346.

Bernard Thorens et al., "Cloning and Functional Expression of the Human Islet GLP-1 Receptor," Diabetes, Nov. 1993, pp. 1678-1682, vol. 42.

Mashkovsky M.D. Medicines, 16th ed., Revised, revised. M.: Novaya Volna, 2012, p. 8 (2 pages total).

Yakubke H.-D et al., Amino acids, peptides, proteins. -M.: Mir, 1985, p. 92-94 (5 pages total).

English Translation of Office Action dated Jan. 28, 2021 in Russian Application No. 2019117767.

* cited by examiner

PHARMACEUTICAL COMPOSITION CONTAINING FGF21 MUTANT FUSION PROTEIN AND METHOD FOR TREATING HEPATITIS, HEPATIC FIBROSIS, AND HEPATIC CIRRHOSIS

CROSS REFERENCE TO RELATED APPLICATIONS

This Application is a National Stage of International Application No. PCT/KR2017/012726 filed Nov. 10, 2017, claiming priority based on Korean Patent Application No. 10-2016-0149866 filed Nov. 10, 2016.

TECHNICAL FIELD

The present invention relates to a composition for preventing or treating hepatitis, hepatic fibrosis, and hepatic cirrhosis. Specifically, the present invention relates to a fusion protein comprising a biologically active protein and an FGF21 mutant protein; and a pharmaceutical composition containing the fusion protein which is effective for preventing or treating hepatitis, hepatic fibrosis, and hepatic cirrhosis.

BACKGROUND ART

There are various causes for liver diseases such as viral or bacterial infections, alcohol or toxic substances, excessive accumulation of fat or heavy metals, abnormal immune responses, etc. These causes may induce viral hepatitis, alcoholic liver disease, non-alcoholic fatty liver disease, toxic hepatitis, autoimmune liver disease, etc. Also, some liver diseases can progress to hepatic cirrhosis, hepatic fibrosis, and liver cancer through chronic progression.

An acute liver disease such as acute viral hepatitis or toxic hepatitis causes severe fatigue, poor appetite, jaundice, etc., and may unusually progress to acute hepatic failure which can lead to death if liver transplantation is not performed. On the other hand, chronic liver diseases which progress slowly such as chronic viral hepatitis and fatty liver disease are mostly asymptomatic, and patients may not feel significant inconvenience in daily life, however, hepatic fibrosis may be underway, and the chronic liver diseases may progress to hepatic cirrhosis and liver cancer while not aware. The prevalence of hepatic cirrhosis is estimated to be 0.5% in adults and about 1.0% in those aged 65 or higher in 2012 according to hepatic cirrhosis prevalence statistics in Korea. This is the result of a questionnaire surveyed based on the medical history of diagnoses at medical institutions, so the actual prevalence of hepatic cirrhosis is likely to be higher. The most common cause of hepatic cirrhosis in Korea is viral hepatitis, and the second most common cause is alcoholic liver disease.

If hepatic injury is repeated persistently by any cause, there are great risks for developing hepatic cirrhosis, fibrosis, and liver cancer regardless of the presence or absence of symptoms. Once hepatic cirrhosis has developed, it is difficult to restore the hardened liver to its original state even with treatment.

Glucagon-like peptide-1 (GLP-1) is an incretin hormone consisting of 31 amino acids, which is secreted by L cells in the intestinal tract when stimulated by food, etc. Its biological effects arise via intracellular signaling through the GLP-1 receptor, a G protein-coupled receptor which is expressed in target tissues such as β-cells in the pancreas, brain, etc. GLP-1 secreted in the blood has a very short half-life of less than 2 minutes, which is caused by a loss of activity due to the cleavage of amino acids at the N-terminus by the enzyme dipeptidyl peptidase-4 (DPP-4). Since GLP-1 stimulates the secretion of insulin in β-cells in the pancreas based on blood glucose level, it has a strong effect on lowering blood glucose without inducing hypoglycemia. Further, the administration of GLP-1 results in loss of body weight in various animal models and humans, which is known to be caused by reduced food intake due to its effect on appetite suppression. GLP-1 induces proliferation of β-cells and enhances the viability of β-cells by inhibiting cell death caused by glycolipid toxicity through GLP-1 receptor expressed in β-cells in the pancreas. Excessive secretion of glucagon increases blood glucose, which is known to be one of the causes of hyperglycemia in diabetics. In addition, it is known that GLP-1 acts on α-cells in the pancreas to inhibit fasting blood glucose elevation by inhibiting secretion of protein kinase A (PKA) protein-specific glucagon.

Exendin-4 is a clinically important GLP-1 receptor agonist. Exendin-4 is a polypeptide with 39 amino acid residues, and is normally produced in the salivary glands of the Gila Monster lizard. It is known that exendin-4 has amino acid sequence homology of 52% with GLP-1, and interacts with the GLP-1 receptor in mammals (Thorens et al. (1993) Diabetes 42:1678-1682). Exendin-4 has been shown to stimulate the secretion of insulin by insulin-producing cells in vitro, and the induction of insulin release by insulin-producing cells is stronger than GLP-1 under equimolar conditions. While exendin-4 strongly stimulates the secretion of insulin to decrease blood glucose levels in both rodents and humans with a duration of action longer than that of GLP-1, exendin-4 has exhibits antigenicity in mammals devoid of GLP-1 as it has unfamiliar epitopes in such animals.

The ability of GLP-1 and exendin-4 analogues (e.g., liraglutide and exenatide) to improve glucose control in humans has been clinically confirmed. It has been reported that GLP-1 increases β-cell mass through the inhibition of apoptosis and induced proliferation. Furthermore, it has been also reported that GLP-1 acts as an intestinal hormone inhibiting gastric acid secretion and gastric emptying while enhancing satiety signals, thereby reducing appetite. Such effects of GLP-1 can explain the weight loss observed when GLP-1 analogues are administered to patients with type 2 diabetes. In addition, GLP-1 exhibits cardioprotective effects following ischemia in rodents.

Various attempts have been made to develop long-acting GLP-1 analogues. Clinically confirmed long-acting GLP-1 analogues include dulaglutide (WO 2005/000892) and albiglutide (WO 2003/059934). Dulaglutide is an Fc-fused GLP-1 analogue, and albiglutide is an albumin-fused GLP-1 analogue, both of which have pharmacokinetic profiles allowing for once weekly administration. Both drugs have excellent effects on lowering blood glucose and reducing body weight with once weekly administration, and also provide greatly improved convenience in terms of treatment when compared to exenatide and liraglutide.

Meanwhile, fibroblast growth factor 21 (FGF21), synthesized in the liver, is a hormone known to play an important role in glucose and lipid homeostasis. FGF21 exhibits pharmacological actions in the liver, adipocytes, β cells of the pancreas, hypothalamus in the brain, and muscle tissues, where both an FGF21-specific receptor, i.e., FGF receptor, and β-klotho complex are expressed. It has been reported that in non-human primate and murine models of various diabetic and metabolic diseases, FGF21 can lower blood glucose levels in an insulin-independent manner, reduce body weight, and lower triglyceride and low-density lipoprotein (LDL) concentrations in the blood. In addition, it is known that FGF21 has insulin sensitivity-improving effects as well, and thus it has a high potential as a target of a novel anti-diabetic or an anti-obesity therapeutic agent (WO 2003/011213).

Accordingly, in order to develop a novel anti-diabetic drug based on FGF21, attempts have been made to improve its biological activity and in vivo stability by constructing FGF21 mutants based on the wild-type FGF21 sequence via substitution, insertion, and deletion of some amino acids (see WO2010/065439). However, as FGF21 has a very short half-life, it has proven problematic if used directly as a biotherapeutic agent (Kharitonenkov, A. et al., *Journal of Clinical Investigation* 115:1627-1635, 2005). The in vivo half-life of FGF21 is 1 to 2 hours in mice, and 2.5 to 3 hours in monkeys. Therefore, for FGF21 to be used in its current form as a therapeutic agent for diabetes, daily administration is required.

Various approaches have been reported in attempting to increase the in vivo half-life of FGF21 recombinant proteins. One such example is to link polyethylene glycol (PEG), i.e., a polymer material, to FGF21 to increase its molecular weight, thereby inhibiting renal excretion and increasing in vivo retention time (see WO2012/066075). Another approach attempts to improve the half-life by fusing it with a fatty acid, which binds to human albumin (see WO2012/010553). An additional example attempts to increase the half-life while maintaining pharmacological activity equivalent to that of wild-type FGF21 through the generation of an agonist antibody, which specifically binds to the human FGF receptor alone or as a complex with β-klotho (see WO2012/170438). In another example, the half-life was improved by preparing long-acting fusion proteins, in which an Fc region of IgG binds to an FGF21 molecule (see WO2013/188181).

Among the various technologies available to create long-acting drugs, Fc fusion technology is widely used because it has less of the disadvantages seen with other approaches, such as inducing an immune response or toxicity while increasing in vivo half-life. For the development of an Fc-fused FGF21 protein as a long-acting therapeutic drug, the following conditions should be satisfied.

First, the decrease of in vitro activity caused by fusion should be minimized. Both the N-terminus and C-terminus of FGF21 are involved in FGF21's activity. In this regard, it is known that the activities of FGF21 fusion proteins greatly vary depending on the location of the fusion. Accordingly, the activities of Fc-fused FGF21 fusion proteins, in which mutations are introduced into FGF21, may be altered depending on the presence/absence or location of the fusion. Second, a pharmacokinetic profile enabling administration at an interval of once per week in humans should be realized by the increase of in vivo half-life by the fusion. Third, considering that immunogenicity may be expected in most patients after administration of biopharmaceuticals, the immunogenicity risk due to a fusion linker or mutation should be minimized. Fourth, there should be no stability issues arising from the position of the fusion or the introduction of the mutation. Fifth, since undesired immune responses may occur depending on the isotypes of fused immunoglobulin, a solution to prevent such responses is necessary.

An attempt to develop a long-acting fusion protein by linking the Fc region of an immunoglobulin G (IgG) to an FGF21 molecule has already been reported (see WO 2013/188181). In the case of one Fc-FGF21 structure, where the Fc is fused to the N-terminus of the wild-type FGF21, while there is no distinct difference in in vitro activity as compared to that of the wild-type FGF21, the half-life is known to be very short due to in vivo degradation of the protein. To address this issue, there has been an attempt to improve the in vivo half-life by introducing several mutations at specific site locations of FGF21 to resist protein degradation. However, immunogenicity risk may increase with the introduction of multiple mutations. In contrast, in the case of an FGF21-Fc structure, where the Fc is fused to the C-terminus of the FGF21 molecule, it is known that there is a significant decrease in activity caused by fusion at this site when compared to the Fc-FGF21 structure.

Combined administration of GLP-1 and FGF21 may have a synergistic effect as compared with single administration depending on the action mechanisms and target tissues in the body, and potentially outstanding anti-diabetic efficacy and additional advantages are expected. The effects of combined administration of GLP-1 and FGF21 or a GLP-1/FGF21 fusion protein have been already investigated and reported (see WO 2010/142665 and WO 2011/020319).

Various problems must be solved in order to develop a fusion protein comprising GLP-1 and FGF21. Since wild-type GLP-1 and wild-type FGF21 have a very short in vivo half-life, they are required to be administered at least once daily, even if developed as therapeutic agents. Accordingly, long-acting technologies such as an Fc fusion are required in order to develop a long-acting fusion protein to improve convenience for patients. In a dual function drug for the two targets of GLP-1 and FGF21, the introduction of mutation(s) is essential to maintain the activities and in vivo stability of the drug, and problems associated with changes in activity, structure or stability caused by each mutation should be addressed. Medicinal effects for the two targets of GLP-1 and FGF21 should be well-balanced, and drug designs in consideration of in vitro activities, pharmacokinetic profiles, pharmacological efficacy in animal models, and even clinical evaluation of efficacy in humans are required for this purpose. A fusion protein has a structure that cannot exist in a human body, and is structurally complex as compared with a fusion protein for a single target. In addition, since mutation or linker engineering is required to balance the two targets, the possibility of forming aggregate complexes may increase, and further protein engineering to prevent this may be required. Furthermore, potential immunogenicity may increase due to novel mutation sequences or complex structures, which should be addressed or avoided.

The present inventors have made efforts to solve the above problems, and as a result, have developed a fusion protein effective for treating hepatitis, hepatic fibrosis, and hepatic cirrhosis, and completed the present invention.

DISCLOSURE

Technical Problem

An object of the present invention is to provide a pharmaceutical composition for preventing or treating hepatitis, hepatic fibrosis, and hepatic cirrhosis.

Technical Solution

In accordance with one object of the present invention, there is provided a pharmaceutical composition for preventing or treating hepatitis, hepatic fibrosis, and hepatic cirrhosis containing, as an effective component, a fusion protein comprising a fibroblast growth factor 21 (FGF21) mutant protein; and an Fc region of an immunoglobulin, wherein the FGF21 mutant protein comprises at least one mutation selected from the group consisting of the following mutations (1) to (7):

(1) a substitution of amino acids at positions 98 to 101 from the N-terminus of a wild-type FGF21 protein with an amino acid sequence of EIRP (SEQ ID NO: 68);

(2) a substitution of amino acids at positions 170 to 174 from the N-terminus of a wild-type FGF21 protein with an amino acid sequence of TGLEAV (SEQ ID NO: 69);

(3) a substitution of amino acids at positions 170 to 174 from the N-terminus of a wild-type FGF21 protein with an amino acid sequence of TGLEAN (SEQ ID NO: 70);

(4) a substitution of an amino acid at position 170 from the N-terminus of a wild-type FGF21 protein with an amino acid N;

(5) a substitution of an amino acid at position 174 from the N-terminus of a wild-type FGF21 protein with an amino acid N;

(6) a substitution of an amino acid at position 180 from the N-terminus of a wild-type FGF21 protein with an amino acid E, along with one or more mutations (1) to (5) above; and (7) a mutation of 1 to 10 amino acids for reducing immunogenicity of a wild-type FGF21 protein.

Further, in accordance with another object of the present invention, there is provided a pharmaceutical composition for preventing or treating hepatitis, hepatic fibrosis, and hepatic cirrhosis containing, as an effective component, a fusion protein comprising a fibroblast growth factor 21 (FGF21) mutant protein; a biologically active protein, or a mutant or fragment thereof; and an Fc region of an immunoglobulin, wherein the FGF21 mutant protein comprises at least one mutation selected from the group consisting of the following mutations (1) to (7):

(1) a substitution of amino acids at positions 98 to 101 from the N-terminus of a wild-type FGF21 protein with an amino acid sequence of EIRP (SEQ ID NO: 68);

(2) a substitution of amino acids at positions 170 to 174 from the N-terminus of a wild-type FGF21 protein with an amino acid sequence of TGLEAV (SEQ ID NO: 69);

(3) a substitution of amino acids at positions 170 to 174 from the N-terminus of a wild-type FGF21 protein with an amino acid sequence of TGLEAN (SEQ ID NO: 70);

(4) a substitution of an amino acid at position 170 from the N-terminus of a wild-type FGF21 protein with an amino acid N;

(5) a substitution of an amino acid at position 174 from the N-terminus of a wild-type FGF21 protein with an amino acid N;

(6) a substitution of an amino acid at position 180 from the N-terminus of a wild-type FGF21 protein with an amino acid E, along with one or more mutations (1) to (5) above; and (7) a mutation of 1 to 10 amino acids for reducing immunogenicity of a wild-type FGF21 protein.

Further, in accordance with another object of the present invention, there is provided a use of a pharmaceutical composition of the present invention for preventing or treating hepatitis, hepatic fibrosis, and hepatic cirrhosis Further, in accordance with another object of the present invention, there is provided a use of a pharmaceutical composition of the present invention for preparing a composition for preventing or treating hepatitis, hepatic fibrosis and hepatic cirrhosis.

Further, in accordance with another object of the present invention, there is provided a method for preventing or treating hepatitis, hepatic fibrosis, and hepatic cirrhosis, which comprises the step of administering the fusion protein of the present invention to a subject.

Advantageous Effects

A pharmaceutical composition of the present invention for preventing or treating hepatitis, hepatic fibrosis, and hepatic cirrhosis containing, as an effective component, a fusion protein comprising a fibroblast growth factor 21 (FGF21) mutant protein; and an Fc region of an immunoglobulin has the effect of inhibiting the proliferation of inflammatory cells and fibroblasts, and thus can be effectively used as a composition for preventing or treating hepatitis, hepatic fibrosis, and hepatic cirrhosis.

BEST MODE

Figure 1A:
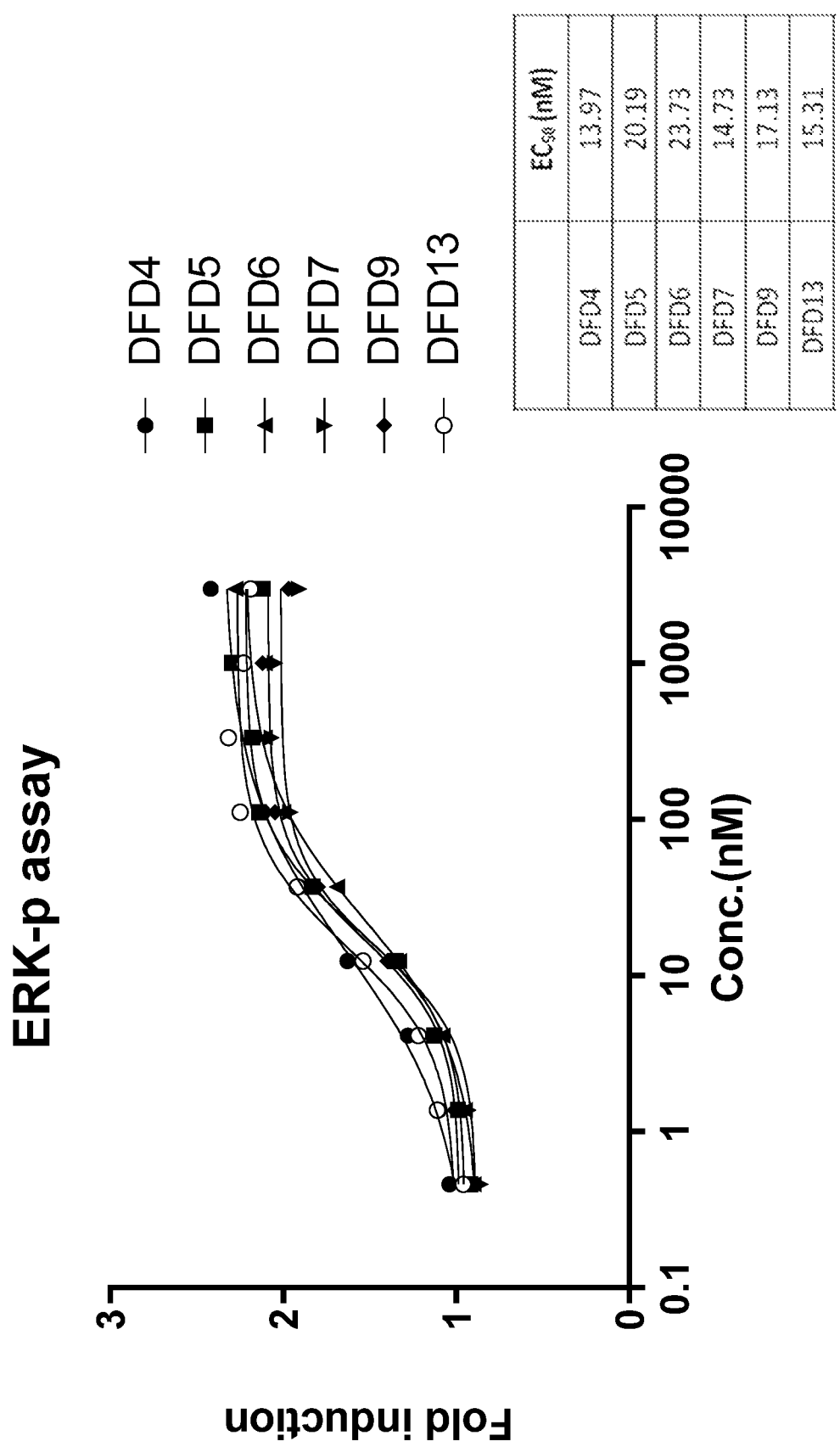
FIG. 1A is a graph showing the in vitro activities of DFD4, DFD5, DFD6, DFD7, DFD9, and DFD13, as fusion proteins including FGF21 mutant proteins (hereinafter, "FGF21 mutant fusion protein"), using a HEK293 cell line in which human β-klotho is overexpressed. No FGF21 mutant fusion proteins exhibited a significant decrease in activity due to the introduction of a mutation.

Hereinafter, the present invention is explained in detail.

A fusion protein contained as an active component in a composition for preventing or treating hepatitis, hepatic fibrosis, and hepatic cirrhosis according to the present invention comprises a fibroblast growth factor 21 (FGF21) mutant protein; and an Fc region of an immunoglobulin, wherein the FGF21 mutant protein comprises at least one mutation selected from the group consisting of the following mutations (1) to (7):

(1) a substitution of amino acids at positions 98 to 101 from the N-terminus of a wild-type FGF21 protein with an amino acid sequence of EIRP (SEQ ID NO: 68);

(2) a substitution of amino acids at positions 170 to 174 from the N-terminus of a wild-type FGF21 protein with an amino acid sequence of TGLEAV (SEQ ID NO: 69);

(3) a substitution of amino acids at positions 170 to 174 from the N-terminus of a wild-type FGF21 protein with an amino acid sequence of TGLEAN (SEQ ID NO: 70);

(4) a substitution of an amino acid at position 170 from the N-terminus of a wild-type FGF21 protein with an amino acid N;

(5) a substitution of an amino acid at position 174 from the N-terminus of a wild-type FGF21 protein with an amino acid N;

(6) a substitution of an amino acid at position 180 from the N-terminus of a wild-type FGF21 protein with an amino acid E, along with one or more mutations (1) to (5) above; and (7) a mutation of 1 to 10 amino acids for reducing immunogenicity of a wild-type FGF21 protein.

The fusion protein may further comprise a biologically active protein, or a mutant or fragment thereof.

Specifically, the fusion protein contained as an active component in a composition for preventing or treating hepatitis, hepatic fibrosis, and hepatic cirrhosis according to the present invention comprises a fibroblast growth factor 21 (FGF21) mutant protein; a biologically active protein, or a mutant or fragment thereof; and an Fc region of an immunoglobulin, wherein the FGF21 mutant protein comprises at least one mutation selected from the group consisting of the following mutations (1) to (7):

(1) a substitution of amino acids at positions 98 to 101 from the N-terminus of a wild-type FGF21 protein with an amino acid sequence of EIRP (SEQ ID NO: 68);

(2) a substitution of amino acids at positions 170 to 174 from the N-terminus of a wild-type FGF21 protein with an amino acid sequence of TGLEAV (SEQ ID NO: 69);

(3) a substitution of amino acids at positions 170 to 174 from the N-terminus of a wild-type FGF21 protein with an amino acid sequence of TGLEAN (SEQ ID NO: 70);

(4) a substitution of an amino acid at position 170 from the N-terminus of a wild-type FGF21 protein with an amino acid N;

(5) a substitution of an amino acid at position 174 from the N-terminus of a wild-type FGF21 protein with an amino acid N;

(6) a substitution of an amino acid at position 180 from the N-terminus of a wild-type FGF21 protein with an amino acid E, along with one or more mutations (1) to (5) above; and (7) a mutation of 1 to 10 amino acids for reducing immunogenicity of a wild-type FGF21 protein.

The wild-type FGF21 protein is a hormone known to play an important role in glucose and fat homeostasis, may be derived from a mammal such as a human, a mouse, a pig, or a monkey, etc., preferably from human. More preferably, the wild-type FGF21 protein may be the wild-type human FGF21 protein having an amino acid sequence represented by SEQ ID NO: 1.

The mutation included in the FGF21 mutant proteins may be, preferably, any one of the mutations of EIRP (SEQ ID NO: 68), TGLEAV (SEQ ID NO: 69), TGLEAN (SEQ ID NO: 70), G170N and G174N; a combination of any one of the mutations of TGLEAV (SEQ ID NO: 69), TGLEAN (SEQ ID NO: 70), G170N and G174N and the mutation of EIRP (SEQ ID NO: 68); a combination of any one of the mutations of EIRP (SEQ ID NO: 68), TGLEAV (SEQ ID NO: 69), TGLEAN (SEQ ID NO: 70), G170N and G174N and the mutation of A180E; or a combination of any one of the mutations of TGLEAV (SEQ ID NO: 69), TGLEAN (SEQ ID NO: 70), G170N and G174N, the mutation of EIRP (SEQ ID NO: 68) and the mutation of A180E. Furthermore, the FGF21 mutant proteins may have a conformation, in which 1 to 10 amino acids at the N-terminus or C-terminus is (are) deleted as compared to the wild-type FGF21 protein. More preferably, the FGF21 mutant proteins may include an amino acid sequence represented by any one of SEQ ID NO:6 to 23. Still more preferably, the FGF21 mutant proteins may include an amino acid sequence represented by any one of SEQ ID NO: 6 to 23 and further have a conformation, in which 1 to 10 amino acids at the N-terminus or C-terminus is (are) deleted as compared to the wild-type FGF21 protein.

In the fusion protein, asparagine (N) residue introduced by a mutation of the FGF21 mutant protein may be glycosylated.

The biologically active protein may be one selected from the group consisting of insulin, C-peptide, leptin, glucagon, gastrin, gastric inhibitory polypeptide (GIP), amylin, calcitonin, cholecystokinin, peptide YY, neuropeptide Y, bone morphogenetic protein-6 (BMP-6), bone morphogenetic protein-9 (BMP-9), oxyntomodulin, oxytocin, glucagon-like peptide-1 (GLP-1), glucagon-like peptide-2 (GLP-2), irisin, fibronectin type III domain-containing protein 5 (FNDC5), apelin, adiponectin, C1q and tumor necrosis factor related protein (CTRP family), resistin, visfatin, omentin, retinol binding protein-4 (RBP-4), glicentin, angiopoietin, interleukin-22 (IL-22), exendin-4 and growth hormone. Preferably, the biologically active protein may be one selected from GLP-1, a mutant thereof and exendin-4. Specifically, the fusion protein can simultaneously exhibit the effect of GLP-1 and the effect of FGF21 protein.

As used herein, the term "insulin" refers to a protein synthesized and secreted by the beta cells of the pancreas, which is a hormone that plays a role in maintaining a constant glucose level in the blood. Insulin is secreted when the blood glucose level is high, which allows the glucose in the blood to enter into cells to be stored in the form of glycogen, and inhibits glucose production in hepatocyte. It also helps glucose oxidization and conversion to fatty acids in adipose tissues. In muscles, it promotes the absorption of amino acids to synthesize proteins. Epinephrine and glucagon act as antagonists of insulin by increasing blood glucose level.

As used herein, the term "C-peptide" refers to a peptide that links the A and B chains of proinsulin. The C-peptide is secreted along with insulin by the secretory granules of pancreatic cells, but is not degraded in the blood, so it is used as an index of the insulin-secreting function of the pancreas.

As used herein, the term "leptin" refers to a hormone that maintains body fat secreted by adipose tissues at a constant level. The leptin secreted by adipose tissues acts on the brain to suppress appetite and activate metabolism in the body, thereby reducing body weight.

As used herein, the term "glucagon" refers to a protein synthesized and secreted by pancreas, which is a hormone secreted in response to a lowered blood sugar level, to play the role of increasing the blood sugar level. The glucacon consists of 29 amino acid residues, being secreted by α cells of Langerhans islets.

As used herein, the term "gastrin" refers to a hormone secreted at the distal end of the stomach, which induces gastric acid secretion and production of pancreatic fluid, and promotes movement of the stomach, small intestine, and large intestine.

As used herein, the term "gastrin-inhibiting polypeptide" refers to a linear polypeptide that inhibits all gastric secretions.

As used herein, the term "amylin" refers to a hormone synthesized and secreted by the beta cells of pancreas, which regulates glucose metabolism like insulin.

As used herein, the term "calcitonin" refers to a thyroid hormone that regulates the calcium level in the blood. The calcitonin is a polypeptide consisting of 32 amino acids, being secreted by thyroid C cells.

As used herein, the term "cholecystokinin" refers to a hormone consisting of 33 amino acids produced by the I cells of duodenum and jejunum. The cholecystokinin shows the action of accelerating the contraction of spleen and promoting the secretion of pancreatic enzyme, and inhibits the secretion of gastric acid.

As used herein, the term "peptide YY" is an abbreviation for peptide tyrosine tyrosine, which refers to a polypeptide consisting of 36 amino acids, being secreted by the cells of the large intestine and ileum in response to a diet.

As used herein, the term "neuropeptide Y" refers to a biologically active peptide consisting of 36 amino acids whose carboxy terminus is aminated. The neuropeptide Y is widely distributed in the central and peripheral nervous systems of vertebrate animals, and regulates blood pressure in sympathetic nervous system, and is involved in the endocrine or autonomic nervous control, feeding behavior, memory, and circadian rhythm in vertebrate animal's central nervous system.

As used herein, the term "osteogenic protein 6", also called BMP-6, refers to a protein directly involved in bone formation.

As used herein, the term "osteogenic protein 9", also called BMP-9, refers to a protein directly involved in bone formation.

As used herein, the term "oxytomodulin" refers to a polypeptide consisting of 37 amino acids, being secreted by the mural cells of the mucosa. The oxytomodulin has a strong appetite-suppressing effect.

As used herein, the term "oxytocin" refers to a hormone consisting of 9 amino acids, which promotes uterine contraction during delivery and helps secretion of milk during breast feeding.

As used herein, the term "GLP-1" refers to an incretin hormone consisting of 31 amino acids, being secreted in the intestinal L cells stimulated by food or the like. For example, the GLP-1 protein may be represented by the amino acid sequence of SEQ ID NO: 42.

The mutant of GLP-1 may be represented, for example, by an amino acid sequence of any one of SEQ ID NO: 43 to 46.

As used herein, the term "irisin" refers to a hormone secreted by muscles during exercise and reaching adipocytes through blood stream to decompose fats, such as conversion of white adipocytes to brown adipocytes. The irisin consists of 112 amino acids, which is a truncated fragment of a membrane protein called FNDC5.

As used herein, the term "FNDC5" is an abbreviation for Fibronectin type III domain-containing protein 5, and refers to a precursor substance of irisin.

As used herein, the term "apelin" refers to a peptide encoded by the APLN gene. The apelin is synthesized and secreted by adipose tissues and has the same function as insulin.

As used herein, the term "adiponectin" refers to a protein secreted by adipocytes, which improves insulin resistance.

As used herein, the term "CTRP family" refers to C1q and tumor necrosis factor-related protein, which is one of the adipokine family and mainly acts on liver and muscle tissues to regulate glucose and lipid metabolisms, etc.

As used herein, the term "resistin" refers to a recently discovered adipokine secreted by adipocytes, which is a protein consisting of 108 amino acids and known as an agent increased during fat differentiation and capable of inhibiting the differentiation of adipocytes.

As used herein, the term "visfatin" refers to one of the adipokines produced and secreted by adipose tissues, which is a protein of 52 kDa.

As used herein, the term "omentin" refers to one of the adipokines produced and secreted by adipose tissues, which is a protein having an anti-inflammatory action.

As used herein, the term "retinol binding protein-4" refers to a protein secreted by adipocytes, which carries vitamin A that improves insulin resistance.

As used herein, the term "glycetin" refers to a major enteroglucagon in the digestive tract, which consists of 69 amino acids including all 29 amino acids of glucagon between amino acids at positions 33-66.

As used herein, the term "angiopoietin", also called ANG, refers to a protein that acts during the growth of blood vessels or vascular endothelial cells or during the wound healing in the body.

As used herein, the term "IL-22", also called IL-TIF, refers to a protein encoded by the IL-22 gene. The IL-22 is secreted by natural killer cells or T cells activated in response to bacterial antigens of the epithelial cells.

As used herein, the term "Fc region," "Fc fragment," or "Fc" refers to a protein, which includes a heavy chain constant region 1 (CH1), a heavy chain constant region 2 (CH2) and a heavy chain constant region 3 (CH3) of an immunoglobulin, but does not include variable regions of the heavy and light chains and a light chain constant region 1 (CL1) of an immunoglobulin. Additionally, as used herein, the term "Fc region mutant" refers to one prepared by substituting part of amino acid(s) of an Fc region or by combining Fc regions of different types.

The Fc region of immunoglobulin may be an entire Fc region constituting an antibody, a fragment thereof, or an Fc region mutant. Additionally, the Fc region includes a molecule in the form of a monomer or multimer, and may further include a hinge region of the heavy chain constant region. The Fc region mutant may be modified to prevent cleavage at the hinge region. Furthermore, the hinge sequence of the Fc may have a substitution in some amino acid sequences to reduce antibody-dependent cell-mediated cytotoxicity (ADCC) or complement-dependent cytotoxicity (CDC). In addition, part of the amino acid sequence of the Fc hinge sequence may be substituted to inhibit the rearrangement of the Fab region. A lysine (K) at the C-terminus of the Fc may be removed.

Preferably, the Fc region of immunoglobulin may be any one of IgG1, IgG2, IgG3, IgG4 and IgD Fc regions; or a hybrid Fc, which is a combination thereof. Further, the hybrid Fc may include an IgG4 region and an IgD region. Further, the hybrid Fc region may include part of the hinge sequence and CH2 of an IgD Fc, and CH2 and CH3 sequences of IgG4 Fc.

In addition, the Fc fragment of the present invention may be in the form of wild-type glycosylated chain, more glycosylated chain than the wild-type, less glycosylated chain than the wild-type, or deglycosylated chain. The increase, decrease, or removal of glycosylated chain may be performed by a conventional method known in the art, such as a chemical method, an enzymatic method, and a genetic engineering method using microorganisms.

Preferably, the immunoglobulin Fc region may be represented by an amino acid sequence selected from SEQ ID NO: 24 to 26, 47 and 48.

The fusion protein may include a biologically active protein, an Fc region of an immunoglobulin and an FGF21 mutant protein, linked in this order from the N-terminus to the C-terminus. Further, the fusion protein may include an FGF21 mutant protein, an Fc region of an immunoglobulin and a biologically active protein, linked in this order from the N-terminus to the C-terminus. Preferably, the fusion protein may include a biologically active protein, an Fc region of an immunoglobulin and an FGF21 mutant protein, linked in this order from the N-terminus to the C-terminus.

Furthermore, the fusion protein may include a GLP-1 mutant protein, an Fc region of an immunoglobulin and an FGF21 mutant protein, linked in this order from the N-terminus to the C-terminus. Further, the fusion protein may include an FGF21 mutant protein, an Fc region of an immunoglobulin and a GLP-1 mutant protein, linked in this order from the N-terminus to the C-terminus. Preferably, the fusion protein may include a GLP-1 mutant protein, an Fc region of an immunoglobulin and an FGF21 mutant protein, linked in this order from the N-terminus to the C-terminus.

Additionally, the fusion protein may further include a linker.

The fusion protein may be in the form, in which the FGF21 mutant protein is directly connected to the N-terminus or C-terminus of the immunoglobulin Fc region, or the FGF21 mutant protein is connected to the immunoglobulin Fc region via a linker.

In such case, the linker may be connected to the N-terminus, C-terminus, or a free radical of the Fc fragment, and also, may be connected to the N-terminus, C-terminus, or a free radical of the FGF21 mutant protein. When the linker is a peptide linker, the connection may occur in any region. For example, the linker may be connected to the C-terminus of the immunoglobulin Fc region and the N-terminus of the FGF21 mutant protein to form a fusion protein of the immunoglobulin Fc region and the FGF21 mutant protein.

Furthermore, the fusion protein of the present invention may be in the form, in which a biologically active protein is linked to the N-terminus of the Fc region of immunoglobulin of the fusion protein.

When the linker and Fc are separately expressed and then connected, the linker may be a crosslinking agent known in the art. Examples of the crosslinking agent may include 1,1-bis(diazoacetyl)-2-phenylethane, glutaraldehyde, imidoesters including N-hydroxysuccinimide ester such as 4-azidosalicylic acid and disuccinimidyl esters such as 3,3'-dithiobis(succinimidylpropionate), and bifunctional maleimides such as bis-N-maleimido-1,8-octane, but are not limited thereto.

Further, the linker may be a peptide. Preferably, the linker may be a peptide consisting of 10 to 30 amino acid residues.

Furthermore, alanine may additionally be attached to the end of linker. Preferably, the linker may be a peptide having an amino acid sequence represented by any one of SEQ ID NO: 2 to 5.

The fusion protein may be in a form in which a dimer or multimer of FGF21 mutant proteins, in which one or more FGF21 mutant proteins linked together, is connected to an immunoglobulin Fc region. Additionally, the fusion protein may be in a form of a dimer or multimer in which two or more immunoglobulin Fc regions are linked, wherein the immunoglobulin Fc regions have the FGF21 mutant protein connected thereto.

Further, specifically, the fusion protein may be represented by an amino acid sequence of any one of SEQ ID NO: 36 to 39. More specifically, it may be represented by the amino acid sequence of SEQ ID NO: 36, 37 or 39.

Additionally, the fusion protein may be a peptide which preferably has an amino acid sequence represented by any one of SEQ ID NO: 58 to 67. More preferably, the fusion protein may be a peptide which has an amino acid sequence represented by SEQ ID NO: 65, 66 or 67.

The FGF21 mutant protein may further include a mutation of 1 to 10 amino acids for reducing immunogenicity of the wild-type FGF21 protein. The immunogenicity may be predicted by a conventional method known in the art. For example, the potential immunogenicity of a protein may be screened by using, e.g., ITOPE™ and TCED™ methods.

Further, the mutation for minimizing the immunogenicity may be designed by a conventional method known in the art. For example, when immunogenicity is observed by performing an EPISCREEN™ analysis to evaluate potential immunogenicity, the amino acid sequences inducing the immunogenicity may be identified through T-cell epitope mapping, and the mutants with minimized immunogenicity may be designed via in silico prediction.

The fusion protein can be used for preventing or treating hepatitis, hepatic fibrosis, and hepatic cirrhosis.

Specifically, the hepatitis may be acute viral hepatitis, chronic hepatitis, alcoholic hepatitis, autoimmune hepatitis, fulminant hepatitis, or non-alcoholic steatohepatitis (NASH). Specifically, the hepatic cirrhosis may be alcoholic hepatic cirrhosis, or primary biliary cirrhosis.

Further, the pharmaceutical composition may further include a pharmaceutical carrier. The pharmaceutical carrier may be any carrier as long as it is a non-toxic material suitable for delivering antibodies to patients. For example, distilled water, alcohol, fats, waxes and inactive solids may be included as a carrier. Pharmaceutically acceptable adjuvants (buffering agents, dispersants) may also be included in the pharmaceutical composition. In these formulations, the concentration of the fusion protein may vary greatly.

Specifically, the pharmaceutical composition may contain a formulation material for altering, maintaining, or conserving the pH, osmolarity, viscosity, transparency, color, isotonicity, odor, sterility, stability, dissolution or release rate, adsorption, or permeability of the composition. For appropriate formuation, it may further comprise amino acids (e.g., glycine, glutamine, asparagine, arginine or lysine), antimicroorganism agents, anti-oxidants (e.g., ascorbic acid, sodium sulfite or sodium bisulfate), buffering agents (e.g., borate, bicarbonates, Tris-HCl, citrate, phosphate or other organic acids), bulking agents (e.g., mannitol or glycine), chelating agents (e.g., ethyelenediaminetetraacetic acid (EDTA)), complexing agents (e.g., caffeine, polyvinylpyrrolidione, β-cyclodextrin or hydroxypropyl-β-cyclodextrin), fillers, monosaccharides, disaccharides and other carbohydrates (e.g., glucose, mannose or dextrin), proteins (e.g., serum albumin, gelatin or immunoglobulin), coloring agents, flavoring agents, diluents, emulsifiers, hydrophilic polymers (e.g., polyvinylpyrrolidione), low molecular weight polypeptides, salt-forming counterions (e.g., sodium), preservatives (e.g., benzalkonium chloride, benzoic acid, salicylic acid, thimerosal, phenethyl alcohol, methylparaben, propylparaben, chlorhexidine, sorbic acid or hydrogen peroxide), solvents (e.g., glycerin, propylene glycol or polyethylene glycol), sugar alcohols (e.g., mannitol or sorbitol), suspending agents, surfactants or humectants (e.g., pluronics; PEG; sorbitan ester; polysorbate, e.g., polysorbate 20 or polysorbate 80; triton; tromethamine; lecithin; cholesterol or tyloxapol), stability improvers (e.g., sucrose or sorbitol), growth improvers (e.g., alkali metal halides, preferably, sodium chloride or potassium chloride; or mannitol, sorbitol), delivery vehicles, diluents, excipients and/or pharmaceutical adjuvants, but is not limited thereto.

In addition, the present invention also provides a method for preventing or treating hepatitis, hepatic fibrosis, and hepatic cirrhosis, which comprises administering the inventive pharmaceutical composition to a subject in need of treatment. Such method may comprise administering an effective amount of the fusion protein of the present invention to a mammal having a symptom of hepatitis such as acute viral hepatitis, chronic hepatitis, alcoholic hepatitis, autoimmune hepatitis, fulminant hepatitis, non-alcoholic steatohepatitis (NASH). It may also comprise administering an effective amount of a fusion protein of the present invention to a mammal having a symptom of hepatic cirrhosis, e.g., alcoholic hepatic cirrhosis, primary biliary cirrhosis, and hepatic fibrosis.

The pharmaceutical composition of the present invention may be administered via any route. The composition of the present invention may be provided to an animal directly (e.g., topically, by administering into tissue areas by injection, transplantation, or by topical administration) or systemically (e.g., by oral- or parenteral administration) via any appropriate means. When the composition of the present invention is parenterally provided via intravenous-, subcutaneous-, ophthalmic-, intraperitoneal-, intramuscular-, oral-, rectal-, intraorbital-, intracerebral-, intracranial-, intraspinal-, intraventricular-, intrathecal-, intracistenal-, intracapsular-, intranasal-, or aerosol administration, the composition is preferably aqueous or may include a portion of a biologically applicable body liquid suspension or solution. Accordingly, the carrier or vehicle may be added to the composition and be delivered to a patient since it is biologically applicable. Therefore, a biologically-appropriate saline solution may generally be included as a carrier like a body fluid for formulations.

Further, the administration frequency may vary depending on the pharmacokinetic parameters of the fusion protein in the formulations to be used. Typically, physicians would administer the composition until an administration dose to achieve a desired effect is reached. Accordingly, the composition may be administered as a unit dose, at least two doses with time intervals (may or may not contain the same amount of a target fusion protein) or administered by a continuous injection via a transplantation device or catheter. The precision of addition of an appropriate administration dose may be routinely performed by those skilled in the art, and corresponds to the scope of work being routinely performed by them.

Additionally, the preferable unit dose of the fusion protein in humans may be in a range from 0.01 µg to 100 mg/kg of body weight, and more preferably from 1 µg to 10 mg/kg of body weight. Although this is the optimal amount, the unit dose may vary depending on the disease to be treated or the presence/absence of adverse effects. Nevertheless, the optimal administration dose may be determined by performing a conventional experiment. The administration of the fusion protein may be performed by a periodic bolus injection, an external reservoir (e.g., an intravenous bag), or a continuous intravenous-, subcutaneous-, or intraperitoneal administration from the internal source (e.g., a bioerodable implant).

In addition, the fusion protein of the present invention may be administered to a subject recipient along with other biologically active molecules. The optimal combination of the fusion protein and other molecule(s), dosage forms, and optimal doses may be determined by a conventional experiment well known in the art.

The present invention provides a use of the inventive pharmaceutical composition containing a fusion protein as an effective component for preventing or treating hepatitis, hepatic fibrosis and hepatic cirrhosis.

The present invention provides a use of the inventive pharmaceutical composition containing a fusion protein as an effective component for preparing a composition for preventing or treating hepatitis, hepatic fibrosis and hepatic cirrhosis.

In still another aspect, the present invention provides an isolated nucleic acid molecule encoding the fusion protein. The isolated nucleic acid molecule may be selected from the group consisting of DNA, RNA, and mRNA, and specifically, it may be DNA.

In such case, the isolated nucleic acid molecules encoding the fusion protein may have different sequences with each other due to codon redundancy. Furthermore, as long as the isolated nucleic acid can produce the fusion protein, the isolated nucleic acid may be appropriately modified, or a nucleotide may be added to the N-terminus or C-terminus of the isolated nucleic acid, according to desired purposes.

The isolated nucleic acid molecules may include, for example, a nucleotide sequence represented by any one of SEQ ID NO: 71 to 80.

In still another aspect, the present invention provides an expression vector comprising the isolated nucleic acid molecule.

As used herein, the term "expression vector" refers to a vector containing a nucleic acid sequence, which is suitable for the transformation of a host cell and directs or controls the expression of an inserted heterogenous nucleic acid sequence. The expression vector includes a linear nucleic acid, a plasmid, a phagemid, a cosmid, an RNA vector, a viral vector, and analogues thereof. Examples of the viral vector include a retrovirus, an adenovirus and an adeno-associated virus, but are not limited thereto.

As used herein, the term "expression of a heterogeneous nucleic acid sequence" or "expression" of a target protein refers to transcription of an inserted DNA sequence, translation of an mRNA transcript, and production of an Fc fusion protein product, an antibody or an antibody fragment.

A useful expression vector may be RcCMV (Invitrogen, Carlsbad) or a mutant thereof. The useful expression vector may include a human cytomegalovirus (CMV) promoter for promoting a continuous transcription of a target gene in a mammalian cell, and a bovine growth hormone polyadenylation signal sequence for enhancing the level of post-transcriptional RNA stability. In an exemplary embodiment of the present invention, the expression vector is pAD15, which is a modified vector of RcCMV.

In still another aspect, the present invention provides a host cell comprising the expression vector.

As used herein, the term "host cell" refers to a prokaryotic cell or eukaryotic cell into which a recombinant expression vector may be introduced. As used herein, the term "transformed" or "transfected" refers to introduction of a nucleic acid (e.g., a vector) into a cell by various technologies known in the art.

An appropriate host cell may be transformed or transfected with a DNA sequence of the present invention and may be used for the expression and/or secretion of the target protein. Examples of the appropriate host cell that may be used in the present invention include immortal hybridoma cells, NS/0 myeloma cells, 293 cells, Chinese hamster ovary (CHO) cells, HeLa cells, CAP cells (human amniotic fluid-derived cells), and COS cells.

MODE FOR INVENTION

Hereinafter, exemplary embodiments of the present invention will be described in detail with reference to the examples. However, these examples according to the present invention can be modified in many different forms and the scope of the present invention should not be construed as limited to the examples set forth herein.

Preparation Example 1. Preparation and Purification of Fusion Protein Containing FGF21 Mutant Protein Preparation Example 1-1. Preparation of Expression Vectors for Expression of FGF21 Mutant Proteins In order to improve the stability, activity and pharmacokinetic profiles of the FGF21 in an Fc-FGF21 structure, mutation studies of FGF21 were performed.

Specifically, a protein mutant was designed for the LLLE (SEQ ID NO: 81) region (the amino acids at positions 98 to 101 from the N-terminus of the FGF21 protein of SEQ ID NO: 1) and GPSQG (SEQ ID NO: 82) region (the amino acids at positions 170 to 174 from the N-terminus of the FGF21 protein of SEQ ID NO: 1), and A180 region, which were expected to significantly affect protein activities based on 3-dimensional structure analysis of the FGF21 proteins.

The position, sequence information, target and expected effect of each mutation introduced into the FGF21 protein are listed in Table 1 below. In Table 1, N represents glycosylated asparagine (N).

TABLE 1

| Sequence | Position | Original sequence | Mutated sequence | Target | Expected effect |
|---|---|---|---|---|---|
| EIRP (SEQ ID NO: 68) | 98-101 | LLLE (SEQ ID NO: 81) | EIRP (SEQ ID NO: 68) | Substitution with FGF19 sequence | Improvement of stability and pharmacokinetics |
| TGLEAV (SEQ ID NO: 69) | 170-174 | GPSQG (SEQ ID NO: 82) | TGLEAV (SEQ ID NO: 70) | Substitution with FGF19 sequence | Improvement of pharmacokinetics |
| TGLEAN (SEQ ID NO: 70) | 170-174 | GPSQG (SEQ ID NO: 82) | TGLEA$\underline{N}$ (SEQ ID NO: 70) | Substitution with FGF19 sequence, and addition of N-glycosylation | Improvement of pharmacokinetics |
| G170N | 170 | G | $\underline{N}$ | Point mutation, and addition of N-glycosylation | Improvement of pharmacokinetics |
| G174N | 174 | G | $\underline{N}$ | Point mutation, and addition of N-glycosylation | Improvement of pharmacokinetics |
| A180E | 180 | A | E | Point mutation | Improvement of pharmacokinetics |

Further, FGF21 mutant proteins including the mutations described in Table 1 are listed in Table 2 below.

TABLE 2

| SEQ ID NO | Sequence of FGF21 mutant protein |
|---|---|
| 6 | FGF21 (EIRP (SEQ ID NO: 68)) |
| 7 | FGF21 (TGLEAV (SEQ ID NO: 69)) |
| 8 | FGF21 (TGLEAN (SEQ ID NO: 70)) |
| 9 | FGF21 (G170N) |
| 10 | FGF21 (G174N) |
| 11 | FGF21 (EIRP, (SEQ ID NO: 68), TGLEAV (SEQ ID NO: 69)) |
| 12 | FGF21 (EIRP, (SEQ ID NO: 68), TGLEAN (SEQ ID NO: 70)) |
| 13 | FGF21 (EIRP (SEQ ID NO: 68), G170N) |
| 14 | FGF21 (EIRP (SEQ ID NO: 68), G174N) |
| 15 | FGF21 (EIRP (SEQ ID NO: 68), A180E) |
| 16 | FGF21 (TGLEAV (SEQ ID NO: 69), A180E) |
| 17 | FGF21 (TGLEAN (SEQ ID NO: 70), A180E) |
| 18 | FGF21 (G170N, A180E) |
| 19 | FGF21 (G174N, A180E) |
| 20 | FGF21 (EIRP (SEQ ID NO: 68), TGLEAV (SEQ ID NO: 69), A180E) |
| 21 | FGF21 (EIRP (SEQ ID NO: 68), TGLEAN, (SEQ ID NO: 70), A180E) |
| 22 | FGF21 (EIRP (SEQ ID NO: 68), G170N, A180E) |
| 23 | FGF21 (EIRP (SEQ ID NO: 68), G174N, A180E) |

Nucleotides encoding amino acids were loaded to the expression vector such that, from the N-terminus to the C-terminus in the order, a fused carrier, a linker, and FGF21 mutant protein were expressed. The material code of each FGF21 mutant fusion protein, sequence of mutation introduced into FGF21, sequence of fusion carrier and linker sequence are listed in Table 3 below. In Table 3, N represents glycosylated asparagine (N).

TABLE 3

| SEQ ID NO | Material code | Sequence of FGF21 mutation | Fusion carrier | Linker sequence |
|---|---|---|---|---|
| 27 | DFD1 | EIRP, TGLEAV | hyFc (SEQ ID NO: 26) | C (SEQ ID NO: 2) |
| 28 | DFD3 | TGLEAV | hyFc (SEQ ID NO: 26) | AKA (SEQ ID NO: 3) |
| 29 | DFD4 | TGLEAV | hyFc (SEQ ID NO: 26) | GS3 (SEQ ID NO: 4) |
| 30 | DFD5 | TGLEA$\underline{N}$ | hyFc (SEQ ID NO: 26) | GS3 (SEQ ID NO: 4) |
| 31 | DFD6 | G170$\underline{N}$ | hyFc (SEQ ID NO: 26) | GS3 (SEQ ID NO: 4) |
| 32 | DFD6 (E. coli) | G170$\underline{N}$ | hyFc (SEQ ID NO: 26) | GS3 (SEQ ID NO: 4) |
| 33 | DFD7 | G174$\underline{N}$ | hyFc (SEQ ID NO: 26) | GS3 (SEQ ID NO: 4) |
| 34 | DFD9 | none | hyFc (SEQ ID NO: 26) | GS3 (SEQ ID NO: 4) |
| 35 | DFD13 | EIRP, TGLEAV | hyFc (SEQ ID NO: 26) | GS3 (SEQ ID NO: 4) |
| 36 | DFD18 | EIRP, TGLEAV, A180E | hyFc (SEQ ID NO: 26) | GS3 (SEQ ID NO: 4) |
| 37 | DFD72 | EIRP, TGLEA$\underline{N}$, A180E | hyFc (SEQ ID NO: 26) | GS3 (SEQ ID NO: 4) |
| 38 | DFD73 | EIRP, G170$\underline{N}$ | hyFc (SEQ ID NO: 26) | GS3 (SEQ ID NO: 4) |
| 39 | DFD74 | EIRP, G170$\underline{N}$, A180E | hyFc (SEQ ID NO: 26) | GS3 (SEQ ID NO: 4) |
| 40 | RGE (Amgen) | L98R, P171G, A180E | IgG1Fc mutant | GS3 (SEQ ID NO: 4) |
| 41 | Fc-FGF21 (Lilly) | X | IgG4Fc mutant (SEQ ID NO: 25) | GS3A (SEQ ID NO: 5) |

In order to produce the FGF21 mutant fusion proteins, the nucleotide sequences encoding each of the FGF21 mutant proteins were synthesized by consulting with Bioneer Corporation (Korea) based on the amino acid sequence of each protein. NheI and NotI restriction enzyme sequences were added to the 5' terminus and 3' terminus of the nucleotide sequences encoding each of the FGF21 mutant proteins and an initiation codon for protein translation and a leader sequence (MDAMLRGLCCVLLLCGAVFVSPSHA) (SEQ ID NO: 83) capable of secreting the expressed protein to the outside of a cell were inserted next to the restriction enzyme sequence at the 5' terminus. A termination codon was inserted next to the nucleotide sequence, which encodes each of the FGF21 mutant fusion proteins. The nucleotide sequence encoding each of the FGF21 mutant fusion proteins was cloned into a pTrans-empty expression vector by using the two restriction enzymes of NheI and NotI. The pTrans-empty expression vector, which has a simple structure including a CMV promoter, a pUC-derived replication origin, an SV40-derived replication origin and an ampicillin-resistant gene, was purchased from CEVEC Pharmaceuticals (Germany).

Meanwhile, in the case of DFD6 (*E. coli* expression) and Fc-FGF21 fusion protein RGE (Amgen), a nucleotide sequence encoding each fusion protein was inserted into pET30a expression vector for *E. coli* expression.

Preparation Example 1-2. Construction of Plasmid DNA for Expression of FGF21 Mutant Fusion Proteins

*E. coli* was transformed with each of the expression vectors constructed in Preparation Example 1-1 to obtain a large amount of plasmid DNA to be used for expression. *E. coli* cells, whose cell walls were weakened, were transformed with each expression vector through heat shock, and the transformants were plated out on LB plates to obtain colonies. The colonies thus obtained were inoculated into LB media, cultured at 37° C. for 16 hours, and each *E. coli* culture containing each expression vector was obtained in a volume of 100 mL. The *E. coli* thus obtained was centrifuged to remove the culture medium, and then P1, P2, P3 solutions (QIAGEN, Cat No.:12963) were added to break the cell walls, thereby obtaining a DNA suspension in which proteins and DNAs were separated. Plasmid DNA was purified from the DNA suspension thus obtained by using a QIAGEN™ DNA purification column. The eluted plasmid DNA was identified through an agarose gel electrophoresis, and concentrations and purities were measured by using a NANODROP™ device (Thermo scientific, NANODROP™ Lite). The DNA thus obtained was used for expression.

Preparation Example 1-3. Expression of Fusion Proteins in CAP-T Cells

Human cell lines were transfected with each plasmid DNA type obtained in Preparation Example 1-2. Each plasmid DNA type was transduced into CAP-T cells (CEVEC), which had been cultured in PEM medium (Life technologies), by using PEI solution (Polyplus, Cat. No.:101-10N). The mixed solution of DNA and the PEI solution was mixed with the cell suspension by using a FREESTYLE™ 293 expression medium (Invitrogen), cultured at 37° C. for 5 hours, and PEM medium was added. After culturing at 37° C. for 5-7 days, the culture was centrifuged to remove cells and a supernatant including FGF21 mutant fusion proteins was obtained.

Preparation Example 1-4. Expression and Purification of FGF21 Mutant Fusion Proteins in *E. coli*

*E. coli* strain BL21 (DE3) was transformed with each plasmid DNA expressing DFD6 (*E. coli*) and RGE (Amgen) fusion proteins. The transformed *E. coli* expressing each fusion protein was inoculated into 20 mL of LB media, cultured at 37° C. for 15 hours with shaking, and then a portion of the culture media was inoculated into 100 mL of LB media, and cultured at 37° C. for 16 hours with shaking. Upon completion of culturing, the culture was centrifuged to obtain *E. coli* pellets, and then cells were disrupted using a high pressure cell disruptor to obtain inclusion bodies.

The obtained inclusion bodies were purified by washing and elution, followed by a protein refolding process. Specifically, the obtained inclusion bodies were washed 2-3 times with a buffer solution (pH 8.0) containing 0.5% Triton X-100, 50 mM Tris, 1 mM EDTA and 0.1 M NaCl to remove bacterial protein, and then resuspended in 8 M urea buffer containing 8 M urea, 50 mM Tris and 1 mM DTT. Since the proteins in 8 M urea buffer were completely denatured, a protein refolding process was performed as follows.

First, urea was removed from 8 M urea buffer by stepwise dilution with 20 mM glycine, pH 9.0 buffer. From 2 M urea, copper sulfate ($CuSO_4$) was added to a concentration of 80 to induce stable structural folding of the protein. The protein completing the refolding process was suspended in PBS buffer solution (pH 7.4), and the suspension was filtered with a 0.22 μm filter to remove impurities, and then loaded into a Protein A affinity chromatography column. The column was washed with 1×PBS buffer solution (pH 7.4) and then the proteins were eluted using 100 mM glycine buffer solution (pH 3.0) to prepare DFD6 (*E. coli*) fusion protein.

In the case of RGE (Amgen) fusion protein, the protein completing the refolding process was suspended in 50 mM Tris buffer solution (pH 8.0), the suspension was filtered with a 0.22 μm filter to remove impurities, and then loaded into an anion exchange resin column (POROS® HQ 50 μm, Thermo Fisher Scientific). The column was washed with 50 mM Tris buffer solution (pH 8.0), and then 50 mM Tris buffer solution (pH 8.0) was administered along the concentration gradient to elute RGE (Amgen) fusion protein. The RGE (Amgen) fusion protein obtained by the anion exchange resin was mixed with ammonium sulfate to the concentration of 1 M, and then purified using a hydrophobic interaction chromatography column (Phenyl sepharose FF, GE Healthcare). Specifically, the column was washed with 50 mM Tris buffer solution (pH 8.0) containing 1 M ammonium sulfate, 50 mM Tris buffer solution (pH 8.0) was administered along the concentration gradient, and the eluted fractions were analyzed through 10% Tris-glycine gel electrophoresis. The gel was dyed with coomassie brilliant blue R with mild shaking, and the fractions containing FGF21 mutant fusion protein with high purity were collected and then dialyzed overnight at 4° C. using a final buffer solution (1×PBS, 1 mM EDTA, pH 7.4). Upon completion of the dialysis, the obtained protein stock solution was concentrated at 3,000 rpm by using a 30,000 MW cut-off centrifugation filter at 4° C. The concentration of FGF21 mutant fusion protein was measured via BCA quantitative analysis.

Preparation Example 1-5. Purification of FGF21 Mutant Fusion Proteins

Protein A affinity chromatography column (GE Healthcare) was equilibrated with 1×PBS buffer solution (pH 7.4).

The culture supernatant including each FGF21 mutant fusion protein obtained in Preparation Example 1-3 was filtered with a 0.2 μm filter, and then loaded into a Protein A affinity chromatography column. The column was washed with 1×PBS buffer solution (pH 7.4) and then proteins were eluted using 100 mM glycine buffer solution (pH 3.0). The fusion proteins obtained by affinity chromatography were purified using an anion exchange resin column (POROS® HQ 50 μm, Thermo Fisher Scientific). The anion exchange resin column was equilibrated with 50 mM Tris buffer solution (pH 8.0), before the FGF21 mutant fusion proteins were eluted from the column. Specifically, after washing the column with 50 mM Tris buffer solution (pH 8.0), 50 mM Tris buffer solution (pH 8.0) was dispensed along the concentration gradient and the eluted fractions were analyzed. Each eluted fraction was analyzed using size exclusion chromatography (SEC-HPLC), and the fractions including FGF21 mutant fusion proteins with high purity were collected. The concentration and quantitative analysis were performed in accordance with the methods described in Preparation Example 1-4.

Experimental Example 1. In Vitro Activities of Fusion Proteins

Experimental Example 1-1. Effect of FGF21 mutations on protein activity

The in vitro activities of fusion proteins DFD4, DFD5, DFD6, DFD6 (E. coli), DFD7, DFD9, DFD13, DFD18, DFD72, DFD73 and DFD74 prepared in Preparation Example 1 were measured.

Specifically, the in vitro FGF21 activities of the fusion proteins were evaluated using a HEK293 cell line (Yuhan Corporation, Korea) which was modified to overexpress human β-klotho, a coreceptor of FGF21. For the evaluation of activity, the concentrates containing the fusion proteins prepared in Preparation Examples 1-4 and 1-5 were subjected to a 3-fold serial dilution at a concentration of 3 μM. After having been cultured in a serum-deficient state for 5 hours, the cell line overexpressing human β-klotho was treated with the diluted fusion proteins for 20 minutes, and then was lysed by adding cytolysis buffer (Cisbio/Cat #64ERKPEG) with stirring at 60 rpm for 30 minutes at room temperature. The cell lysate solution was mixed with antibodies (Cisbio/Cat #64ERKPEG), which can detect extracellular signal-regulated kinase (ERK) and phosphorylated ERK, and the mixture was maintained at room temperature for 2 hours. Fluorescence was detected using a fluorometric detector (TECAN/GENiosPro). The activities of the fusion proteins were measured by comparing their $EC_{50}$ values. The results are shown in FIGS. 1A to 1C.

Figure 1B:
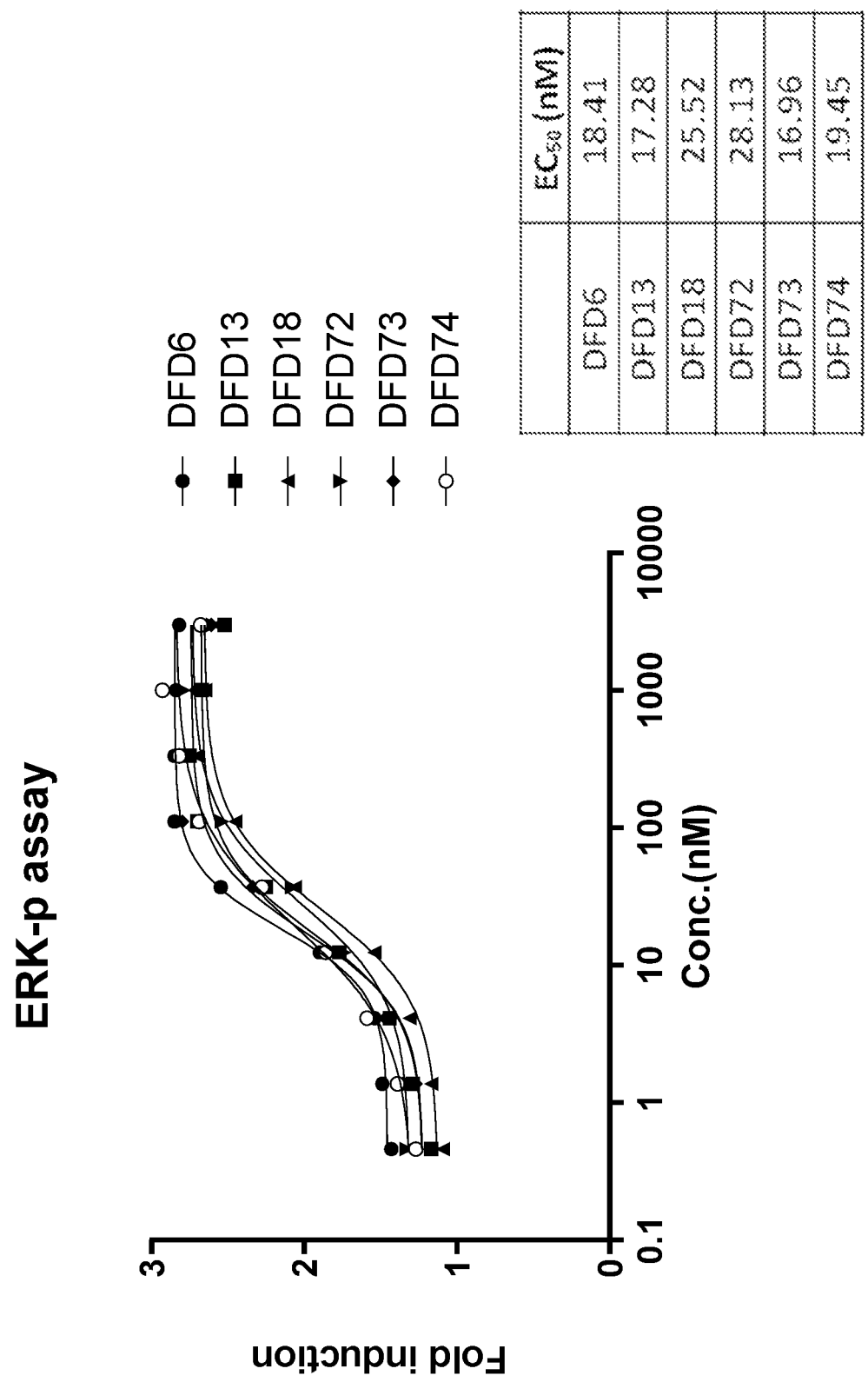
FIG. 1B is a graph showing the in vitro activities of DFD6, DFD13, DFD18, DFD72, DFD73 and DFD74, as fusion proteins including FGF21 mutant fusion proteins, using a HEK293 cell line in which human β-klotho is overexpressed. No FGF21 mutant fusion proteins exhibited a significant decrease in activity due to the introduction of a mutation.
Figure 1C:
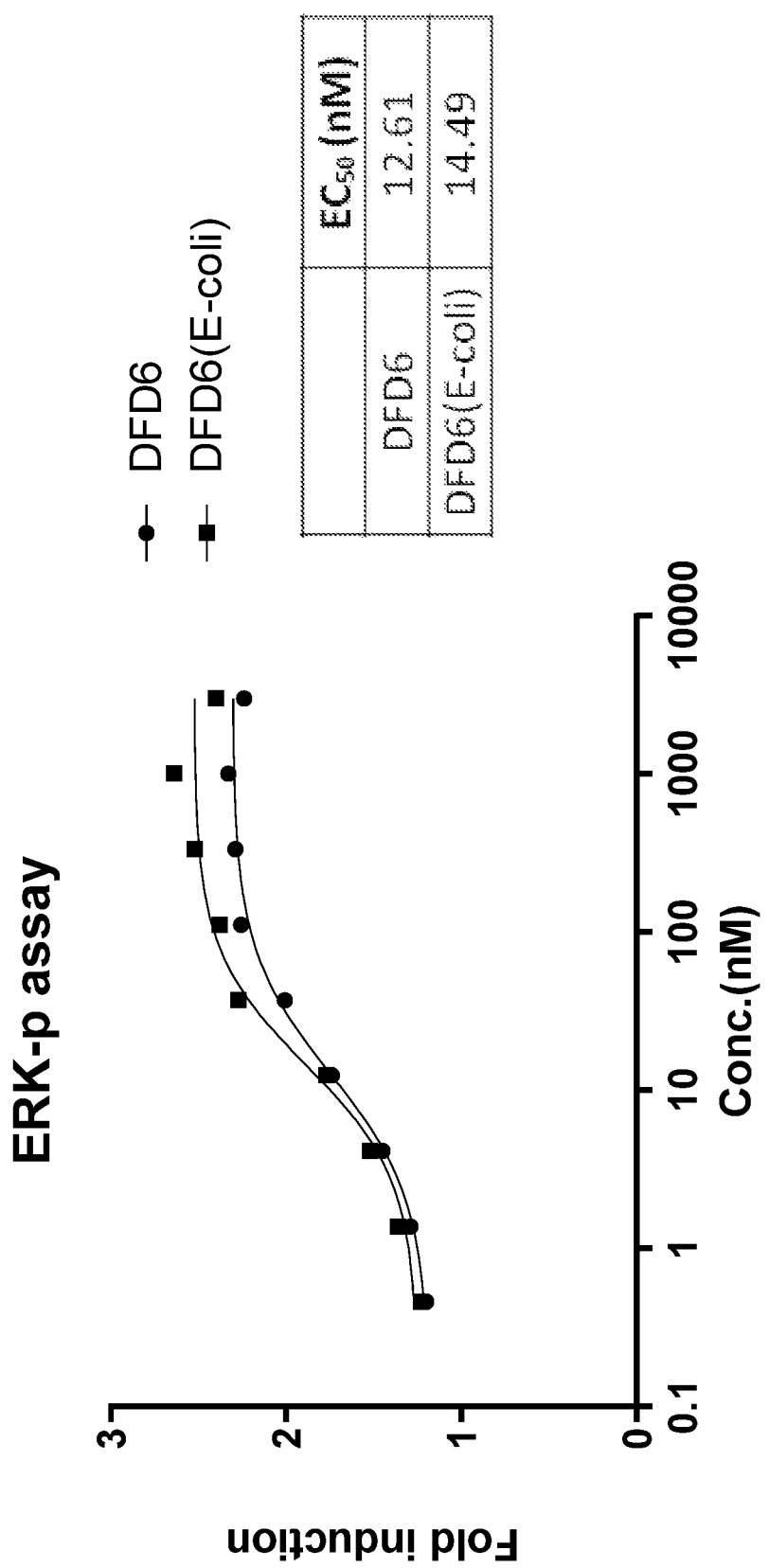
FIG. 1C is a graph showing the in vitro activities of DFD6 and DFD6 (E. coli), as fusion proteins including FGF21 mutant fusion proteins, using a HEK293 cell line in which human β-klotho is overexpressed. No FGF21 mutant fusion proteins exhibited a significant decrease in activity due to the introduction of a mutation.

As shown in FIGS. 1A to 1C, it was confirmed that the in vitro activities of the fusion proteins prepared by introducing mutation sequences into the wild-type FGF21 protein were not inhibited, and the activities of each fusion protein were similar to each other. It was also confirmed that through the DFD6 (E. coli) sample expressed in E. coli and the DFD6 sample expressed in animal cells, the in vitro activities of the fusion proteins prepared by introducing N-glycosylation mutation into the wild-type FGF21 protein were not inhibited.

Experimental Example 1-2. Effect of Linker Sequence on Protein Activity

The in vitro activities of fusion proteins DFD1, DFD3, DFD4 and DFD13 prepared in Preparation Example 1 were measured.

Specifically, the FGF21 activities of the fusion proteins were measured by using the concentrates containing the fusion proteins prepared in Preparation Example 1-5 in accordance with the methods described in Experimental Example 1-1. The results are shown in FIGS. 2A and 2B.

Figure 2A:
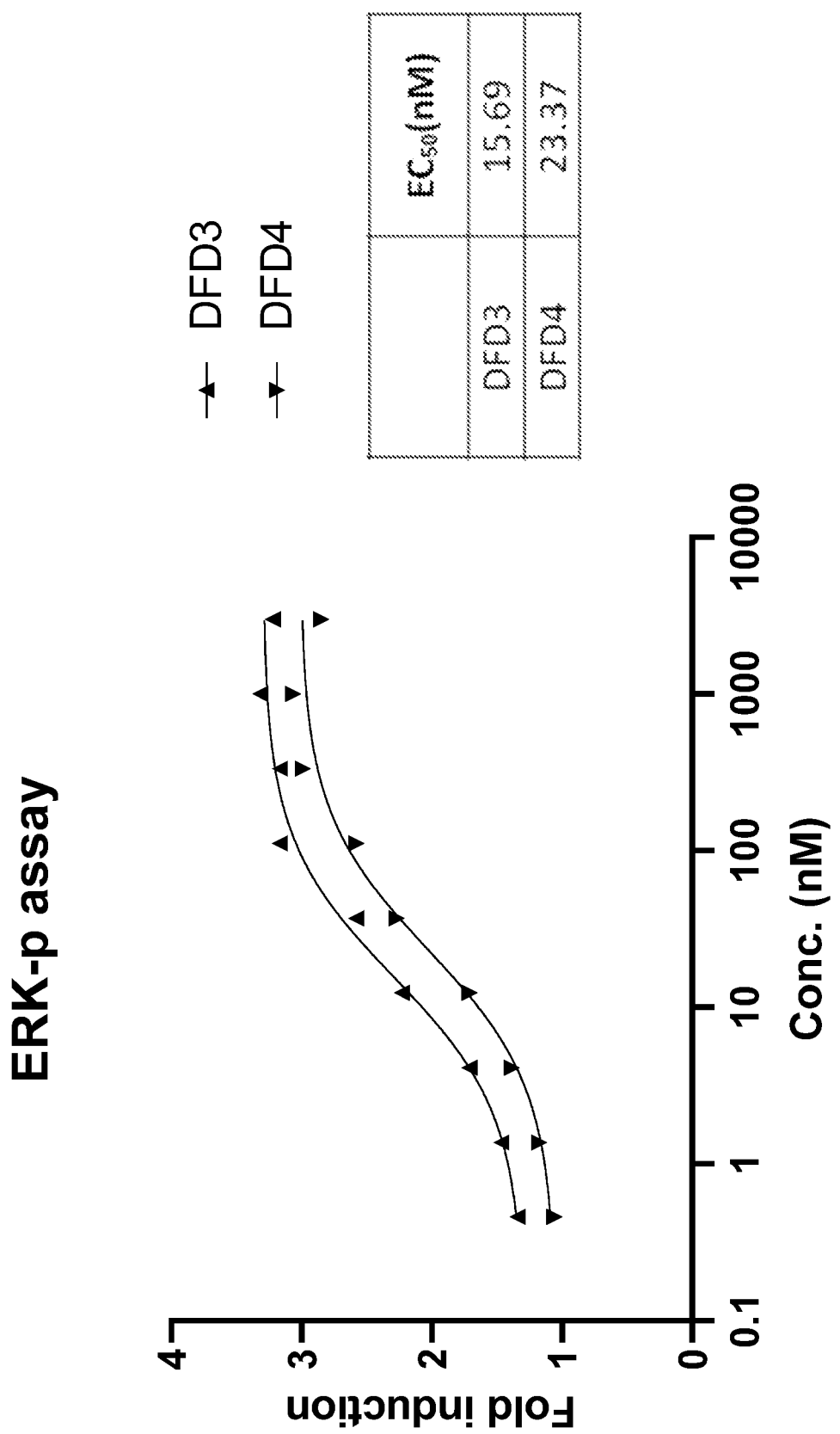
FIG. 2A is a graph showing the in vitro activities of DFD3 and DFD4, as FGF21 mutant fusion proteins into which a linker connecting the N-terminus of FGF21 and Fc region was introduced, using a HEK293 cell line in which human β-klotho is overexpressed. No FGF21 mutant fusion protein exhibited a significant decrease in activity, although a slight difference was shown in activity depending on the linker sequence.
Figure 2B:
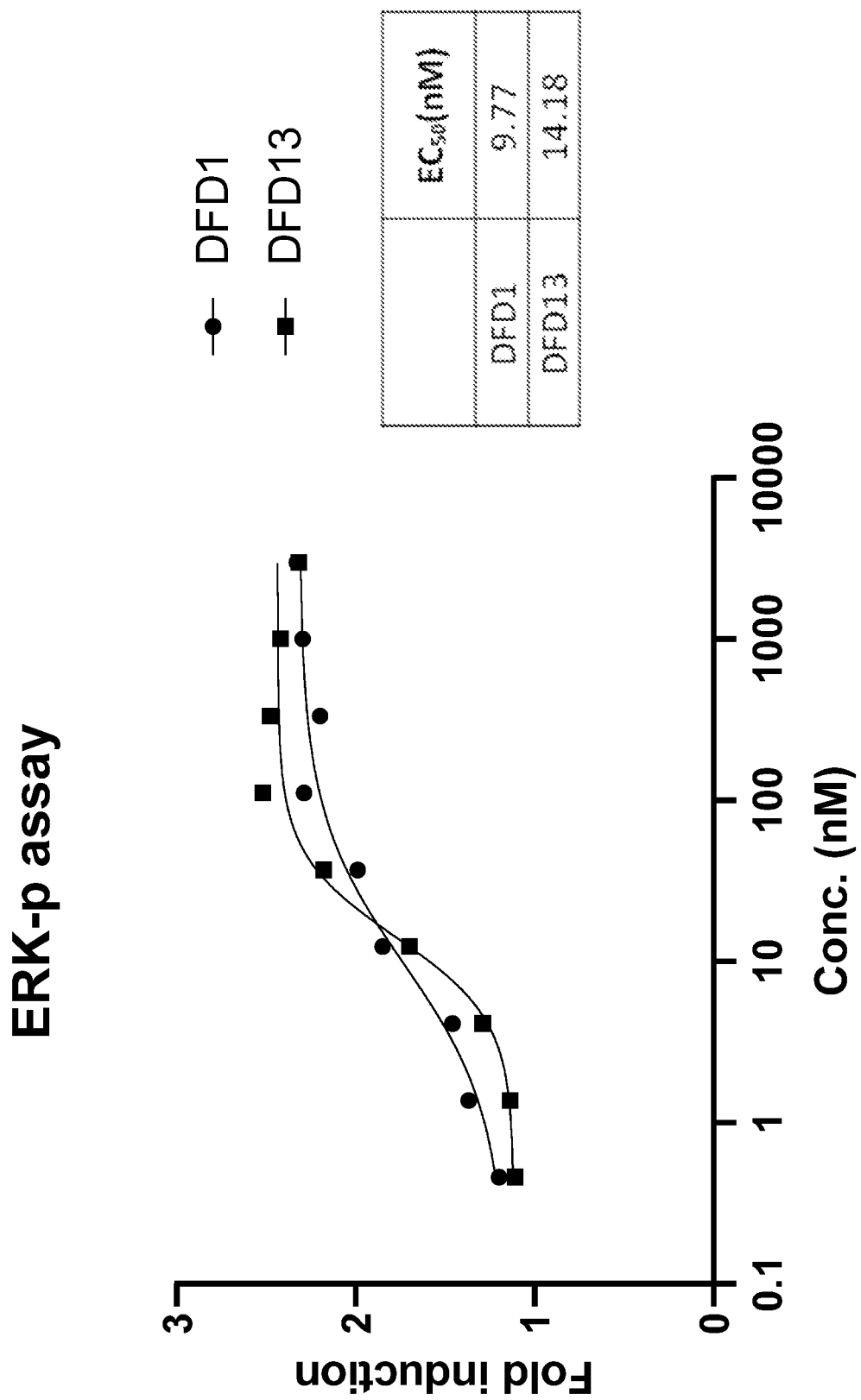
FIG. 2B is a graph showing the in vitro activities of DFD1 and DFD13, as FGF21 mutant fusion proteins into which a linker connecting the N-terminus of FGF21 and Fc region was introduced, using a HEK293 cell line in which human β-klotho is overexpressed. No FGF21 mutant fusion protein exhibited a significant decrease in activity, although a slight difference was shown in activity depending on the linker sequence.

It was confirmed that no FGF21 mutant fusion protein showed a significant decrease in the activity, although a slight difference was shown in the activity depending on the linker sequence, as shown in FIGS. 2A and 2B.

Experimental Example 1-3. Experimental Results for DFD1, RGE (Amgen) and Fc-FGF21 (Lilly)

The in vitro activities of fusion protein DFD1 prepared in Preparation Example 1 and control proteins RGE (Amgen) and Fc-FGF21 (Lilly) were measured.

Specifically, the FGF21 activities of the fusion proteins were measured by using the concentrates containing the fusion proteins prepared in Preparation Example 1-5 and the control proteins in accordance with the methods described in Experimental Example 1-1. The results are shown in FIG. 3.

Figure 3:
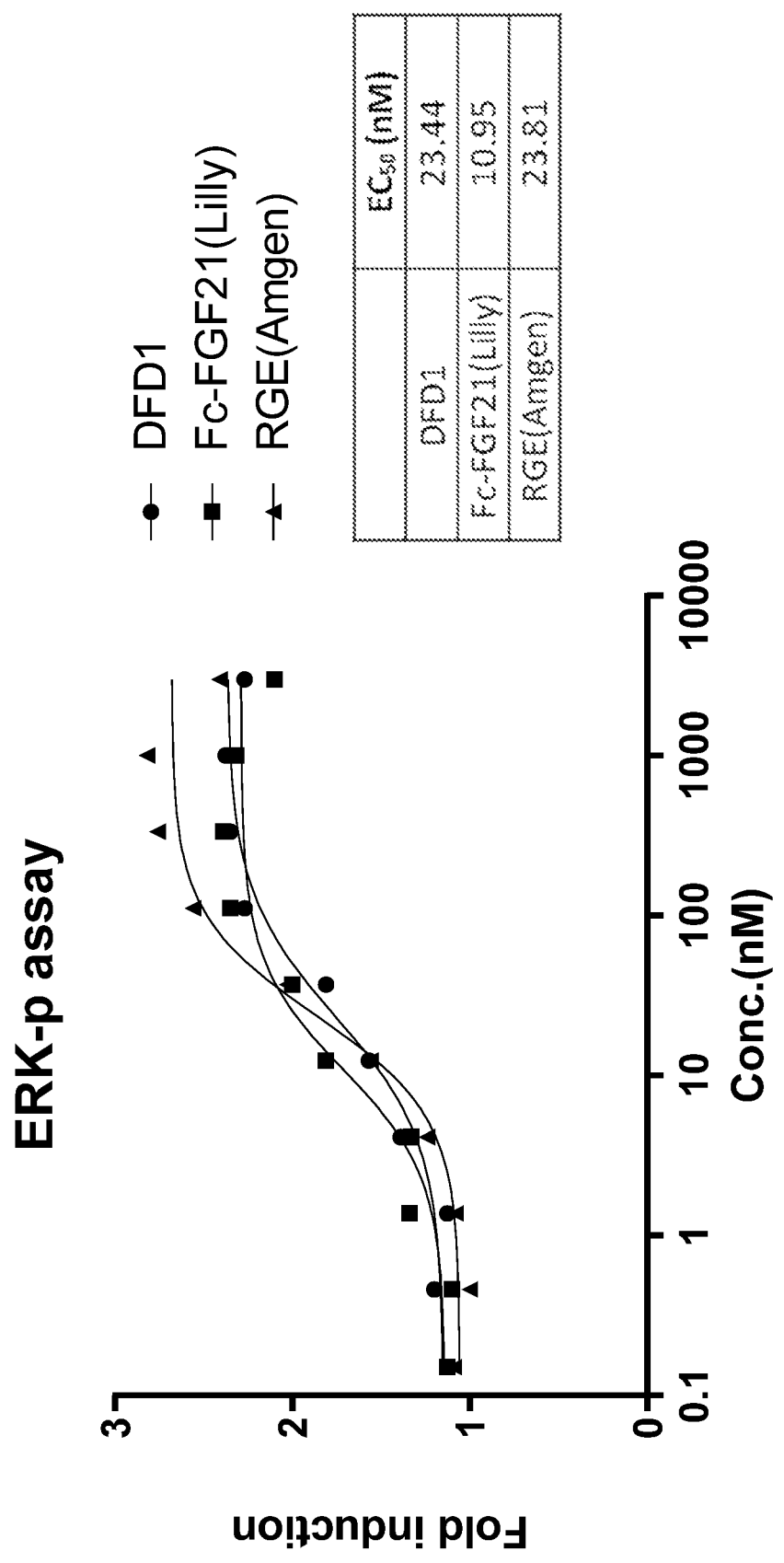
FIG. 3 is a graph showing the in vitro activities of RGE (Amgen), Fc-FGF21 (Lilly) and DFD1 using a HEK293 cell line in which human β-klotho is overexpressed. DFD1 and RGE (Amgen) had similar activities, while Fc-FGF21 (Lilly) had in vitro activity two times higher than the other proteins.

It was confirmed that DFD1 and RGE (Amgen) had similar in vitro activity, while Fc-FGF21 (Lilly) had in vitro activity two times higher than those of the other proteins, as shown in FIG. 3.

Experimental Example 2. Evaluation of Stability of Fusion Proteins

Experimental Example 2-1. Experimental method for evaluating stability

In order to measure the quantity of protein aggregates at the initial stage of the sample preparation, high molecular weight aggregates (% HMW) were quantified using a size-exclusion chromatography (SEC-HPLC) method. The results are shown in FIGS. 4A to 4C.

Specifically, a TOSOHAAS™ model TSK-GEL G3000SW$_{XL}$™ column was used for the SEC-HPLC method. The column was equilibrated by flowing a buffer solution (1×PBS, 1 mM EDTA, pH 7.4) at a flow rate of 1 mL/min. The DFD4 and DFD13 protein stock solutions prepared in Preparation Examples 1-5 were concentrated to a target concentration of 20 mg/mL or higher at 3,000 rpm using a 30,000 MW cut-off centrifugation filter at 4° C. After the measurement of the concentration of each sample by BCA quantitative analysis, the samples were diluted with a buffer solution (1×PBS, 1 mM EDTA, pH 7.4) to a final concentration of 20 mg/mL. To measure the initial HMW % of DFD4 and DFD13, a 20 mg/ml sample was diluted to the concentration of 1 mg/ml with 1×PBS, 1 mM EDTA at pH 7.4. Then, each 100 μl of the diluted samples was injected into SEC-HPLC column and analyzed. For the stability evaluation of each sample, % HMW of the samples was measured using the SEC-HPLC method on the 4$^{th}$, the 8$^{th}$ and the 14$^{th}$ days while storing them at 5° C., 25° C. and 37° C. for two weeks.

Figure 4A:
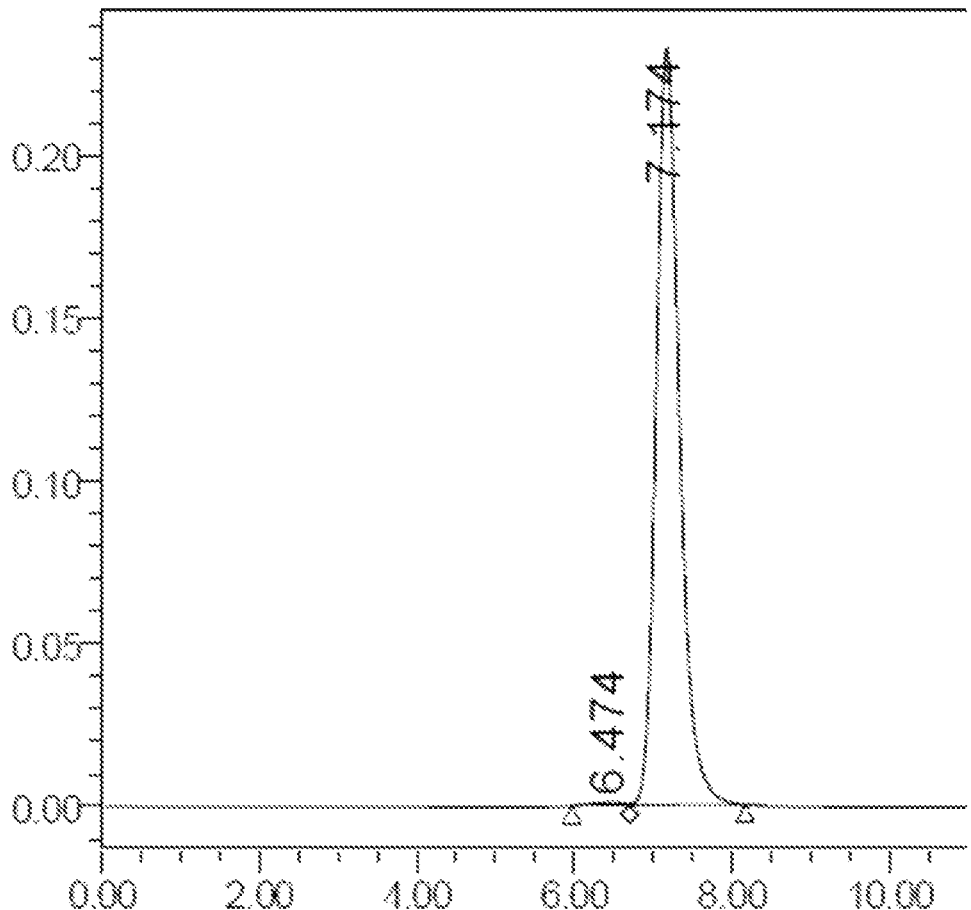
FIG. 4A is a result of size exclusion chromatography analysis of DFD4, a FGF21 mutant fusion protein.
Figure 4B:
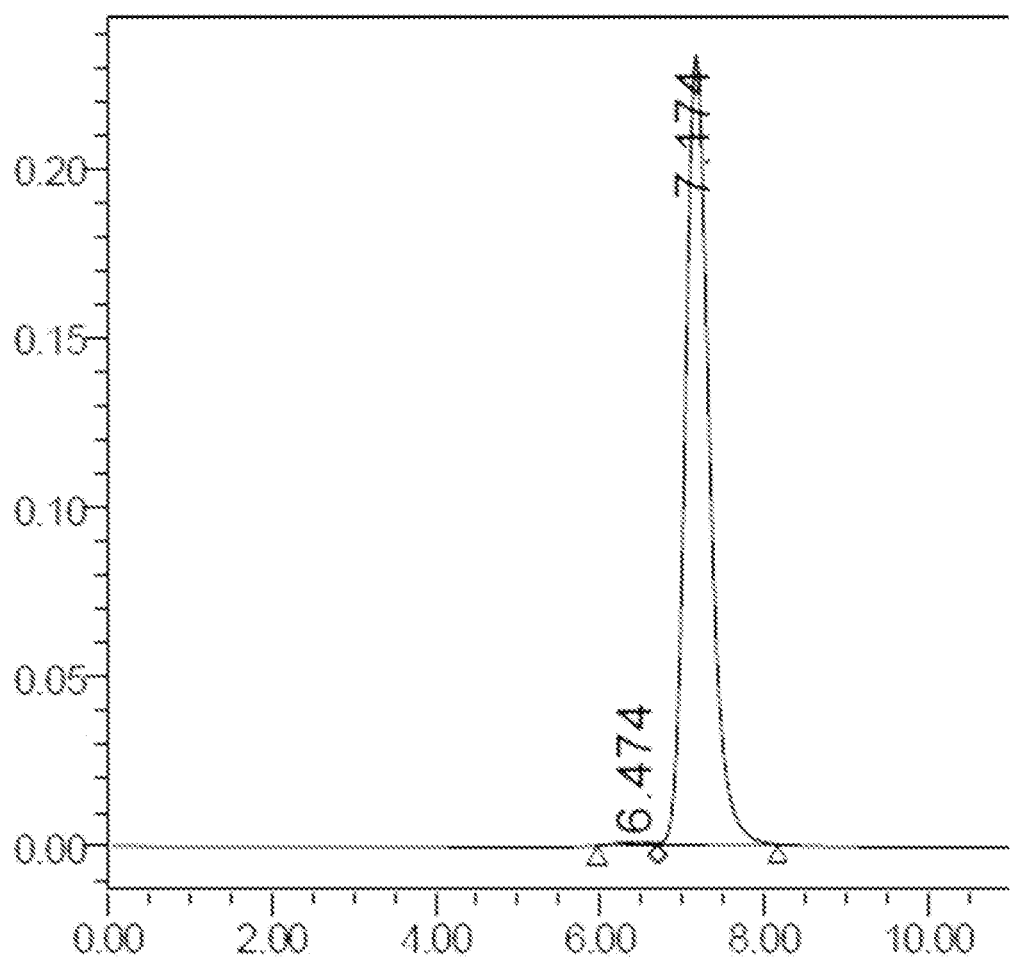
FIG. 4B is a result of size exclusion chromatography analysis of DFD13, a FGF21 mutant fusion protein in which EIRP mutation was introduced.
Figure 4C:
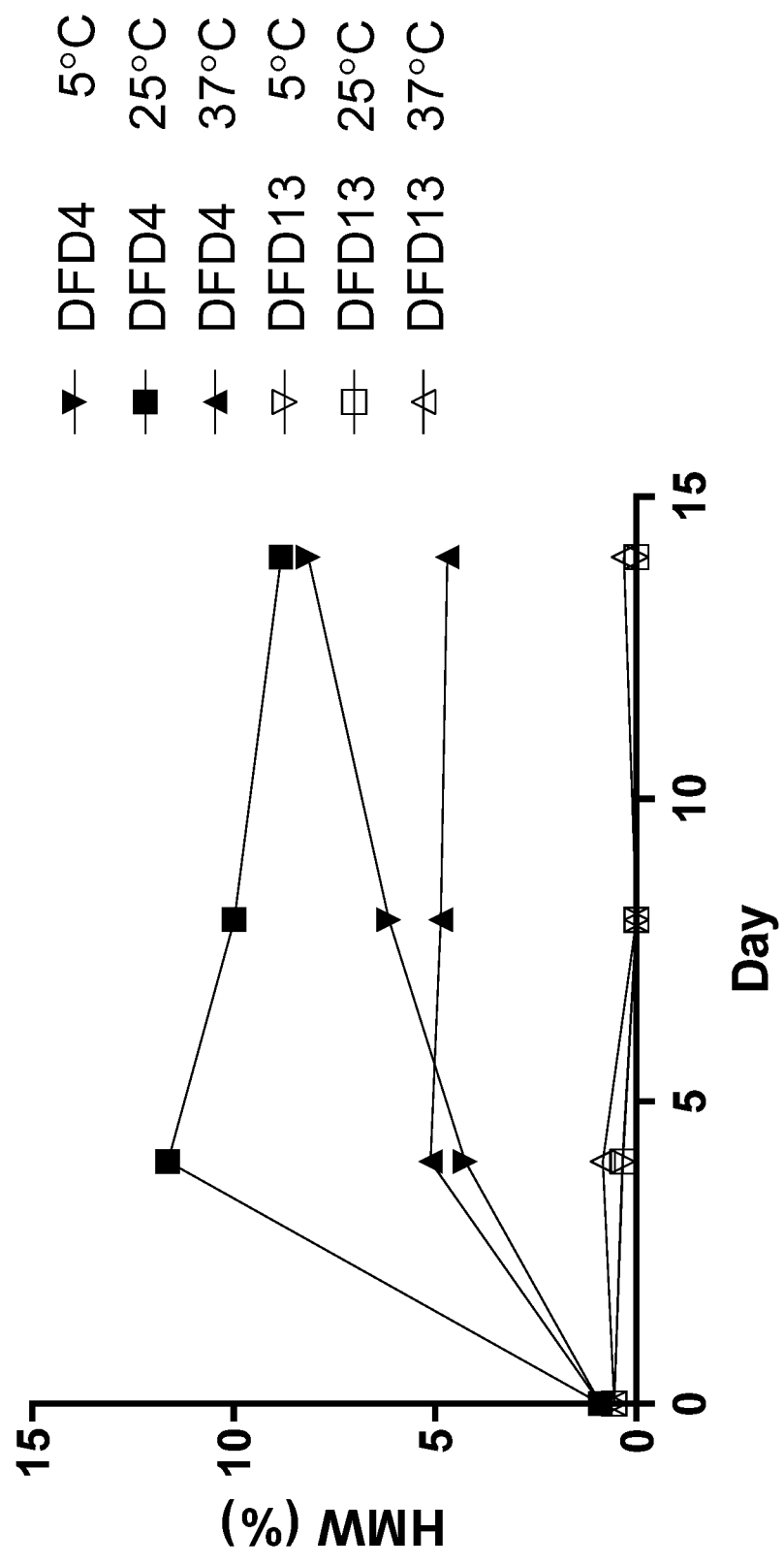
FIG. 4C is a graph comparing the proposed contents of the high molecular weight aggregates (HMW %) of DFD4 and DFD13 using a size exclusion chromatography to verify the effect of the EIRP (SEQ ID NO: 68) mutation of FGF21 on the stability of the fusion protein. It was verified that DFD13 was associated with a lower rate of high molecular weight aggregates (HMW %) at the initial stage and at a time-point of more than 2 weeks later as compared to DFD4, indicating that the introduction of the EIRP (SEQ ID NO: 68) mutation improves the stability of the FGF21 mutant fusion protein, thereby reducing HMW % significantly.

As shown in FIGS. 4A to 4C, it was confirmed that DFD13 had a lower quantity of high molecular weight aggregates (HMW %) at the initial stage and up to the point of 2 weeks as compared with DFD4, indicating that the introduction of the EIRP (SEQ ID NO: 68) mutation improves the stability of the FGF21 mutant fusion protein, thereby reducing HAW % significantly.

Experimental Example 2-2. Stability Results

In order to investigate the effects of the EIRP (SEQ ID NO: 68) mutation introduced into the original sequence LLLE (SEQ ID NO: 81) (amino acid residues at 98-101 of SEQ ID NO: 1) of FGF21 on stability, the stability of DFD4 (SEQ ID NO: 29) and DFD13 (SEQ ID NO: 35) was measured in accordance with the methods described in Experimental Example 2-1. The analysis results for the zero-hour sample (initial stage; Day 0) and 4-, 8-, and 14 day-stored samples of DFD4 and DFD13 are summarized in Table 4 below (in Table 4, N.D. means "not detected").

TABLE 4

Stability of DFD4 and DFD13 for 2 weeks at a concentration of 20 mg/mL (% HMW)

| Day | DFD4 | | | DFD13 | | |
|---|---|---|---|---|---|---|
| | 5° C. | 25° C. | 37° C. | 5° C. | 25° C. | 37° C. |
| 0 | | 0.91 | | | 0.56 | |
| 4 | 4.25 | 11.64 | 5.12 | 0.36 | 0.34 | 0.84 |
| 8 | 6.16 | 9.99 | 4.87 | N.D. | N.D. | N.D. |
| 14 | 8.15 | 8.83 | 4.71 | N.D. | N.D. | 0.32 |

As shown in Table 4, the quantity of % HMW at the initial stage (Day 0) was 0.91% for DFD4, and 0.56% for DFD13. After 2 weeks, the amount of % HMW increased to 8.83% for DFD4, but it was not observed in DFD13, under the condition of storage at 25° C. DFD13 was shown to have a lower % HMW rate at the initial stage and 2 weeks, as compared with DFD4. It was found that as the EIRP (SEQ ID NO: 68) mutation was introduced, the HMW % ratio of the FGF21 mutant fusion protein was greatly reduced.

Experimental Example 3: Pharmacokinetic Measurement of Fusion Protein

Experimental Example 3-1. Experimental Method of Pharmacokinetic Measurement

Six week-old male ICR mice purchased from Orient BIO Co. (Korea) were divided into groups (n=3 per blood collection time) such that the average body weights were similar at one day prior to the drug treatment. Thereafter, the test substances were administered in a single subcutaneous dose of 1 mg/kg (2 mg/kg in the case of RGE), respectively. Blood samples were then collected at 1, 4, 8, 12, 24, 48, 72, and 96 hours after the injection, respectively. The concentration of intact full length FGF21 protein in the blood was measured using an Intact human FGF21 ELISA Kit (F1231-K01, Eagle Biosciences, USA), which has immunoreactivity to the N-terminus and C-terminus of FGF21 protein. The concentrations of the samples in the blood collected until 96 hours after the subcutaneous injection of each fusion protein into the mice were measured, and pharmacokinetic parameters of each substance were calculated.

Experimental Example 3-2. Results of Pharmacokinetic Activity Measurements

Figure 5:
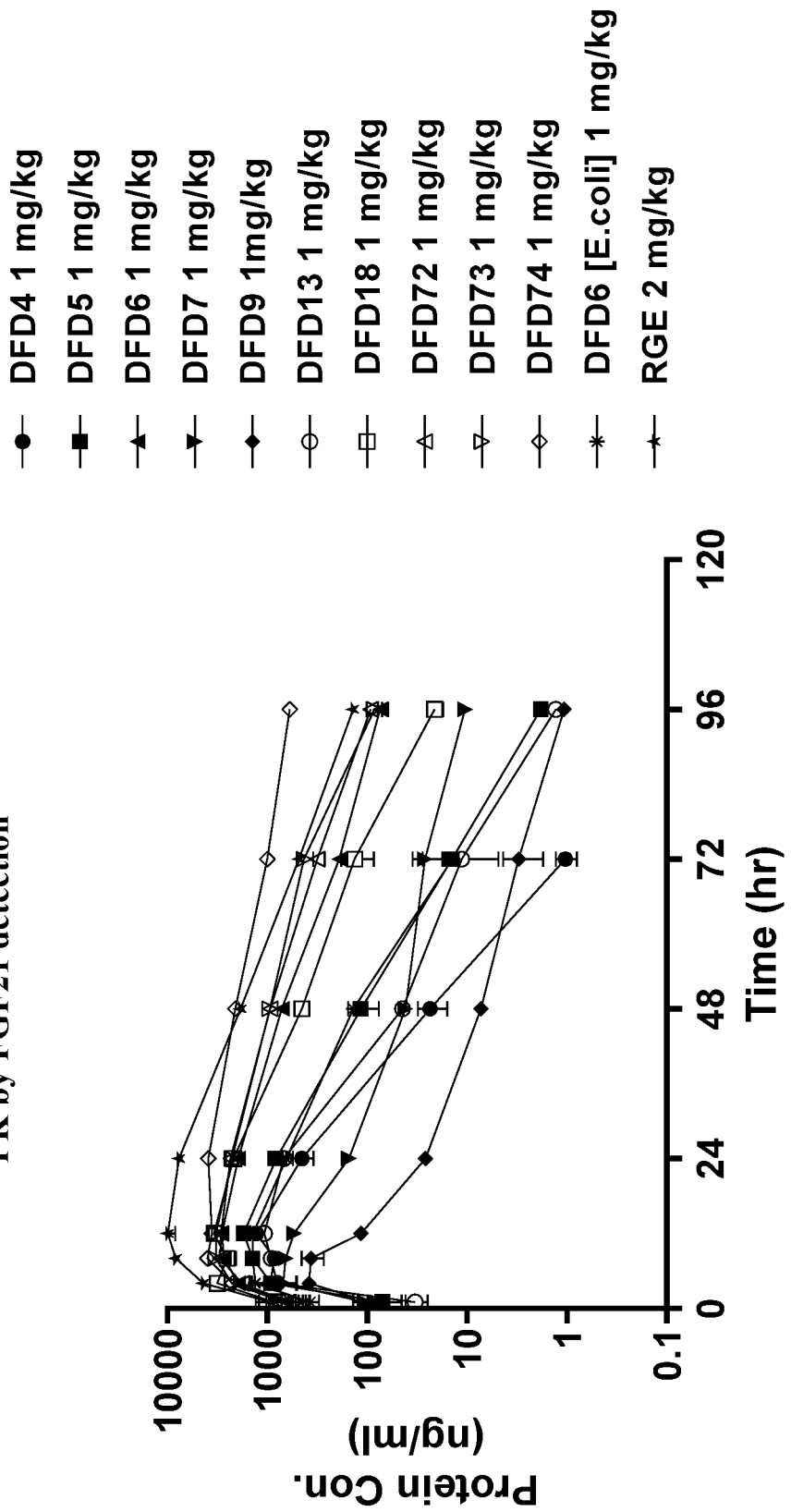
FIG. 5 shows the concentration of each protein in the blood over time for 96 hours after subcutaneous administration of FGF21 mutant fusion proteins. Data are indicated as mean values and standard deviation.

Based on the graph showing the concentrations of each protein in the blood versus time after the subcutaneous administration of fusion proteins in mice (FIG. 5), the pharmacokinetic parameters were calculated. The data are shown in Table 5 below.

TABLE 5

| Parameters | DFD4 | DFD5 | DFD6 | DFD7 | DFD9 | DFD13 | DFD18 | DFD72 | DFD73 | DFD74 | DFD6 (E. coli) | RGE* |
|---|---|---|---|---|---|---|---|---|---|---|---|---|
| $T_{max}$ (hour) | 12 | 12 | 12 | 4 | 4 | 12 | 12 | 8 | 8 | 8 | 8 | 12 |
| $C_{max}$ (ng/mL) | 1288 | 1732 | 2868 | 696 | 384 | 1070 | 3428 | 2962 | 3296 | 3996 | 1399 | 9921 |
| $AUC_{last}$ *225(ng · hr/mL) | 25856 | 40706 | 100107 | 14118 | 4656 | 28785 | 104230 | 115977 | 123511 | 206634 | 37269 | 325747 |
| Half-life (hour) | 5.5 | 8.0 | 14.9 | 19.7 | 17.4 | 7.1 | 11.0 | 14.4 | 16.6 | 26.0 | 9.1 | 12.9 |

The pharmacokinetic profiles of fusion proteins were compared and evaluated based on Area Under the Curve (AUC), which indicates the exposure level of the drug.

As shown in Table 5, upon comparing DFD4 with DFD13, and DFD6 with DFD73, it was determined that the introduction of the EIRP (SEQ ID NO: 68) sequence resulted in an approximate 10 to 20% increase in AUC value. Comparing DFD9 with DFD4, the introduction of TGLEAV (SEQ ID NO: 69) resulted in an approximate 6-fold increase in AUC value.

In addition, the TGLEAN (SEQ ID NO: 70), G170N, and G174N mutants were designed for the purpose of improving persistence through N-glycosylation at the C-terminus portion of FGF21, which is known to be proteolyzed in vivo at the C-terminus of FGF21. The increase of AUC by N-glycosylation over each of the control substances was verified. In fact, in order to verify the AUC improvement effect by N-glycosylation, comparison was made with DFD6 (E. coli) which is a substance produced in E. coli without glycosylation. Herein, it was found that the DFD6 produced in the human cell line exhibited AUC level which was 3 times or higher than the DFD6 produced by E. coli, indicating that the pharmacokinetic profile was improved by glycosylation.

A180E, a mutation disclosed in a patent of Amgen Co. (WO 2009/149171), was introduced to the mutants in which TGLEAV (SEQ ID NO: 69) or G170N was introduced such as DFD13 and DFD73 to obtain DFD18 and DFD74. Herein, an additional AUC increase by about 2 to 3 fold was found.

To summarize the above results, the introduction of various mutants and combinations thereof resulted in improvement in the pharmacokinetic parameters as compared to the wild-type FGF21 fusion protein DFD9. The fusion protein showing the highest AUC value was DFD74 in which EIRP (SEQ ID NO: 68), G170N and A180E were introduced, showing about 45 times higher AUC than DFD9. Also, it was found that DFD74 shows better drug exposure than RGE of Amgen, considering the administration dose of RGE, i.e, 2 mg/kg. The overall pharmacokinetics-improving effects by the mutation sequences are summarized in Table 6.

TABLE 6

| Mutation sequence | Position of mutation | Control material vs improved material | Assessment of pharmacokinetic parameters |
|---|---|---|---|
| EIRP (SEQ ID NO: 68) | 98-101 | DFD4 vs DFD13 DFD6 vs DFD73 | Improvement of AUC |
| TGLEAV (SEQ ID NO: 69) | 170-174 | DFD9 vs DFD4 | Improvement of AUC |
| TGLEAN (SEQ ID NO: 70) | 170-174 | DFD9 vs DFD5 | Improvement of AUC |
| G170N | 170 | DFD9 vs DFD6 DFD6 (E. coli) vs DFD6 | Improvement of AUC Improvement of AUC |
| G174N | 174 | DFD9 vs DFD7 | Improvement of AUC |
| A180E | 180 | DFD13 vs DFD18 DFD73 vs DFD74 | Improvement of AUC Improvement of AUC |

Experimental Example 4. Activity of Fusion Proteins in Diet-Induced Obesity Mice Experimental Example 4-1. Experimental Method for Evaluating Activities in Diet-Induced Obesity Mice The body weight-reduction effect of DFD18, an FGF21 mutant fusion protein, was evaluated in diet-induced obese mice. For the diet-induced obesity model, C57BL/6J mice were purchased from Central Lab. Animal Inc. and fed on a high-fat diet containing 60 kcal % fat (Research diet) for 8 to 12 weeks. The mice were divided into groups (n=8/group) in order to have a similar mean value of body weight one day before the drug treatment (Day 0), and then 30 nmol/kg of samples were subcutaneously administered once. Subsequently, a single subcutaneous administration at a dose of 30 nmol/kg was performed, followed by the observation of a change in the body weight as compared to phosphate buffered saline (PBS) as a solvent.

Experimental Example 4-2. Protein Activity in Diet-Induced Obesity Mice

Figure 6A:
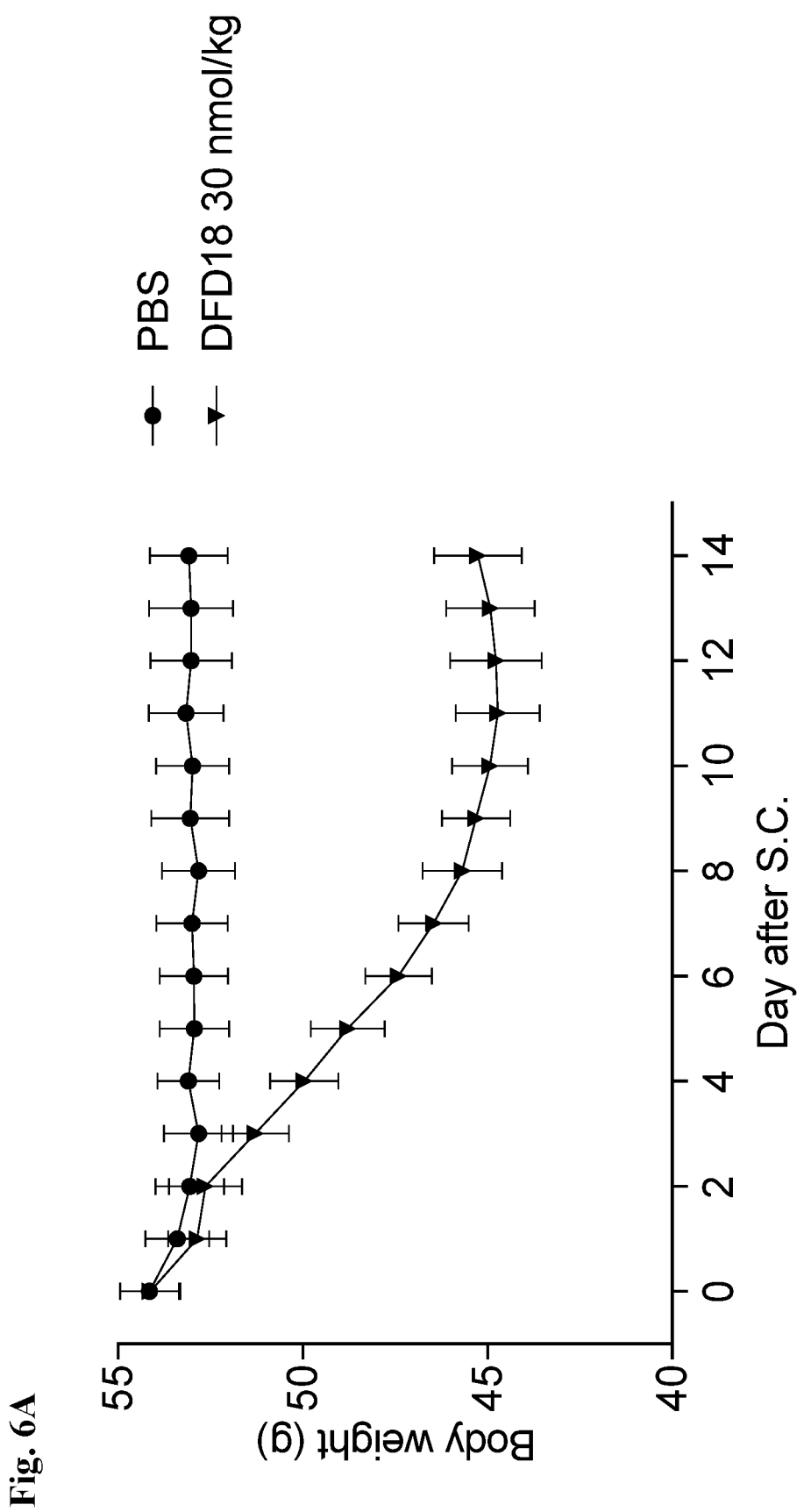
FIG. 6A is a graph showing changes in body weight expressed in a gram unit after single administration of DFD18 in a diet-induced obesity mouse model from the point of administration to day 14. DFD18 showed excellent weight loss effect. The data are indicated as mean values and the standard errors of the means.
Figure 6B:
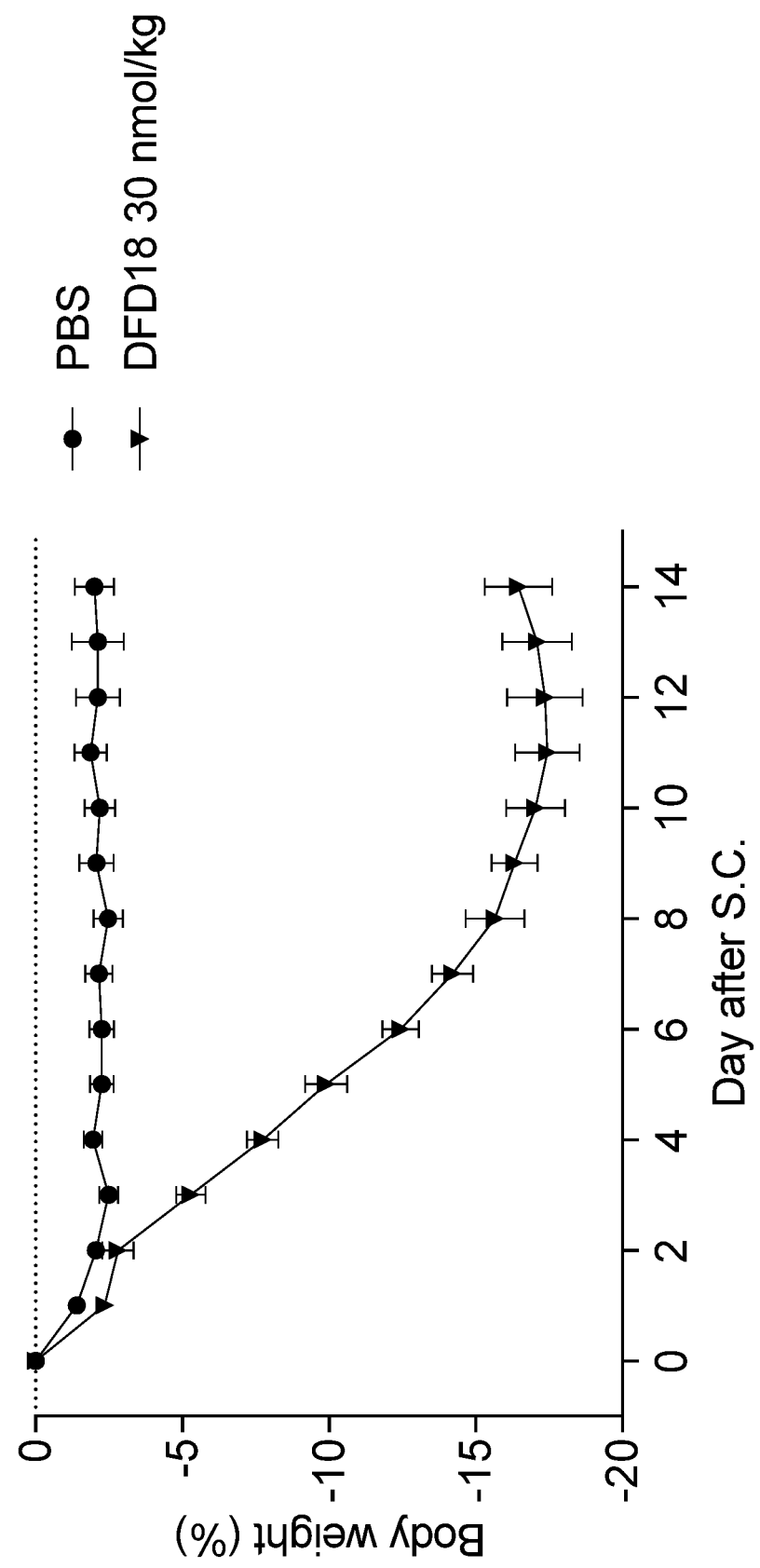
FIG. 6B is a graph showing changes in body weight expressed in a % unit after single administration of DFD18 in a diet-induced obesity mouse model from the point of administration to day 14. DFD18 showed excellent weight loss effect. The data are indicated as mean values and the standard errors of the means.

For changes in body weight over time in the diet-induced obesity mouse model following single administration of 30 nmol/kg DFD18, it was confirmed that the weight-reducing effect was continuing by the $10^{th}$ day after the administration, and the maximum weight reduction (about 18%) was at the $11^{th}$ day after the administration, which was maintained by the $14^{th}$ day (FIGS. 6A and 6B).

Preparation Example 2. Preparation and Purification of Fusion Proteins

Preparation Example 2-1. Preparation of Expression Vectors for Expression of Fusion Proteins In order to identify the effects of the sequence of the GLP-1 mutant protein and the sequence of the Fc hinge fused thereto on the in vitro activity, pharmacokinetic profiles and pharmacological efficacy, various sequences for the Fc-fused GLP-1 mutant proteins were designed. The sequences of the GLP-1 mutant proteins are listed in Table 7 below.

TABLE 7

| SEQ ID NO | Sequence of GLP-1 mutant protein |
|---|---|
| 43 | GLP-1(A2G) |
| 44 | GLP-1(GE) |
| 45 | GLP-1(GG) |
| 46 | GLP-1(GEG) |

Further, the sequences of Fc-fused GLP-1 mutants are listed in Table 8.

TABLE 8

| SEQ ID NO | Fc-fused GLP-1 mutant protein |
|---|---|
| 49 | DFD52: GLP1(A2G)-HyFc5 |
| 50 | DFD53: GLP1(A2G)-HyFc40 |
| 51 | DFD54: GLP1(GE)-HyFc5 |
| 52 | DFD55: GLP1(GE)-HyFc40 |
| 53 | DFD56: GLP1(GG)-HyFc5 |
| 54 | DFD57: GLP1(GG)-HyFc40 |
| 55 | DFD58: GLP1(GEG)-HyFc5 |
| 56 | DFD59: GLP1(GEG)-HyFc40 |

In Table 8, HyFc5 refers to SEQ ID NO: 47, and HyFc40 refers to SEQ ID NO: 48.

In order to investigate the effects of the sequences of the GLP-1 mutant proteins and FGF21 mutant proteins, the sequence of the Fc hinge fused to the GLP-1 mutants, the sequence of the linker connected between the FGF21 mutant proteins and Fc on the in vitro activity, pharmacokinetic profiles and pharmacological efficacy, various sequences for the fusion proteins were designed. The sequences of the fusion proteins including the GLP-1 mutant proteins and FGF21 mutant proteins are listed in Table 9 below. Each fusion protein contains a GLP-1 mutant protein, an Fc region of an immunoglobulin, a linker and an FGF21 mutant protein connected in this order from the N-terminus to C-terminus.

TABLE 9

| SEQ ID NO | Material code | Sequence of GLP-1 mutant protein | Fusion carrier | Linker sequence | Changes in FGF21 sequence |
|---|---|---|---|---|---|
| 58 | DFD23 | GLP-1(A2G) | hyFc40 (SEQ ID NO: 48) | GS3 (SEQ ID NO: 4) | FGF21 (EIRP, (SEQ ID NO: 68), TGLEAV) (SEQ ID NO: 69)) |
| 59 | DFD24 | GLP-1(GE) | hyFc5 (SEQ ID NO: 47) | GS3 (SEQ ID NO: 4) | FGF21 (EIRP, (SEQ ID NO: 68), TGLEAV) (SEQ ID NO: 69)) |
| 60 | DFD25 | GLP-1(GE) | hyFc40 (SEQ ID NO: 48) | GS3 (SEQ ID NO: 4) | FGF21 (EIRP, (SEQ ID NO: 68), TGLEAV) (SEQ ID NO: 69)) |
| 61 | DFD26 | GLP-1(GG) | hyFc5 (SEQ ID NO: 47) | GS3 (SEQ ID NO: 4) | FGF21 (EIRP, (SEQ ID NO: 68), TGLEAV) (SEQ ID NO: 69)) |
| 62 | DFD27 | GLP-1(GG) | hyFc40 (SEQ ID NO: 48) | GS3 (SEQ ID NO: 4) | FGF21 (EIRP (SEQ ID NO: 68), TGLEAV (SEQ ID NO: 69)) |
| 63 | DFD28 | GLP-1(GEG) | hyFc5 (SEQ ID NO: 47) | GS3 (SEQ ID NO: 4) | FGF21 (EIRP (SEQ ID NO: 68), TGLEAV (SEQ ID NO: 69)) |
| 64 | DFD29 | GLP-1(GEG) | hyFc40 (SEQ ID NO: 48) | GS3 (SEQ ID NO: 4) | FGF21 (EIRP (SEQ ID NO: 68), TGLEAV (SEQ ID NO: 69)) |
| 65 | DFD69 | GLP-1(GEG) | hyFc40 (SEQ ID NO: 48) | GS3 (SEQ ID NO: 4) | FGF21(EIRP (SEQ ID NO: 68), TGLEAV (SEQ ID NO: 69), A180E) |
| 66 | DFD112 | GLP-1(GEG) | hyFc40 (SEQ ID NO: 48) | GS3 (SEQ ID NO: 4) | FGF21(EIRP (SEQ ID NO: 68), TGLEAN (SEQ ID NO: 70), A180E) |
| 67 | DFD114 | GLP-1(GEG) | hyFc40 (SEQ ID NO: 48) | GS3 (SEQ ID NO: 4) | FGF21(EIRP (SEQ ID NO: 68), G170N, A180E) |

Specifically, the nucleotide sequences encoding each of the fusion proteins were synthesized after consulting with Bioneer Corporation (Korea) based on the amino acid sequence of each protein. NheI and NotI restriction enzyme sequences were added to the 5' terminus and 3' terminus of the nucleotide sequences encoding each of the fusion proteins and an initiation codon for protein translation and a leader sequence (MDAMLRGLCCVLLLCGAVFVSPSHA) (SEQ ID NO: 83) enabling secretion of the expressed protein to the outside of a cell were inserted next to the restriction enzyme sequence at the 5' terminus. A termination codon was inserted next to the nucleotide sequence, which encodes each of the fusion proteins. The nucleotide sequence encoding each of the fusion proteins was cloned into a pTrans-empty expression vector by using the two restriction enzymes NheI and NotI. The pTrans-empty expression vector, which has a simple structure including a CMV promoter, a pUC-derived replication origin, an SV40-derived replication origin and an ampicillin-resistance gene, was purchased from CEVEC Pharmaceuticals (Germany).

Preparation Example 2-2. Construction of Plasmid DNA for Expression of Fc-Fused GLP-1 Mutant and Fusion Proteins E. coli was transformed with each of the expression vectors constructed in Preparation Example 2-1 to obtain a large quantity of plasmid DNA to be used for expression. E. coli cells, with cell walls weakened through heat shock, were transformed with each expression vector, and the transformants were plated out on an LB plate to obtain colonies. The colonies thus obtained were inoculated into LB media, cultured at 37° C. for 16 hours, and each E. coli culture containing each expression vector was obtained in a volume of 100 mL. The E. coli thereafter obtained was centrifuged to remove the culture medium, and then P1, P2, P3 solutions (QIAGEN, Cat No.:12963) were added to break the cell walls, thereby obtaining a DNA suspension in which proteins and DNA were separated. Plasmid DNA was purified from the DNA suspension thus obtained by using a QIAGEN™ DNA purification column. The eluted plasmid DNA was identified by agarose gel electrophoresis, and the concentrations and purities were measured using a NANO-DROP™ device (Thermo Scientific, NANODROP LITE™). The DNA thus obtained was used for expression.

Preparation Example 2-3. Expression of Fc-Fused GLP-1 Mutants and Fusion Proteins in CAP-T Cells Human cell lines were transformed with each plasmid DNA obtained in Preparation Example 2-2. Each plasmid DNA type was transduced into CAP-T cells (CEVEC), which had been cultured in PEM medium (Life Technologies), by using a PEI solution (Polyplus, Cat. No.:101-10N). The mixed solution of DNA and the PEI solution was mixed with the cell suspension using Freestyle293 expression medium (Invitrogen), cultured at 37° C. for 5 hours, and PEM medium was added. After culturing at 37° C. for 5-7 days, the culture was centrifuged to remove cells and supernatant containing each protein was obtained.

Preparation Example 2-4. Purification of Fc-Fused GLP-1 Mutants and Fusion Proteins Protein A affinity chromatography column (GE Healthcare) was equilibrated with 1×PBS buffer solution (pH 7.4). The culture supernatant including each of the Fc-fused GLP-1 mutants and fusion proteins obtained in Preparation Example 2-3 was filtered with a 0.2 μm filter, and then loaded into a Protein A affinity chromatography column. The column was washed with 1×PBS buffer solution (pH 7.4) and then the proteins were eluted using 100 mM glycine buffer solution (pH 3.0). The proteins obtained by affinity chromatography were purified using an anion exchange resin column (POROS® HQ 50 μm, Thermo Fisher Scientific). The anion exchange resin column was equilibrated with 50 mM Tris buffer solution (pH 8.0), before the proteins eluted from the affinity chromatography were loaded thereto.

After washing the column with 50 mM Tris buffer solution (pH 8.0), 50 mM Tris buffer solution (pH 8.0) was dispensed along the concentration gradient and the eluted fractions were analyzed. Each eluted fraction was analyzed by using size exclusion chromatography (SEC-HPLC), and the fractions including the Fc-fused GLP-1 mutants and fusion proteins with high purity were collected and dialyzed overnight at 4° C. using a final buffer solution (1×PBS, 1 mM EDTA, pH 7.4). Upon completion of the dialysis, the obtained protein stock solution was concentrated at 3,000 rpm using a 30,000 MW cut-off centrifugation filter at 4° C. The concentration of each protein was measured via BCA quantitative analysis.

Experimental Example 5. In Vitro Activity of Fusion Proteins

Experimental Example 5-1. Activity of DFD23, DFD24, DFD25, DFD26, DFD27, DFD28 and DFD29

The in vitro GLP-1 activities of the fusion proteins DFD23, DFD24, DFD25, DFD26, DFD27, DFD28 and DFD29 were measured. Specifically, a CHO cell line (Eurofins, HTS163C2), overexpressing the human GLP-1 receptor was purchased and used to evaluate the GLP-1 activities of the fusion proteins. For the evaluation of activity, samples containing the fusion proteins (protein stock solutions prepared in Preparation Example 2-4; hereinafter, "sample") were subjected to a 4-fold serial dilution at a concentration of 25 nM. After the human GLP-1 receptor-overexpressing CHO cell line was treated for 30 minutes, the intracellular cAMP produced was measured (Cisbio, 62AM4PEB). The activity of each protein was evaluated by comparing the $EC_{50}$ values.

Figure 7:
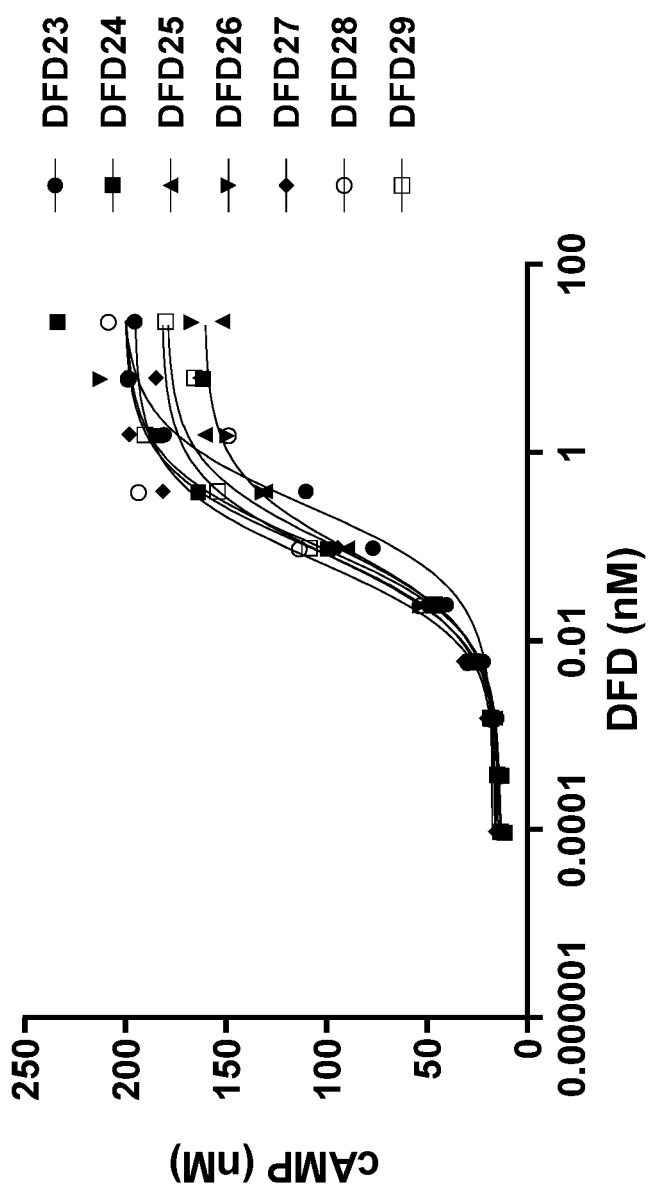
FIG. 7 is a graph showing the in vitro GLP-1 activities of fusion proteins depending on the hinges which link the C-terminus of GLP-1 mutants and GLP-1 to the Fc region using a CHO cell line in which human GLP-1 receptor is overexpressed. Generally, the fusion protein including a GLP-1 (A2G) sequence (DFD23) exhibited 2 to 3 times lower activity than those of other fusion proteins including other GLP-1 mutant sequences. No significant difference in GLP-1 activities was shown between the fusion proteins including mutant sequences other than GLP-1 (A2G) sequence.

As shown in FIG. 7, the fusion protein containing the GLP-1 (A2G) sequence showed activity approximately 2~3 times lower than that for the fusion proteins containing other GLP-1 mutant sequences. No significant difference in GLP-1 activities was observed between the fusion proteins containing the mutation sequences except the GLP-1 (A2G) sequence.

Experimental Example 5-2. Activities of DFD59, DFD69, DFD112 and DFD114

The in vitro GLP-1 activities of the fusion proteins DFD69, DFD112 and DFD114 prepared in Preparation Example 2 and DFD59 (an Fc-fused GLP-1 mutant) were measured. Specifically, a CHO cell line (Eurofins, HTS163C2) overexpressing the human GLP-1 receptor was purchased and used to evaluate the GLP-1 activities of the fusion proteins. For the evaluation of activity, the sample containing each of the fusion proteins was subjected to a 4-fold serial dilution at a concentration of 25 nM. After the human GLP-1 receptor-overexpressing CHO cell line was treated for 30 minutes, the intracellular cAMP produced was measured (Cisbio, 62AM4PEB).

Figure 8A:
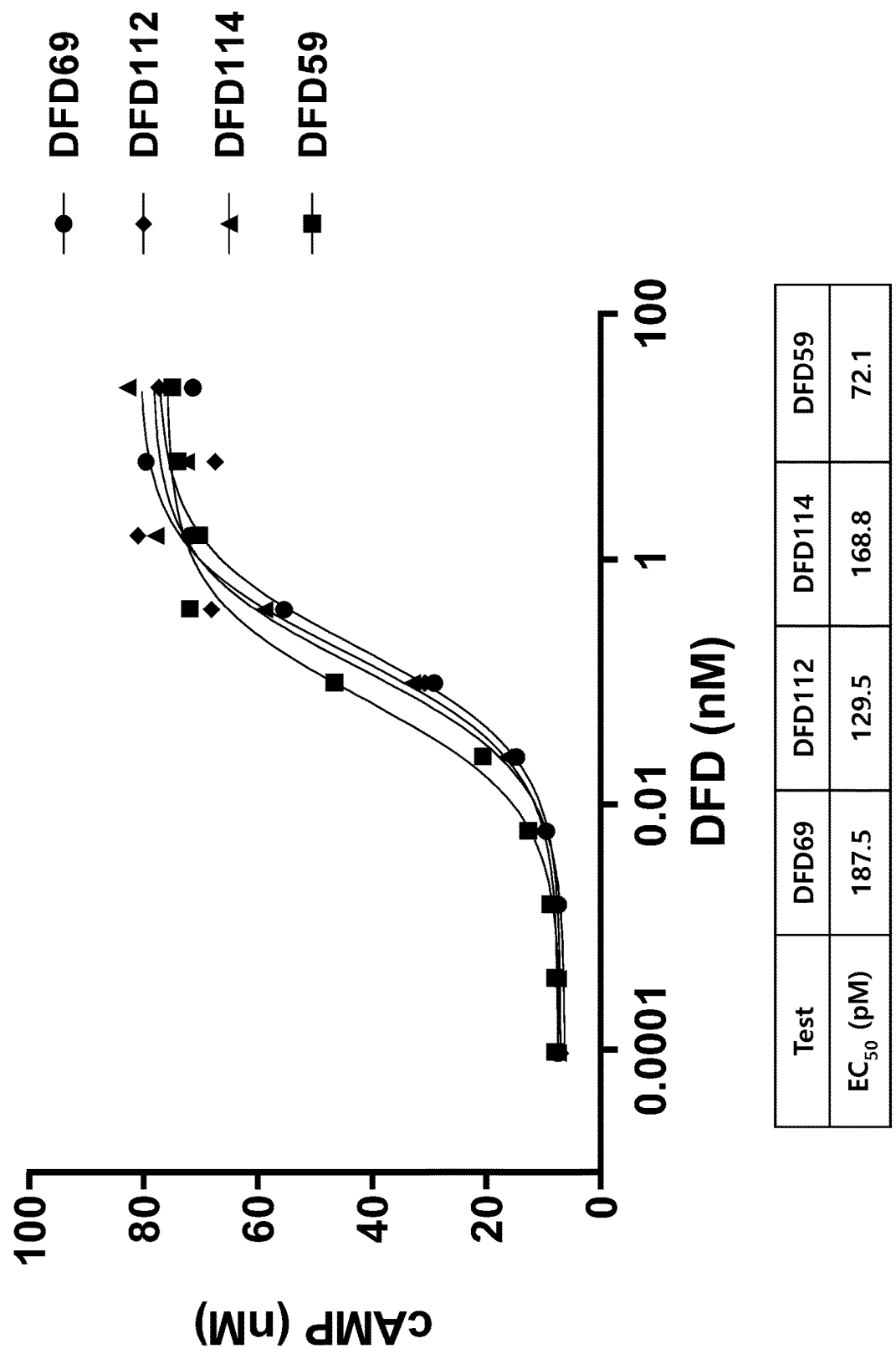
FIG. 8A is a graph showing the GLP-1 activities of DFD59, DFD69, DFD112 and DFD114. In vitro GLP-1 activities of three fusion proteins (DFD69, DFD112 and DFD114) and Fc-fused GLP-1 mutant including no FGF21 were measured using a CHO cell line in which human GLP-1 receptor is overexpressed. The three fusion proteins showed similar $EC_{50}$ values, and the Fc-fused GLP-1 mutant (DFD59) showed about 2 times higher activity than those of fusion proteins.
Figure 8B:
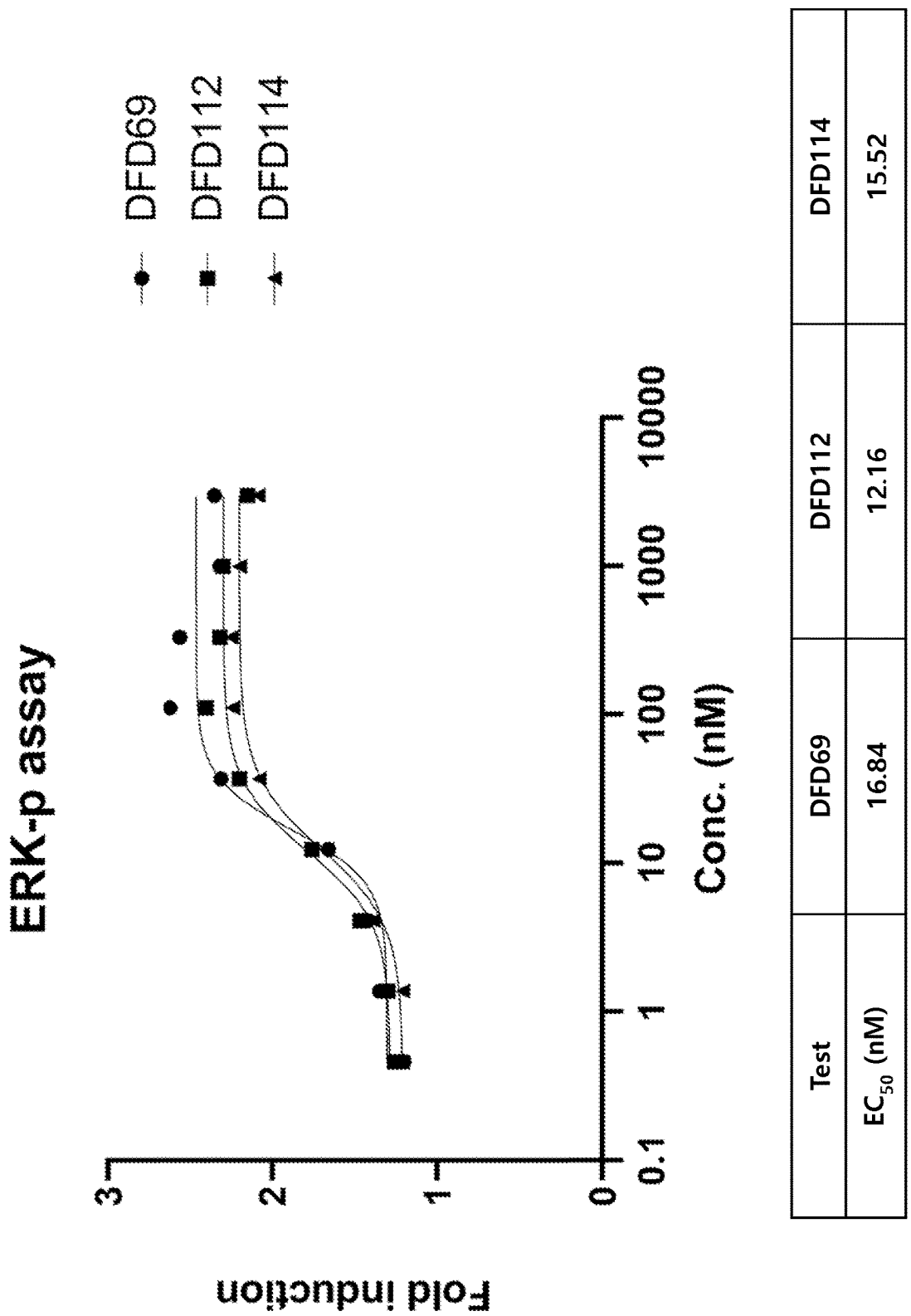
FIG. 8B is a graph showing the FGF21 activity of DFD69, DFD112, and DFD114. In vitro activities of fusion proteins depending on FGF21 mutants were measured using a HEK293 cell line in which human β-klotho is overexpressed. It was verified that the in vitro activities of the FGF21 portion were similar in the three fusion proteins.

As shown in FIGS. 8A and 8B, the activity of each protein was evaluated by comparing the $EC_{50}$ value. The three fusion proteins showed similar $EC_{50}$ values, and DFD59 (containing no FGF21 mutant) showed activity approximately 2 times higher than that of the fusion proteins.

Next, the in vitro activities of the FGF21 portion in DFD69, DFD112 and DFD114 were measured. Specifically, the in vitro activities of the FGF21 portion in the fusion proteins were evaluated using a HEK293 cell line overexpressing human β-klotho (a co-receptor of FGF21). For the evaluation of activity, samples containing each of the fusion proteins were subjected to a 3-fold serial dilution at a concentration of 3 μM. After having been cultured in a serum-deficient state for 5 hours, the human β-klotho-overexpressing HEK293 cell line was treated for 20 minutes, before the cells were lysed by adding cytolysis buffer (Cisbio/Cat #64ERKPEG) with stirring at 60 rpm for 30 minutes at room temperature. The cell lysate solution was mixed with antibodies which can detect ERK and phosphorylated ERK, and the mixture was maintained at room temperature for 2 hours. Fluorescence was detected using a fluorometric detector (TECAN/GENiosPro). The activities were measured by comparing their $EC_{50}$ values.

It was confirmed that the in vitro activities of the FGF21 portion of the fusion proteins DFD69, DFD112 and DFD114 were similar, as shown in FIGS. 8A and 8B.

Experimental Example 6. Pharmacokinetic Assessment of Fusion Proteins

Experimental Example 6-1. Experimental Method for Pharmacokinetic Assessment Six-week old male ICR mice purchased from Orient BIO (Korea) were divided into groups (n=3/blood sampling time) in order to have a similar mean value of body weight one day before drug treatment, and subcutaneously administered once with a respective sample in a volume of 1 mg/kg. The blood samples were collected at 1, 4, 8, 12, 24, 48, 72, 96, 144, 192 and 240 hours after the injection, respectively. The concentration of each fusion protein in the blood was measured based on the FGF21 portion and the GLP-1-Fc portion separately. The concentration of the intact full length FGF21 portion of the fusion protein in the blood was measured using an Intact human FGF21 ELISA Kit (F1231-K01, Eagle Biosciences, USA), which has immunoreactivity to the N-terminus and C-terminus of FGF21 protein. Further, the concentration of the active GLP-1-Fc portion of the fusion protein in the blood was measured using an antibody, which has immunoreactivity to the N-terminus of GLP-1 and Fc, as determined through ELISA analysis. The concentrations of the FGF21 and GLP-1-Fc portions of each protein in the blood samples collected until 240 hours after single subcutaneous injection of each protein into the mice were measured, and the pharmacokinetic parameters of each protein was calculated.

Experimental Example 6-2. Pharmacokinetic Activity Results

Figure 9A:
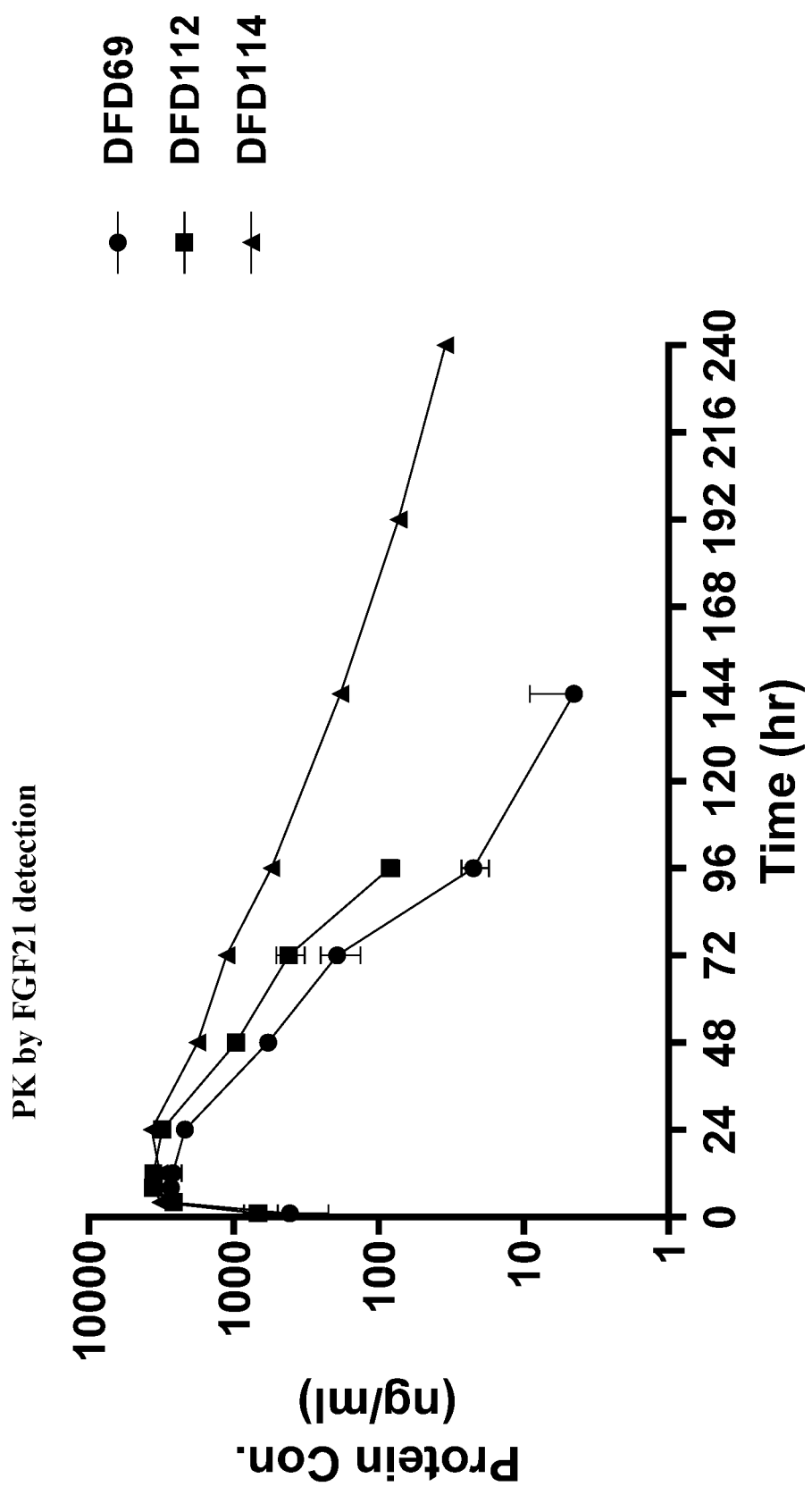
FIG. 9A is a graph showing serum drug concentrations over time after subcutaneous administration, of FGF21 portion of the fusion proteins DFD69, DFD112, and DFD114. The data are indicated as mean values and the standard deviation.
Figure 9B:
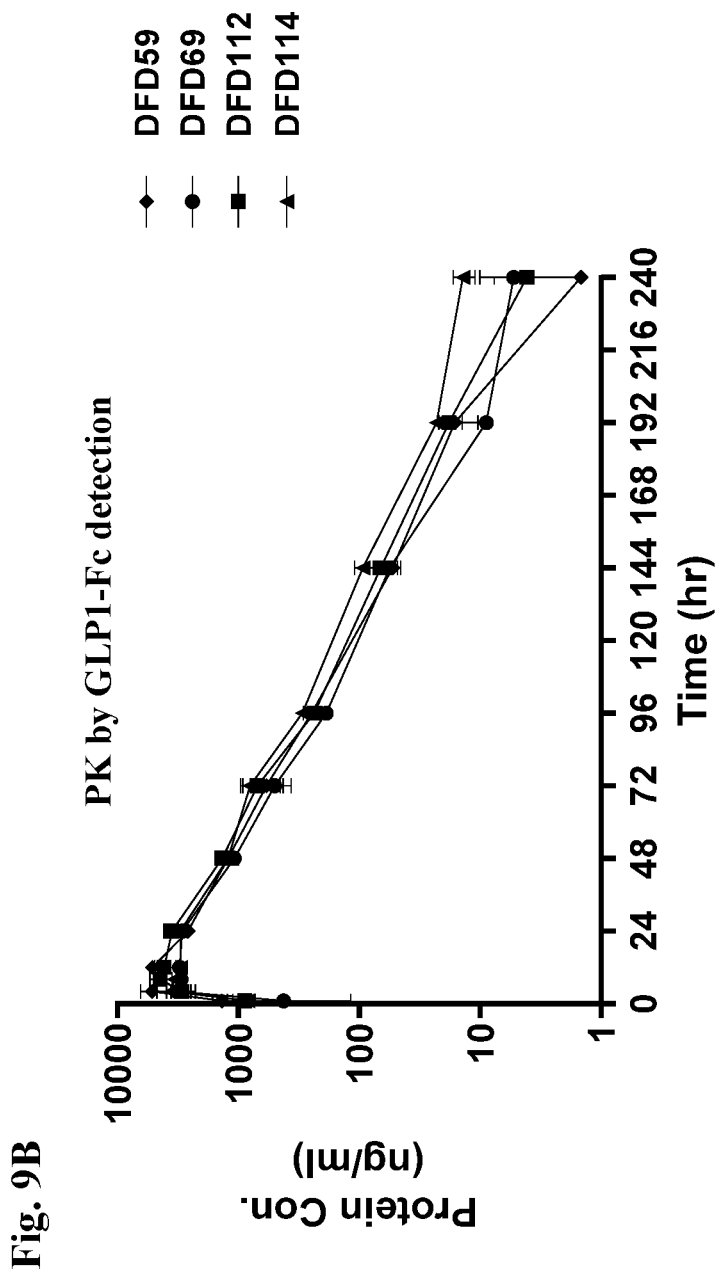
FIG. 9B is a graph showing serum drug concentrations over time after subcutaneous administration, of GLP-1 portion of the fusion proteins DFD59, DFD69, DFD112, and DFD114. The data are indicated as mean values and the standard deviation.

Based on the concentration of each active substance in the blood over time after single subcutaneous administration of each protein in mice (FIGS. 9A and 9B), pharmacokinetic parameters for the FGF21 and GLP-1-Fc portions of the fusion proteins were calculated. The data are shown in Table 10 below.

TABLE 10

| Parameters | FGF21 detection | | | GLP1-Fc detection | | | |
| --- | --- | --- | --- | --- | --- | --- | --- |
| | DFD69 | DFD112 | DFD114 | DFD59 | DFD69 | DFD112 | DFD114 |
| Tmax (Hour) | 8 | 8 | 24 | 4 | 4 | 8 | 4 |
| Cmax (ng/ml) | 2715 | 3619 | 3711 | 5202.1 | 3234 | 4454 | 3616 |
| AUClast (ng · hr/ml) | 100907 | 144395 | 222504 | 182852 | 149083 | 189338 | 171687 |
| Half-life (Hour) | 13.4 | 14.2 | 39.9 | 20.7 | 23.3 | 24.7 | 27.2 |

The pharmacokinetic profile of each fusion protein was compared and evaluated based on Area Under the Curve (AUC), which indicates the exposure level of the drug.

As shown in Table 10, for the pharmacokinetic parameters of the FGF21 portion, DFD114 showed the highest degree of drug exposure (AUC) and half-life, and DFD112 showed the next highest AUC value, followed by DFD69. DFD114 exhibited an approximate 2-fold or higher increase in AUC value as compared with DFD69. For the pharmacokinetics of the GLP-1-Fc portion, the four proteins (DFD59, DFD69, DFD112 and DFD114) containing the same GLP-1 mutant sequence showed similar AUC values.

Experimental Example 7. Evaluation of Fusion Protein Activity on Non-Alcoholic Steatohepatitis in Diet-Induced Obesity Mice Experimental Example 7-1. Evaluation Method of Activity on Non-Alcoholic Steatohepatitis in Diet-Induced Obesity Mice The steatohepatitis- and lipid-improving effects of the fusion proteins DFD114 and DFD112, and FGF21 mutant fusion proteins DFD74 and DFD72 were evaluated in a diet-induced obesity mouse model.

In order to induce diet-induced obesity, C57BL/6J mice were fed with a high fat diet (Research diet) containing 60 kcal % fat for about 37 weeks to prepare an obesity mouse model having steatohepatitis. The mice were divided into groups (n=6/group) such that the average body weights were similar at one day prior to the drug treatment. Thereafter, DFD114, DFD112, DFD74 and DFD72 were administered 3 times at a dose of 3 or 10 nmol/kg at 4 day interval for 2 weeks.

The control group was subcutaneously administered with the solvent (Dulbecco's phosphate buffered saline, DPBS, Gibco, USA) used for the preparation of the test drug, by the same method. 4 days after the last administration, animals were fasted overnight and blood was collected from the postcaval vein and liver tissues were extracted after inhalation anesthesia and laparotomy. Blood biochemical tests were performed with serum samples isolated from the collected blood samples, and the fixed liver tissues were prepared as specimens through trimming, dehydration, paraffin embedding, slicing, etc. And the prepared specimens were stained with hematoxylin and eosin (H&E), and histopathological changes were observed using an optical microscope (Olympus, ECLIPSE™ E600).

Experimental Example 7-2. Activity Evaluation Results on Non-Alcoholic Steatohepatitis in Diet-Induced Obesity Mice In order to evaluate the steatohepatitis- and lipid-improving effects of fusion proteins and the FGF21 mutant fusion protein, DFD114, DFD112, DFD74 and DFD72 were repeatedly administered at a dose of 3 or 10 nmol/kg at 4 day interval for 2 weeks in a diet-induced obesity mouse model. Then, the lipid changes in serum and the liver tissue were analyzed, and histopathological changes were observed.

Figure 10A:
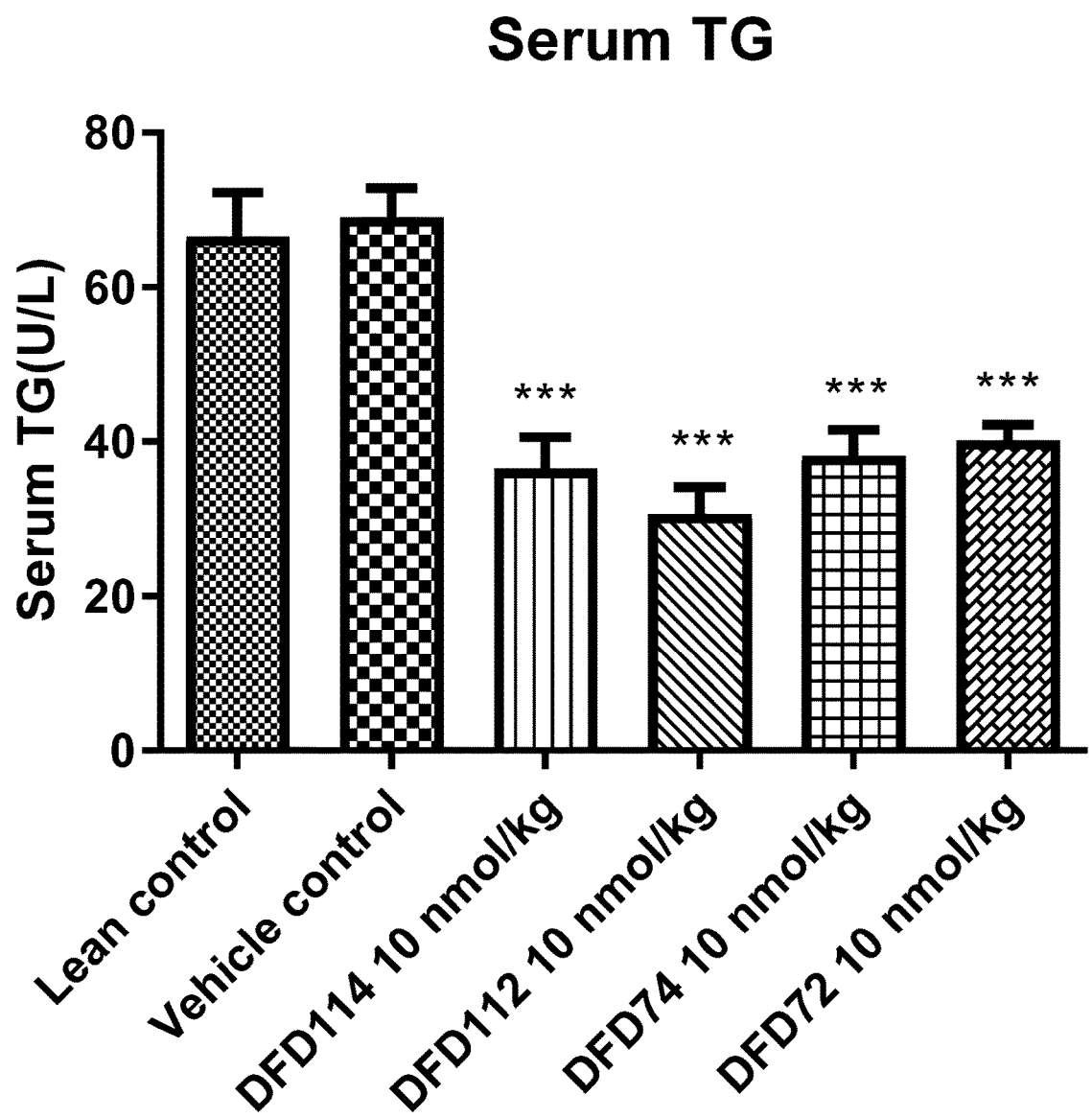
FIG. 10A is a graph showing changes in serum triglyceride (TG) after repeated subcutaneous administration of DFD114, DFD112, DFD74 or DFD72 in a diet-induced obesity mouse model at the interval of 4 days for 2 weeks. The administration of the fusion protein and the FGF21 mutant fusion protein showed serum lipid-lowering effects as compared to the control group. The data are indicated as mean values and the standard errors of the means. Statistical analysis was performed by Dunnet's multiple comparison test after one-way ANOVA (***: $P<0.001$ vs. vehicle control).
Figure 10B:
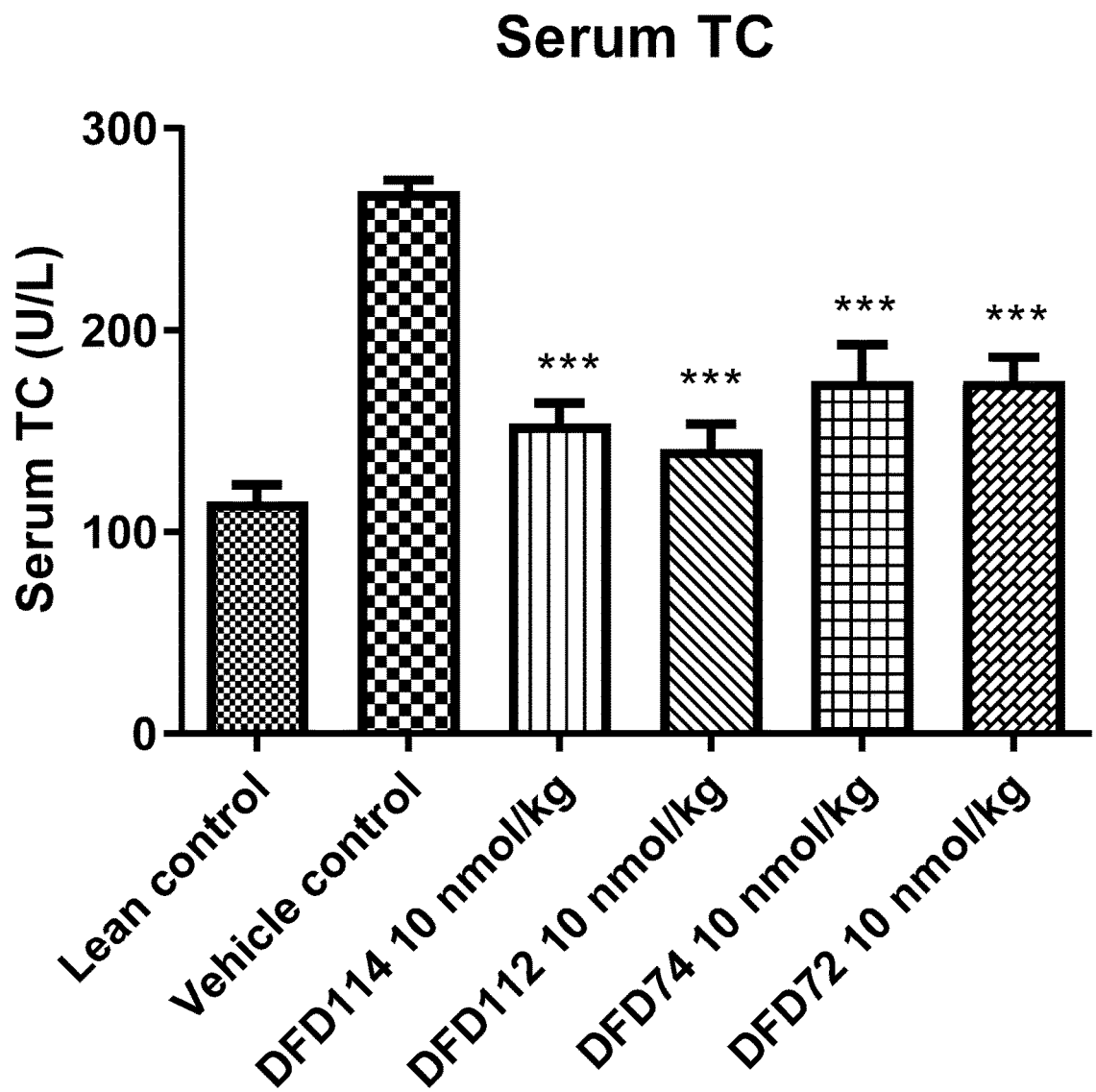
FIG. 10B is a graph showing changes in serum total cholesterol (TC) after repeated subcutaneous administration of DFD114, DFD112, DFD74 or DFD72 in a diet-induced obesity mouse model at the interval of 4 days for 2 weeks. The administration of the fusion protein and the FGF21 mutant fusion protein showed serum lipid-lowering effects as compared to the control group (***: $P<0.001$ vs. vehicle control).
Figure 10C:
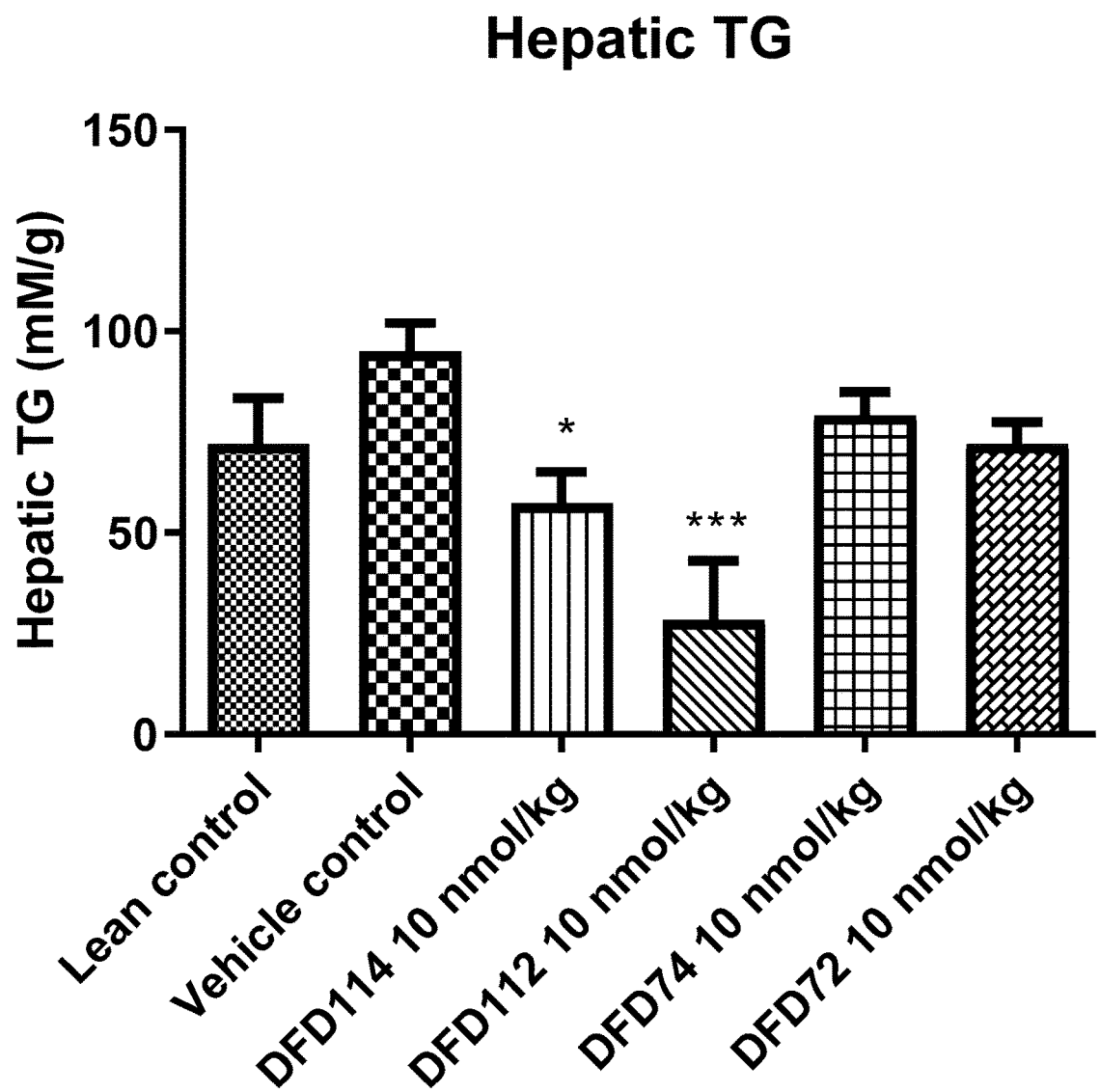
FIG. 10C is a graph showing changes in triglyceride (TG) in the liver after repeated subcutaneous administration of DFD114, DFD112, DFD74 or DFD72 in a diet-induced obesity mouse model at the interval of 4 days for 2 weeks. The administration of FGF21 mutant fusion protein showed lipid-lowering effects in the liver as compared to the control group (*: $P<0.05$, ***: $P<0.001$ vs. vehicle control).

As shown in FIGS. 10A to 10C, triglyceride (TG) and total cholesterol (TC) in serum were measured after repeated subcutaneous administration of the fusion proteins DFD114 and DFD112, and FGF21 mutant fusion proteins DFD74 and DFD72. As a result, the serum triglyceride and total cholesterol levels were decreased, and the triglyceride levels in the liver tissue were also decreased as compared to the vehicle control group.

Figure 11:
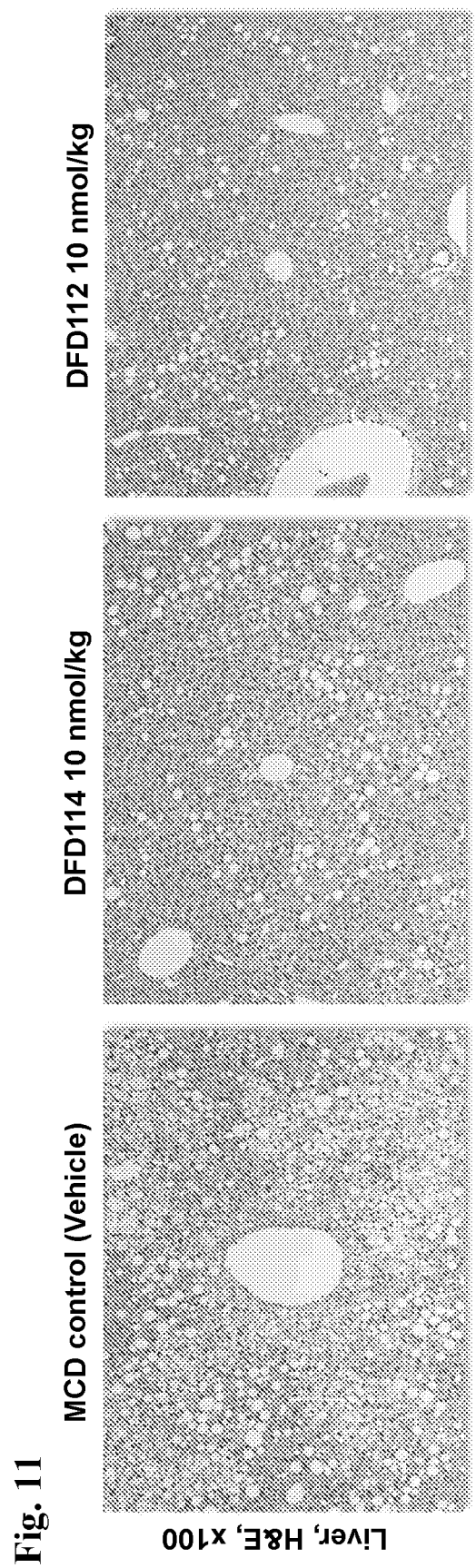
FIG. 11 shows histopathological photographs of the liver obtained by repeated subcutaneous administration of DFD114 or DFD112 in a diet-induced obesity mouse model at the interval of 4 days for 2 weeks. The administration of a fusion protein showed hepatic steatosis-lowering effect as compared to the control group.

As shown in FIG. 11, histopathological examination performed after repeated subcutaneous administration of the fusion proteins DFD114 and DFD112 showed that the lipid in the liver tissue was significantly decreased as compared to the vehicle control group.

Experimental Example 8. Activity Evaluation of Fusion Proteins in MCD-Induced Non-Alcoholic Steatohepatitis Mice Experimental Example 8-1. Activity Evaluation Method in MCD-Induced Non-Alcoholic Steatohepatitis Mice In order to evaluate the inflammation- and fibrosis-reduction effects of fusion proteins and FGF21 mutant fusion proteins in a non-alcoholic steatohepatitis model, the effects of DFD112 and DFD72 in the MCD model were evaluated.

Methionine choline deficient (MCD) diet-induced non-alcoholic liver disease animal model is one of the widely used models for the evaluation of non-alcoholic steatohepatitis. Steatohepatitis with liver fibrosis was induced by feeding the diets lacking methionine and choline, which play important roles in beta-oxidation and very low density lipoprotein (VLDL) synthesis. This is known to be similar to the human steatohepatitis pathology model. In order to induce the steatohepatitis model, MCD diet and methionine choline standard (MCS) diet was freely provided alternatively for 17 weeks by the way of feeding C57BL/6 with MCD diet for 10 days and then MCS diet for 4 days.

The animals were weighed before administration of the test substance, and randomly assigned into groups such that the average body weight of each group was distributed as evenly as possible. After 10 mice were assigned to each group, 3, 10 and 30 nmol/kg of DFD112 and 10 nmol/kg of DFD72 were subcutaneously administered at 2 day interval for 4 weeks. In MSC control group and MCD diet control group, the mice were subcutaneously administered with the solvent (Dulbecco's phosphate buffered saline, DPBS, Gibco, USA) used for the preparation of the test substance, at 2 day interval for 4 weeks by the same method.

After repeated administration of the test substance for 4 weeks, the mice were fasted overnight and blood was collected from the postcaval vein and liver tissues were extracted after inhalation anesthesia and laparotomy. Blood biochemical tests were performed with serum samples isolated from the collected blood samples, and the fixed liver tissues were prepared as specimens through general tissue treatment processes. Then, hematoxylin and eosin (H&E) and immunohistochemical staining were performed, and histopathological changes were observed using an optical microscope (Olympus, BX53™).

Experimental Example 8-2. Activity Evaluation Results in MCD-Induced Non-Alcoholic Steatohepatitis Mice 3, 10 and 30 nmol/kg of the fusion protein DFD112 and 10 nmol/kg of the FGF21 mutant fusion protein DFD72 were repeatedly administered at 2 day interval for 4 weeks to MCD-induced non-alcoholic steatohepatitis mice. Then, blood biochemical examination and histopathological examination were performed to evaluate the effects on non-alcoholic steatohepatitis.

Figure 12A:
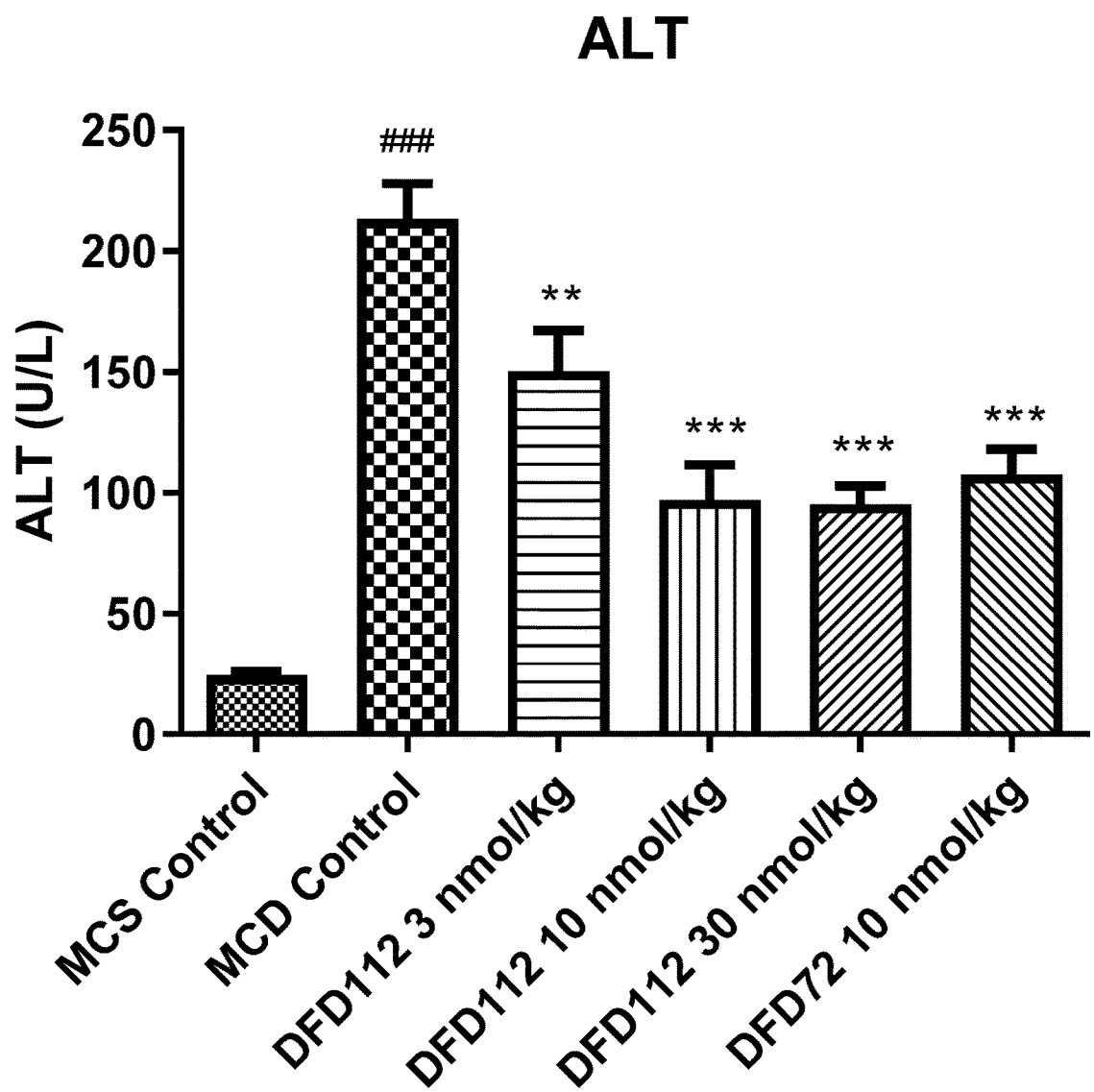
FIG. 12A is a graph showing changes in ALT levels after repeated subcutaneous administration of DFD112 and DFD72 at the interval of 2 days for 4 weeks in a methionine choline deficient (MCD) diet-induced non-alcoholic steatohepatitis mouse model. ALT levels were decreased in a dose dependent manner in the fusion protein-treated groups as compared to the control group, and ALT levels were decreased in the FGF21 mutant fusion protein-treated group as well. The data are indicated as mean values and the standard errors of the means. Statistical analysis was performed by Dunnet's multiple comparison test after one-way ANOVA (###: $P<0.001$ vs. MCS control, : $P<0.01$, *: $P<0.001$ vs. MCD control).
Figure 12B:
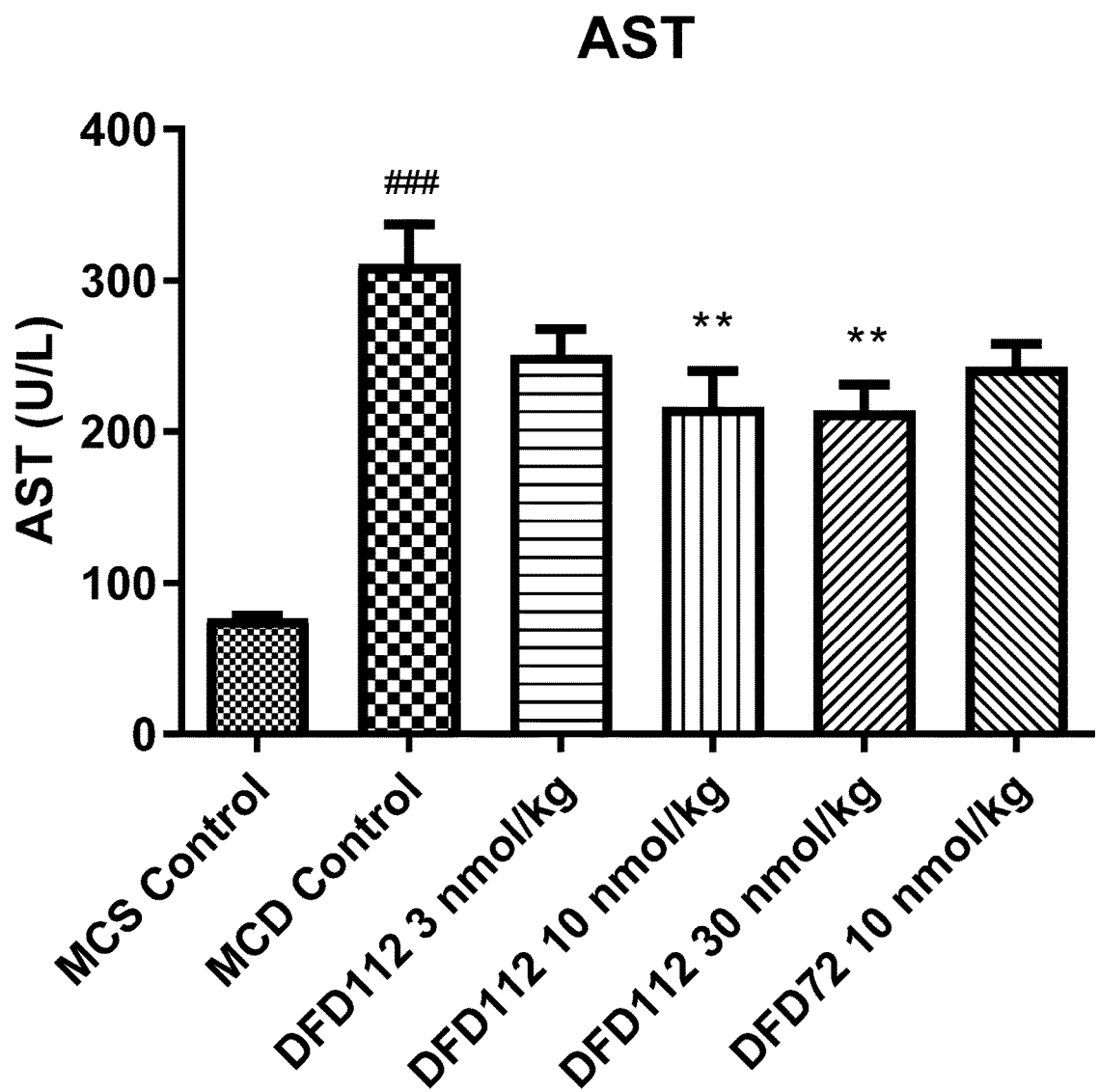
FIG. 12B is a graph showing changes in AST levels after repeated subcutaneous administration of DFD112 and DFD72 at the interval of 2 days for 4 weeks in a methionine choline deficient (MCD) diet-induced non-alcoholic steatohepatitis mouse model. AST levels were decreased in a dose dependent manner in the fusion protein-treated groups as compared to the control group, and AST levels were decreased in the FGF21 mutant fusion protein-treated group as well (###: $P<0.001$ vs. MCS control, **: $P<0.01$ vs. MCD control).
Figure 12C:
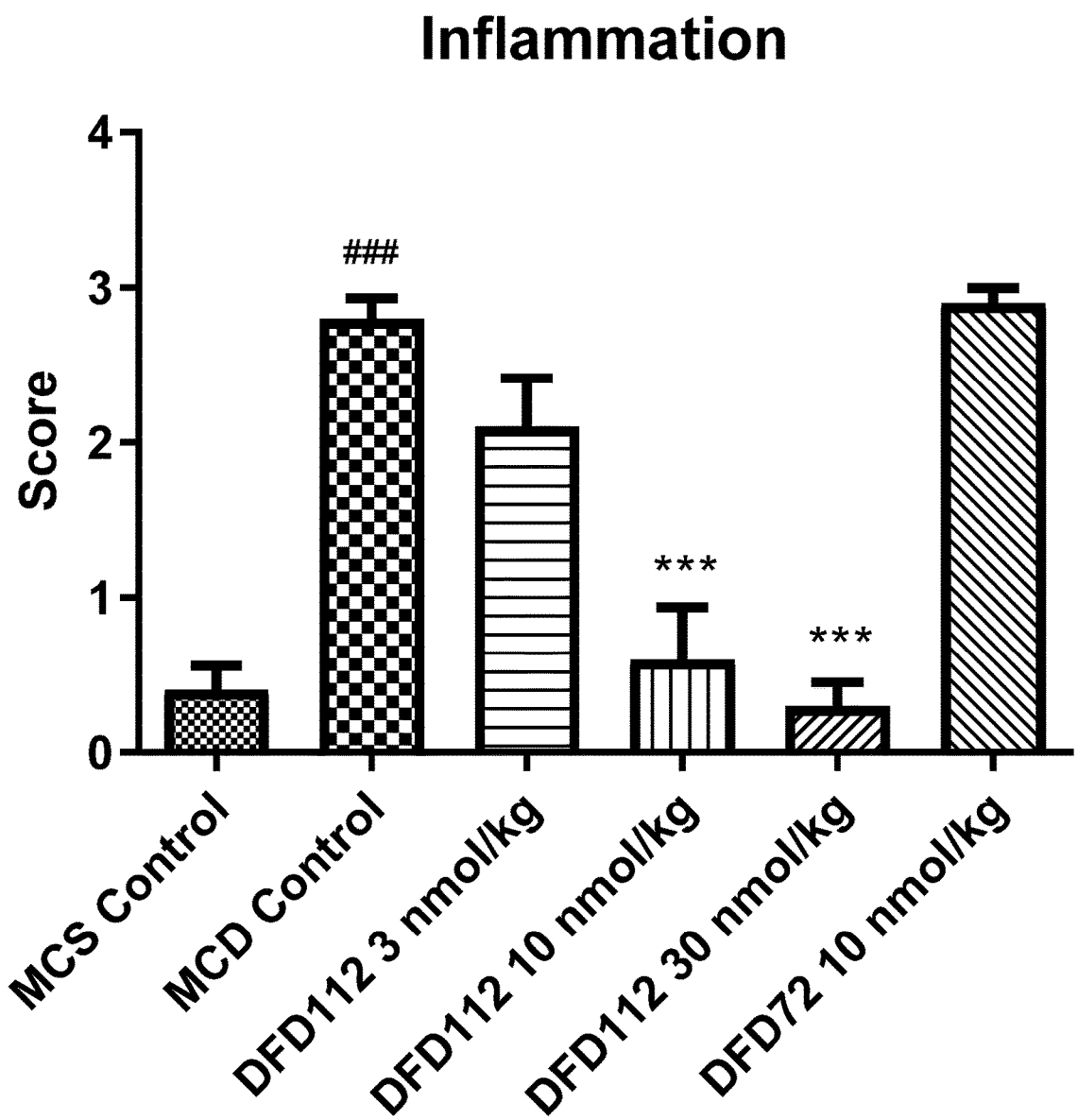
FIG. 12C is a graph showing changes in inflammation levels after repeated subcutaneous administration of DFD112 and DFD72 at the interval of 2 days for 4 weeks in a methionine choline deficient (MCD) diet-induced non-alcoholic steatohepatitis mouse model. Inflammation levels were decreased in a dose dependent manner in the fusion protein-treated groups as compared to the control group, and inflammation levels were decreased in the FGF21 mutant fusion protein-treated group as well (###: $P<0.001$ vs. MCS control, ***: $P<0.001$ vs. MCD control).
Figure 13A:
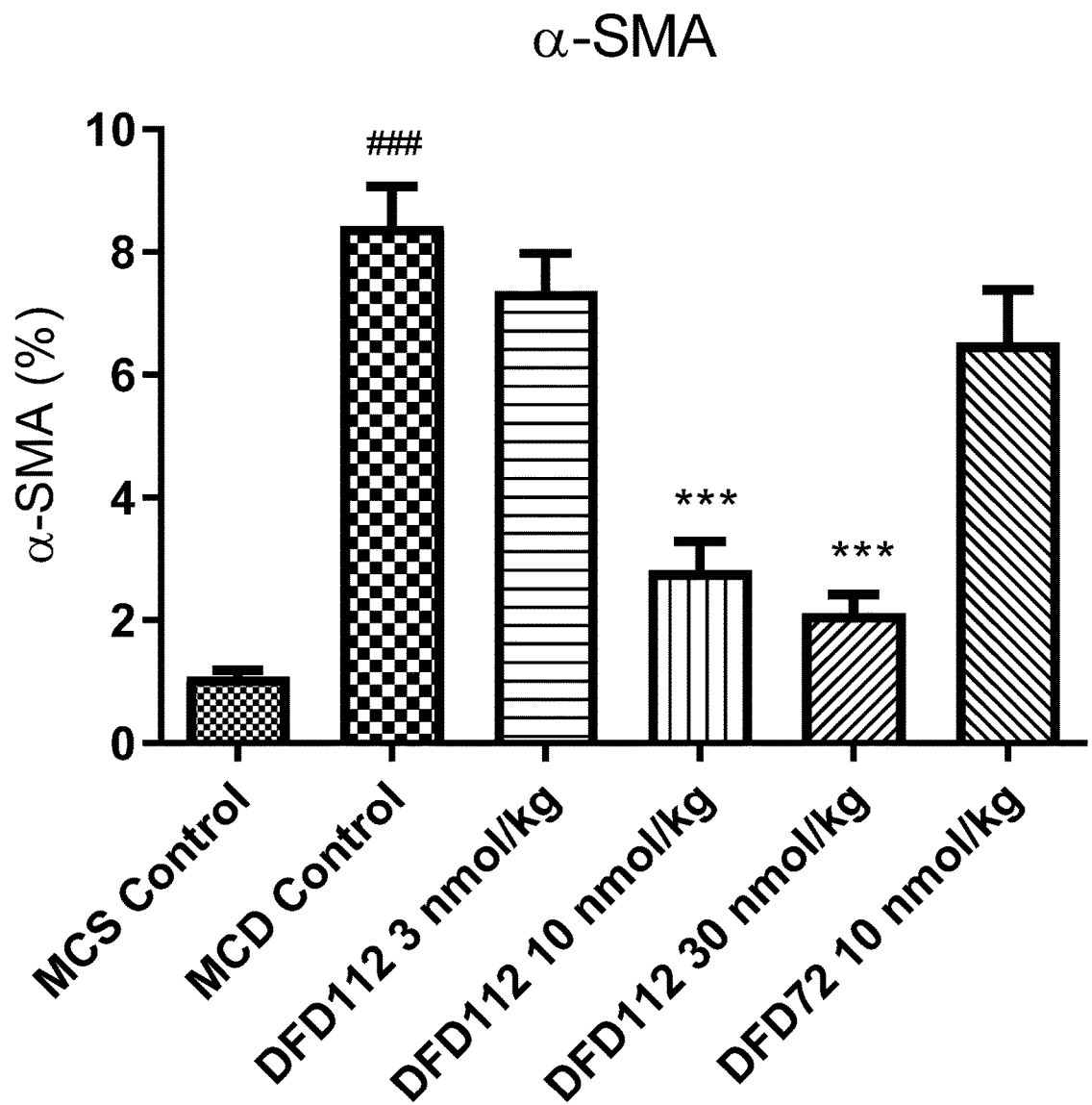
FIG. 13A is a graph showing changes in alpha smooth muscle actin (α-SMA), a fibrosis-related indicator in the liver, after repeated subcutaneous administration of DFD112 and DFD72 at the interval of 2 days for 4 weeks in a MCD diet-induced non-alcoholic steatohepatitis mouse model. The expression of α-SMA was increased in the MCD control group as compared to methionine choline standard (MCS) control group. On the other hand, α-SMA levels in the fusion protein-treated groups and the FGF21 mutant fusion protein-treated group were decreased as compared to the control group. The data are indicated as mean values and the standard errors of the means. Statistical analysis was performed by Dunnet's multiple comparison test after one-way ANOVA (###: P<0.001 vs. MCS control, ***: P<0.001 vs. MCD control).
Figure 13B:
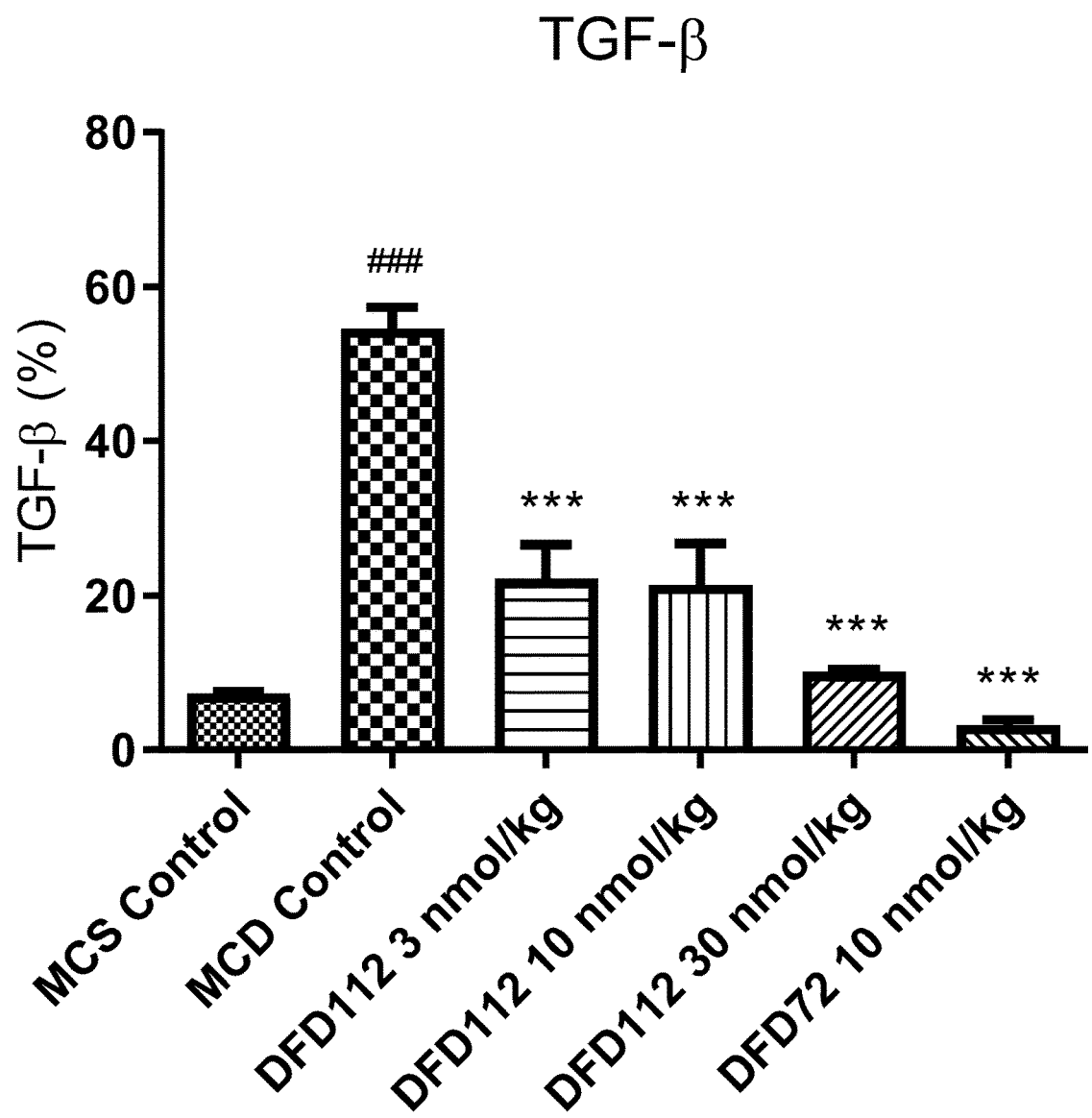
FIG. 13B is a graph showing changes in transforming growth factor-beta (TGF-β), a fibrosis-related indicator in the liver, after repeated subcutaneous administration of DFD112 and DFD72 at the interval of 2 days for 4 weeks in a MCD diet-induced non-alcoholic steatohepatitis mouse model. The expression of TGF-β was increased in the MCD control group as compared to MCS control group. On the other hand, TGF-β levels in the fusion protein-treated groups and the FGF21 mutant fusion protein-treated group were decreased as compared to the control group (###: P<0.001 vs. MCS control, ***: P<0.001 vs. MCD control).
Figure 13C:
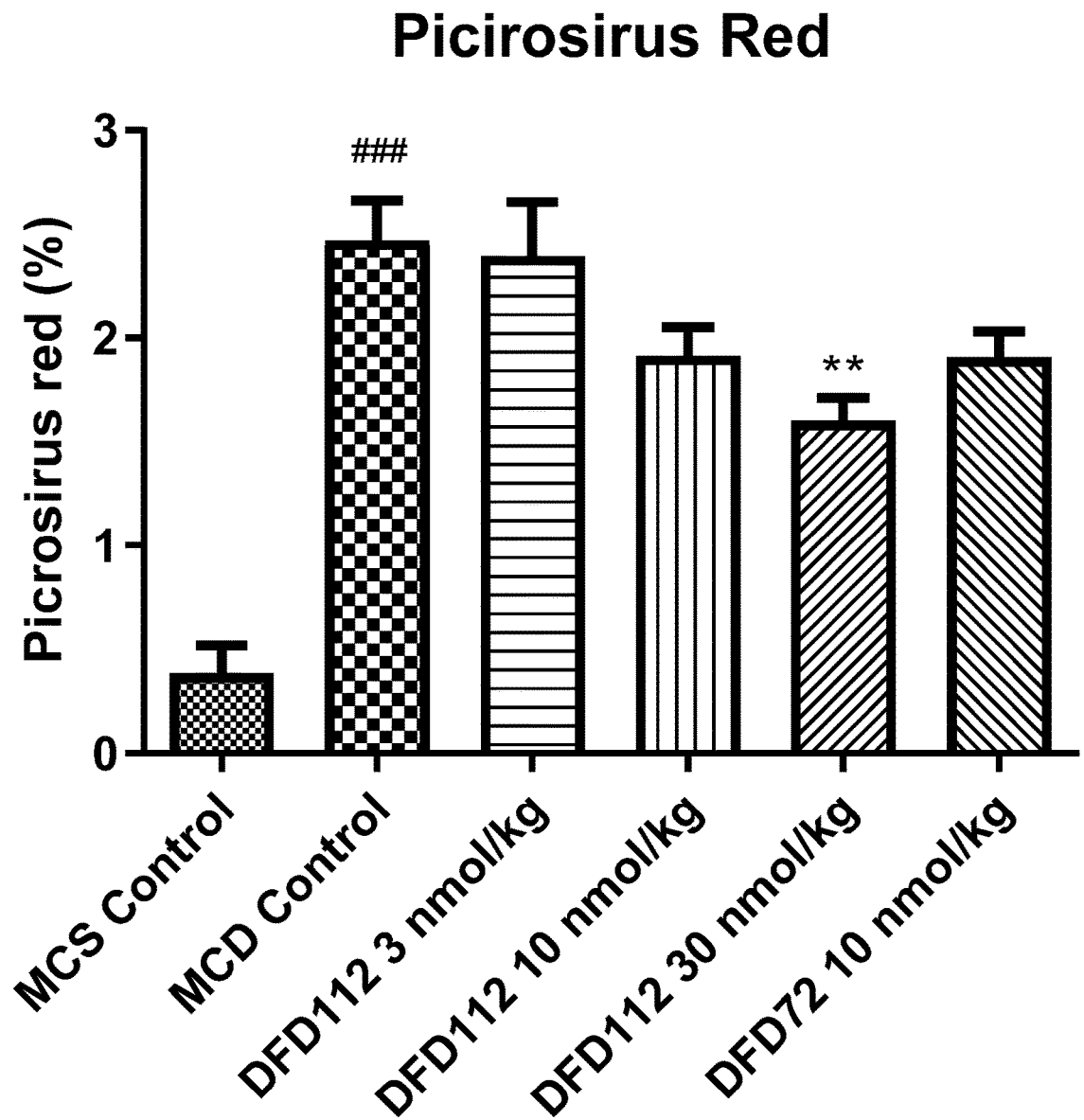
FIG. 13C is a graph showing the result of Picrosirius Red staining, a fibrosis-related indicator in the liver, after repeated subcutaneous administration of DFD112 and DFD72 at the interval of 2 days for 4 weeks in a MCD diet-induced non-alcoholic steatohepatitis mouse model. The amount of collagen was increased in the MCD control group as compared to MCS control group. On the other hand, Picrosirius Red levels in the fusion protein-treated groups and the FGF21 mutant fusion protein-treated group were decreased as compared to the control group (###: P<0.001 vs. MCS control, **: P<0.01 vs. MCD control).
Figure 14:
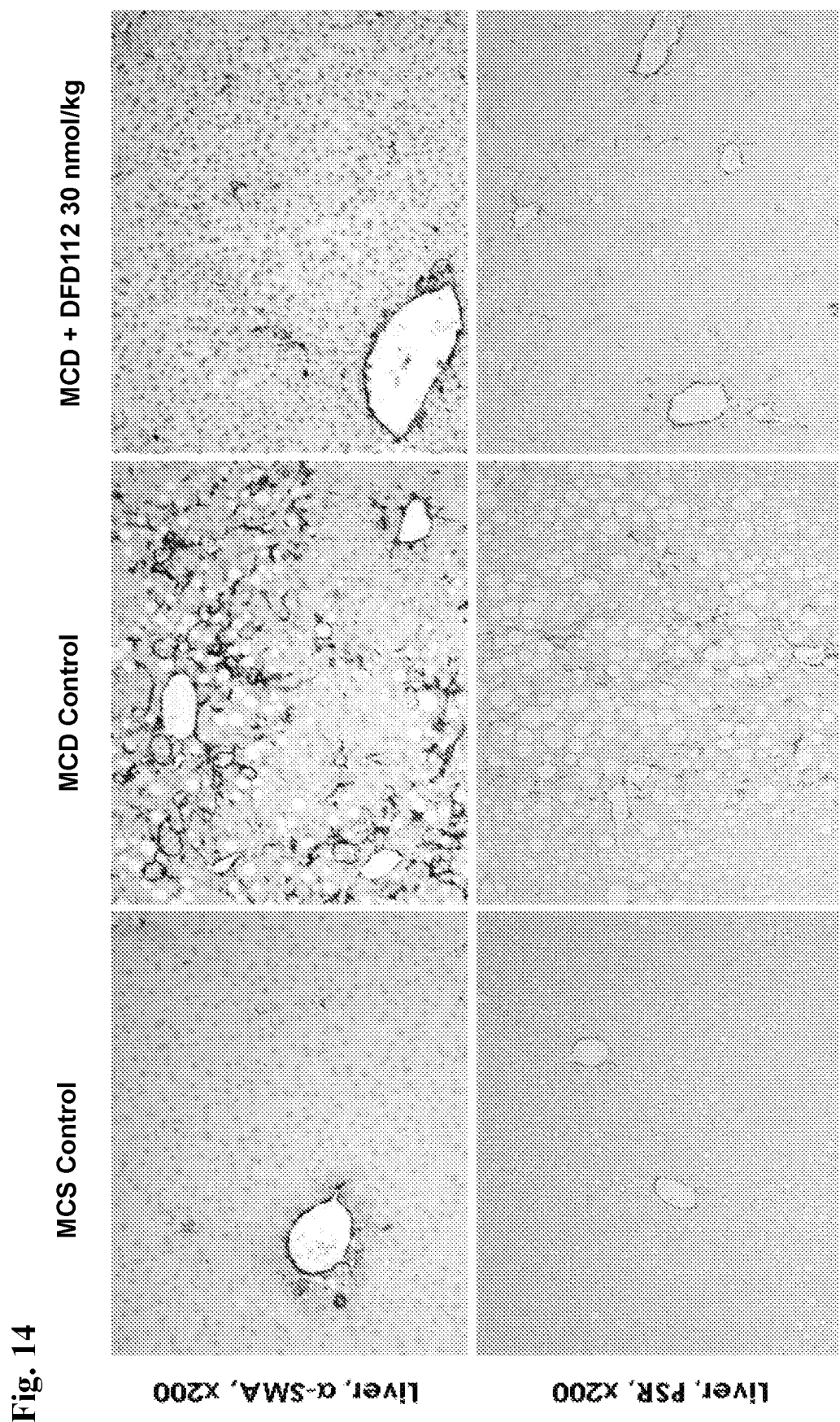
FIG. 14 shows histopathological photographs of the liver. The fat in the liver tissues was significantly reduced.
Figure 15A:
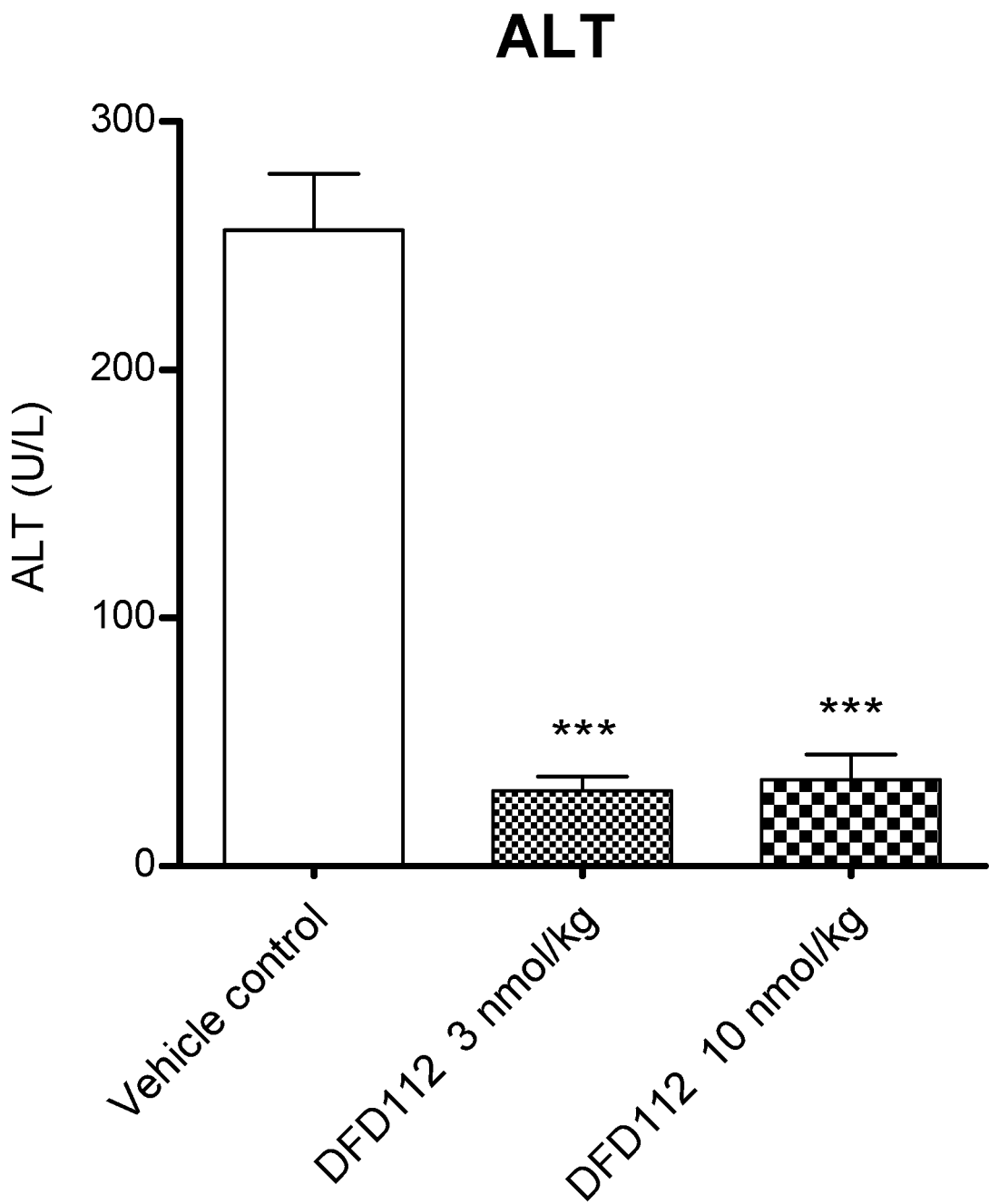
FIG. 15A is a graph showing changes in ALT level, a blood biochemical indicator, after repeated subcutaneous administration of DFD112 at the interval of 2 days for 8 weeks in diet-induced obesity and non-alcoholic steatohepatitis mouse models. When a fusion protein was administered, serum ALT reduction effect was observed as compared to the control group. The data are indicated as mean values and the standard errors of the means. Statistical analysis was performed by Dunnet's multiple comparison test after one-way ANOVA (***: P<0.001).
Figure 15B:
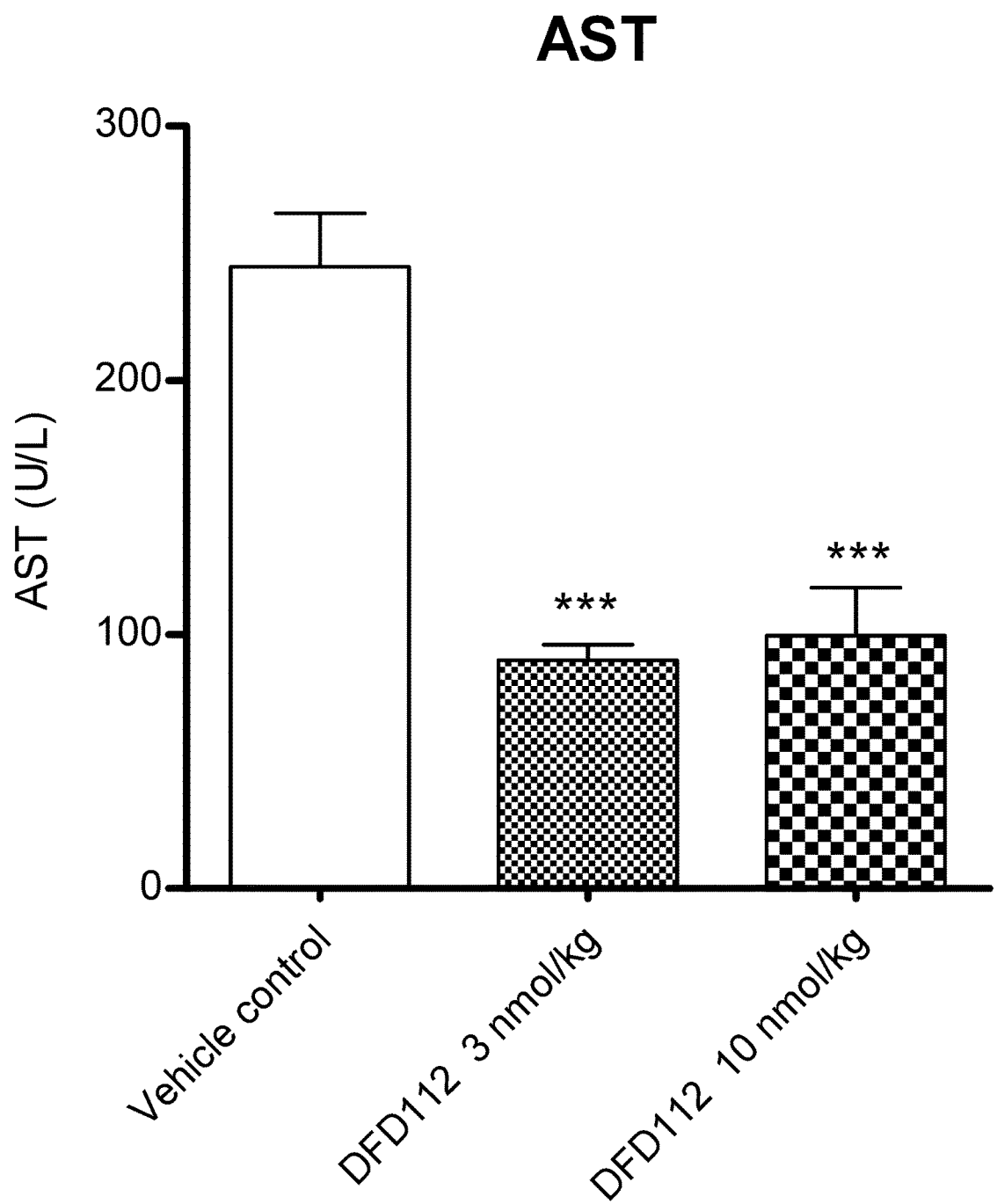
FIG. 15B is a graph showing changes in AST levels after repeated subcutaneous administration of DFD112 at the interval of 2 days for 8 weeks in diet-induced obesity and non-alcoholic steatohepatitis mouse models. When a fusion protein was administered, serum AST reduction effect was observed as compared to the control group (***: P<0.001).
Figure 15C:
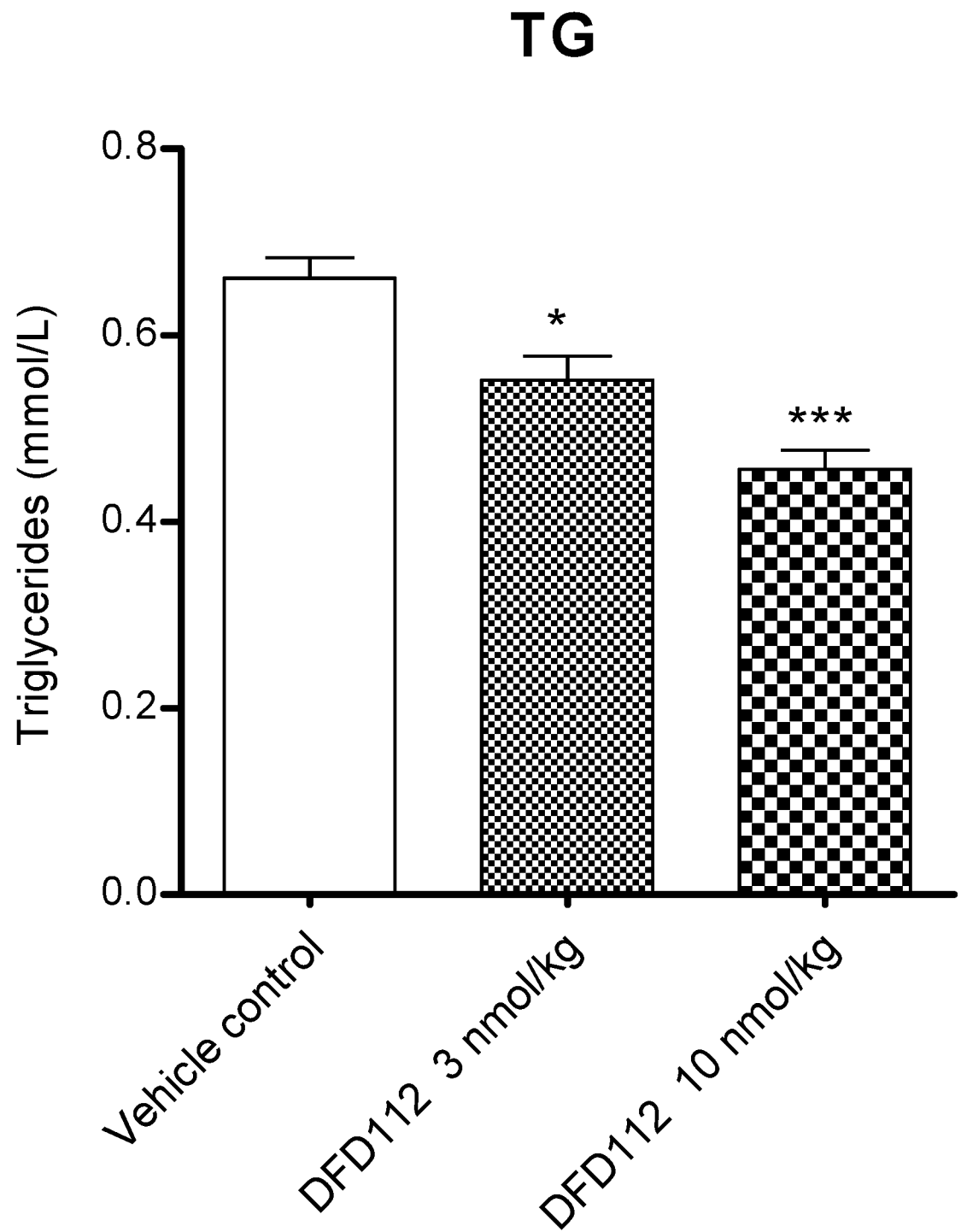
FIG. 15C is a graph showing changes in TG after repeated subcutaneous administration of DFD112 at the interval of 2 days for 8 weeks in diet-induced obesity and non-alcoholic steatohepatitis mouse models. When a fusion protein was administered, serum TG reduction effect was observed as compared to the control group (*: P<0.05, ***: P<0.001).
Figure 15D:
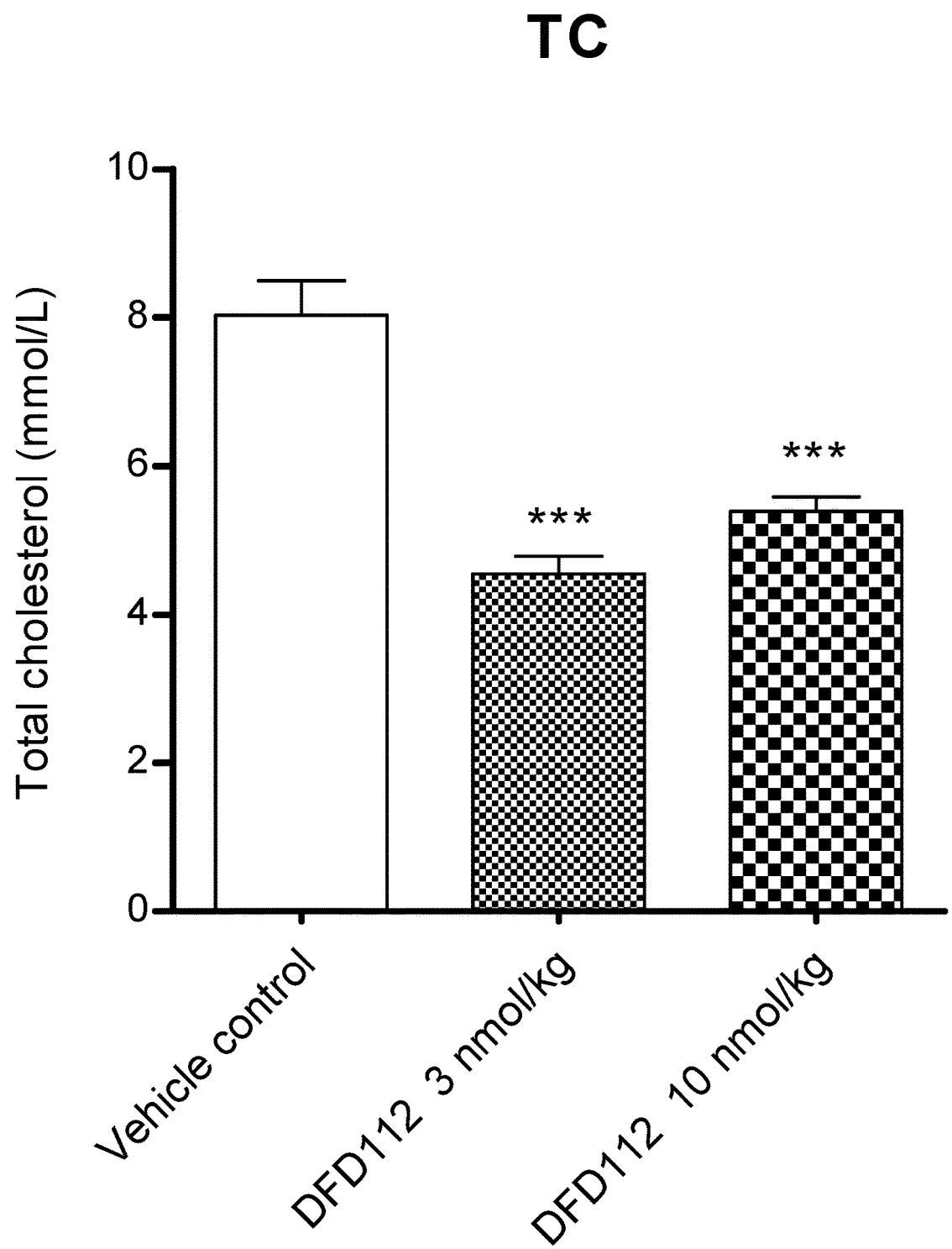
FIG. 15D is a graph showing changes in TC levels after repeated subcutaneous administration of DFD112 at the interval of 2 days for 8 weeks in diet-induced obesity and non-alcoholic steatohepatitis mouse models. When a fusion protein was administered, serum TC reduction effect was observed as compared to the control group (***: P<0.001).

As shown in FIGS. 12A to 12C, the MCD control group in which non-alcoholic steatohepatitis was induced showed significantly higher alanine aminotransferase (ALT) and aspartate transaminase (AST) ($p<0.001$), as liver damage indicators, as compared to the MCS control group fed with a normal diet. The serum AST and ALT levels were decreased in a dose dependent manner in the group administered with DFD112 as compared to the MCD control group. In addition, the MCD control group showed a significantly higher inflammation level as compared to the MCS control group on histopathological examination ($p<0.01$). When DFD112 was administered, the inflammation level was decreased in a dose-dependent manner as compared to MCD control group.

As shown in FIGS. 13A to 13C and FIG. 14, in order to evaluate the effect of the fusion protein on liver fibrosis, alpha-smooth muscle actin (α-SMA) and transforming growth factor-beta (TGF-β) in liver tissue, as liver fibrosis indicators, were stained using immunohistochemical staining, and quantified by image analysis. The expressions of α-SMA and TGF-β were increased in the MCD control group as compared to the MCS control group ($p<0.001$). When DFD112 and DFD72 were administered, the expressions of α-SMA and TGF-β were decreased as compared to the MCD control group. In addition, collagen in liver tissue was stained using Picrosirius red staining and quantified by image analysis. As a result, the amount of collagen in the MCD control group was higher than the MCS control group ($p<0.001$), and when DFD112 and DFD72 were administered, decreasing tendency of collagen in the liver tissue was observed as compared to the MCD control group.

Experimental Example 9. Activity Evaluation of Fusion Proteins in Diet-Induced Obesity and Non-Alcoholic Steatohepatitis Mice Experimental Example 9-1. Method for Activity Evaluation of Fusion Proteins in Diet-Induced Obesity and Non-Alcoholic Steatohepatitis Mice In order to evaluate the inflammation- and fibrosis-reduction effects of fusion proteins in a non-alcoholic steatohepatitis model, the effect of DFD112 was evaluated in a diet-induced obesity and non-alcoholic steatohepatitis mouse model.

A mouse model with obesity and non-alcoholic steatohepatitis was prepared by feeding C57BL/6 mice with a high fat diet (Research diet) containing 40% fat, 40% carbohydrate and 2% cholesterol for about 30 weeks. Histopathological examination of liver tissue was performed about 3 weeks before the drug treatment, and ALT and AST levels and body weight were measured before administration. Experimental animals were selected such that non-alcoholic steatohepatitis induction degrees and body weights are evenly distributed, and were divided into groups. 12 mice were assigned to each group, and DFD112 was repeatedly administered subcutaneously at a dose of 3 or 10 nmol/kg at 2 day interval for 8 weeks. In the control group, the solvent used to prepare the test substance (Dulbecco's phosphate buffered saline, DPBS, Gibco, USA) was injected by the same method.

After the last administration, the mice were fasted overnight and blood was collected from the postcaval vein and liver tissues were extracted after inhalation anesthesia and laparotomy. Blood biochemical tests were performed with serum samples isolated from the collected blood samples. The fixed liver tissues were prepared as specimens, and the prepared specimens were stained with hematoxylin and eosin (H&E) or Picrosirius red, and histopathological changes were observed.

Experimental Example 9-2. Activity Evaluation Results of Fusion Proteins in Diet-Induced Obesity and Non-Alcoholic Steatohepatitis Mice A diet-induced obesity and non-alcoholic steatohepatitis mice were repeatedly administered with DFD112 at a dose of 3 or 10 nmol/kg at 2 day interval for 8 weeks. Then, the blood biochemical and histopathological examination were performed to evaluate the effect on non-alcoholic steatohepatitis.

*322 As shown in FIGS. 15A to 15D, serum ALT and AST levels, as liver injury indicators, were decreased to a normal level ($p<0.001$) in the group administered with DFD112. Serum triglyceride (TG) and total cholesterol (TC) levels were also significantly decreased as compared to the vehicle control group (p<0.05 or p<0.001).

Figure 16A:
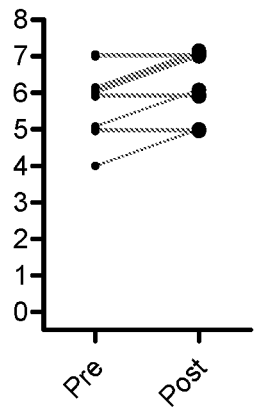
FIG. 16A provides graphs showing changes in NAFLD activity scores (NAS) between pre- and post-administration in the liver, after repeated subcutaneous administration of DFD112 at the interval of 2 days for 8 weeks in diet-induced obesity and non-alcoholic steatohepatitis mouse models. When a fusion protein was administered, post-administration NAFLD activity score was decreased as compared to pre-administration score.
Figure 16A:
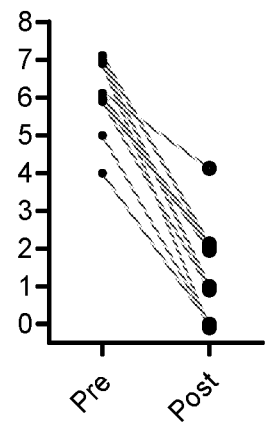
Figure 16A:
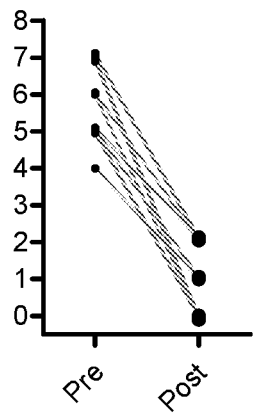
Figure 16B:
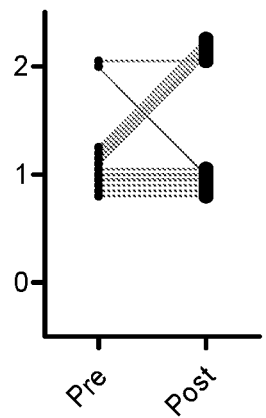
FIG. 16B provides graphs showing changes in liver fibrosis scores between pre- and post-administration in the liver, after repeated subcutaneous administration of DFD112 at the interval of 2 days for 8 weeks in diet-induced obesity and non-alcoholic steatohepatitis mouse models. When a fusion protein was administered, post-administration liver fibrosis score was decreased as compared to pre-administration score.
Figure 16B:
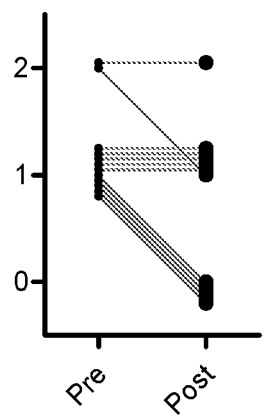
Figure 16B:
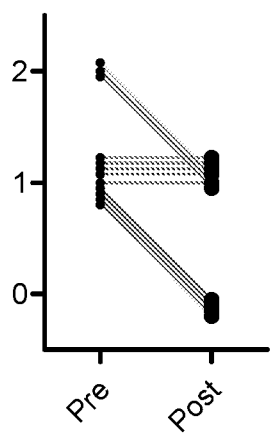
Figure 17A:
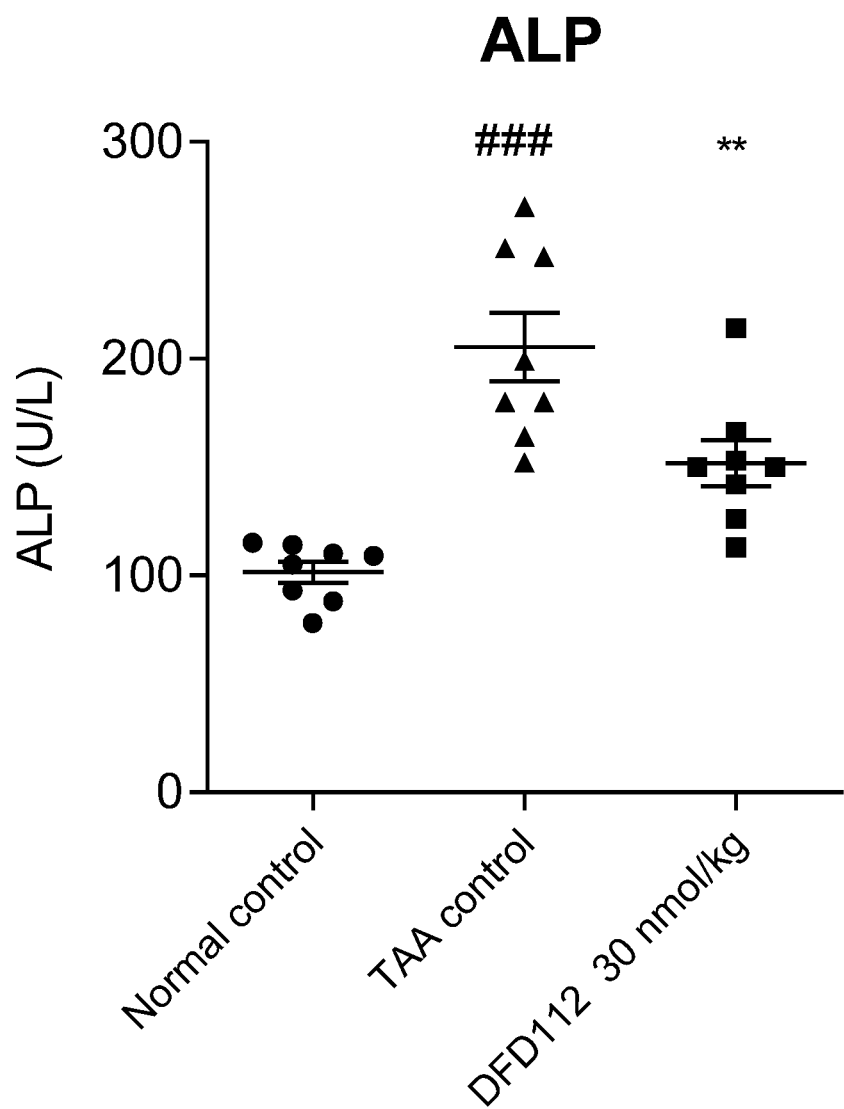
FIG. 17A is a graph showing changes in ALP levels, a blood biochemical indicator, after repeated subcutaneous administration of DFD112 at the interval of 2 days for 8 weeks in a thioacetamide (TAA)-induced hepatic fibrosis rat model. When a fusion protein was administered, serum ALP reduction effect was observed as compared to the TAA control group. The data are indicated as mean values and the standard errors of the means. Statistical analysis was performed by Dunnet's multiple comparison test after one-way ANOVA (###: P<0.001 vs. Normal control, **: P<0.01 vs. TAA control).
Figure 17B:
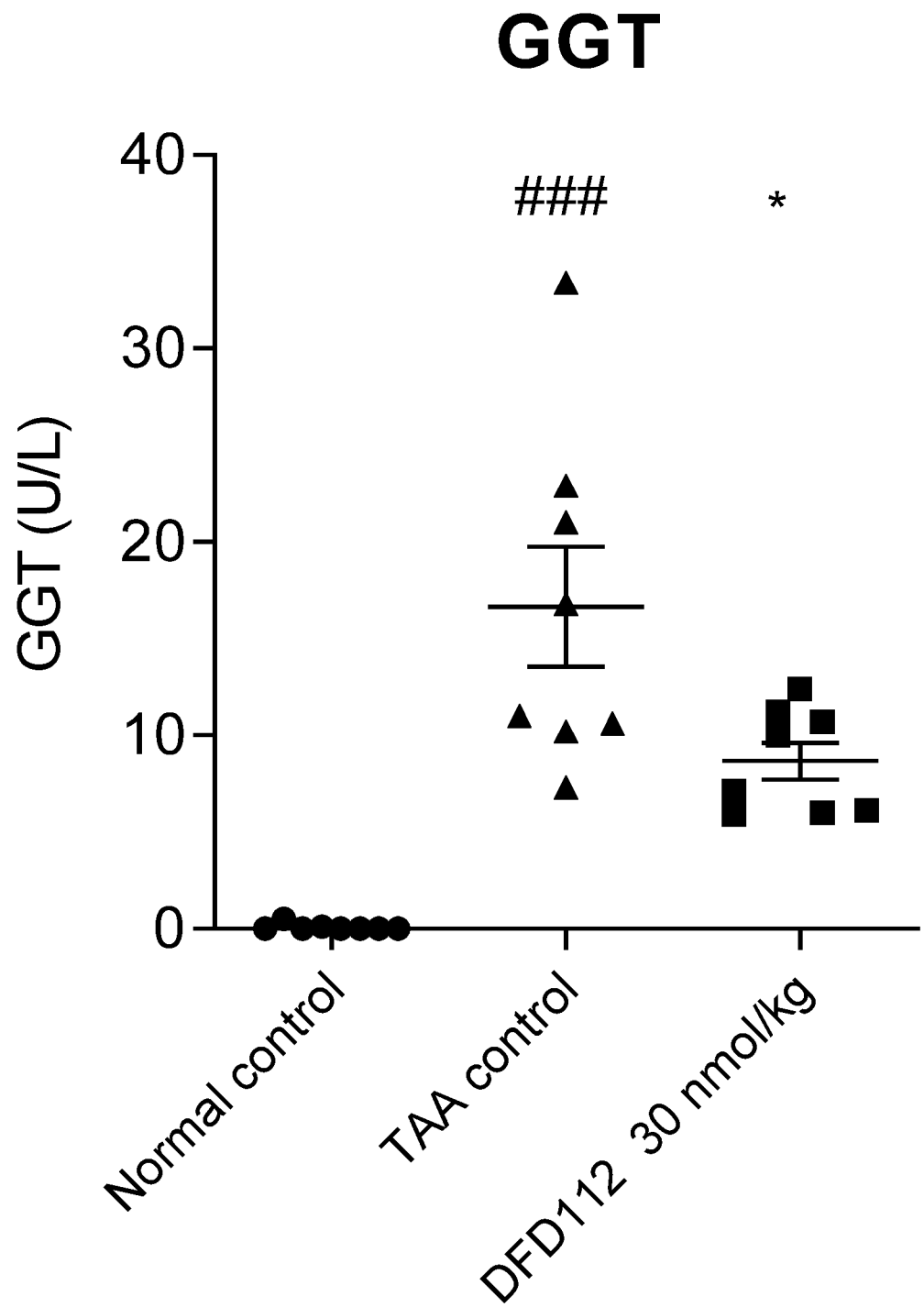
FIG. 17B is a graph showing changes in GGT levels, a blood biochemical indicator, after repeated subcutaneous administration of DFD112 at the interval of 2 days for 8 weeks in a thioacetamide (TAA)-induced hepatic fibrosis rat model. When a fusion protein was administered, serum GGT reduction effect was observed as compared to the TAA control group (###: P<0.001 vs. Normal control, *: P<0.05 vs. TAA control).
Figure 17C:
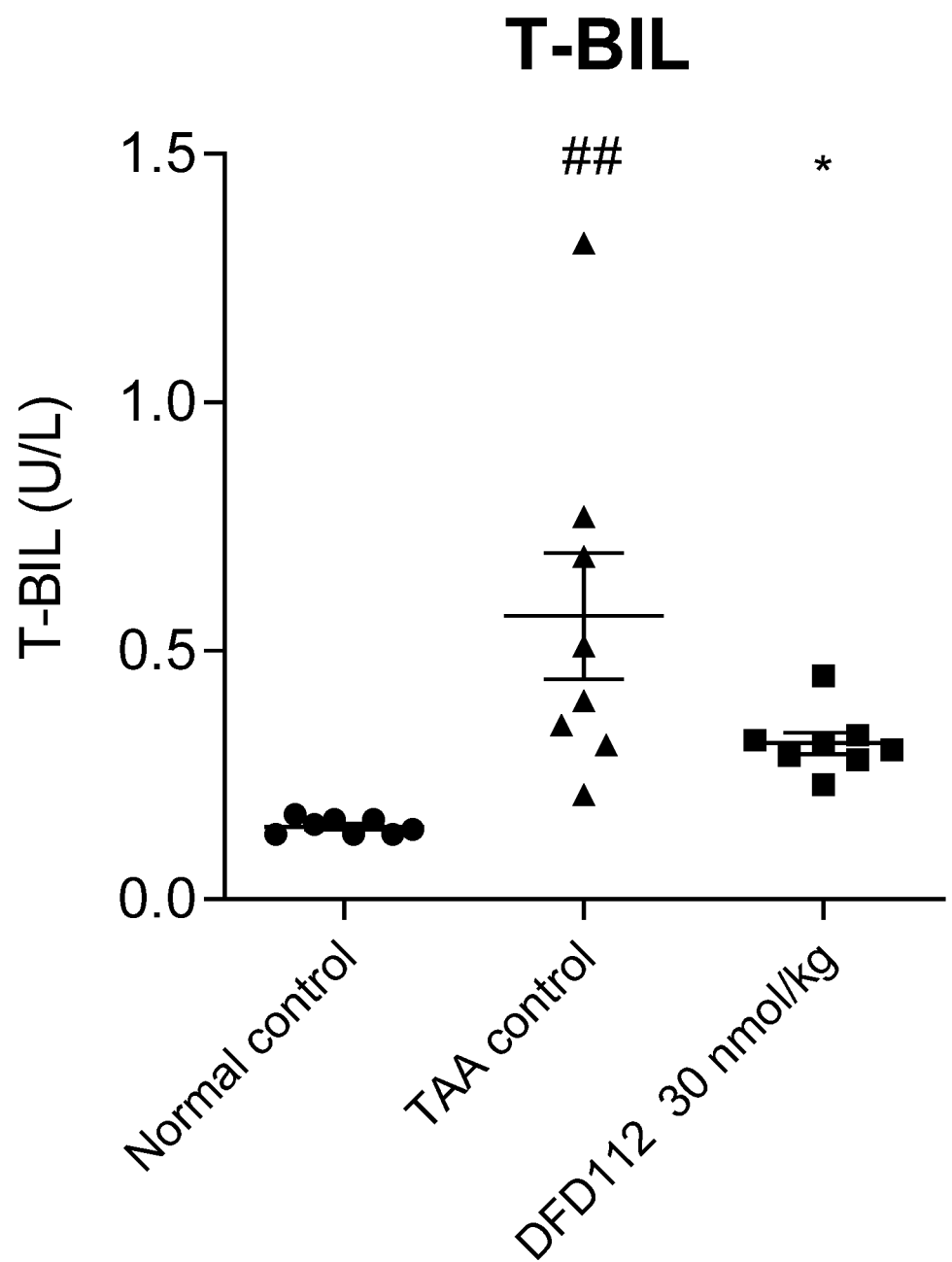
FIG. 17C is a graph showing changes in T-BIL levels, a blood biochemical indicator, after repeated subcutaneous administration of DFD112 at the interval of 2 days for 8 weeks in a thioacetamide (TAA)-induced hepatic fibrosis rat model. When a fusion protein was administered, serum T-BIL reduction effect was observed as compared to the control group (##: P<0.01 vs. Normal control, *: P<0.05 vs. TAA control).
Figure 17D:
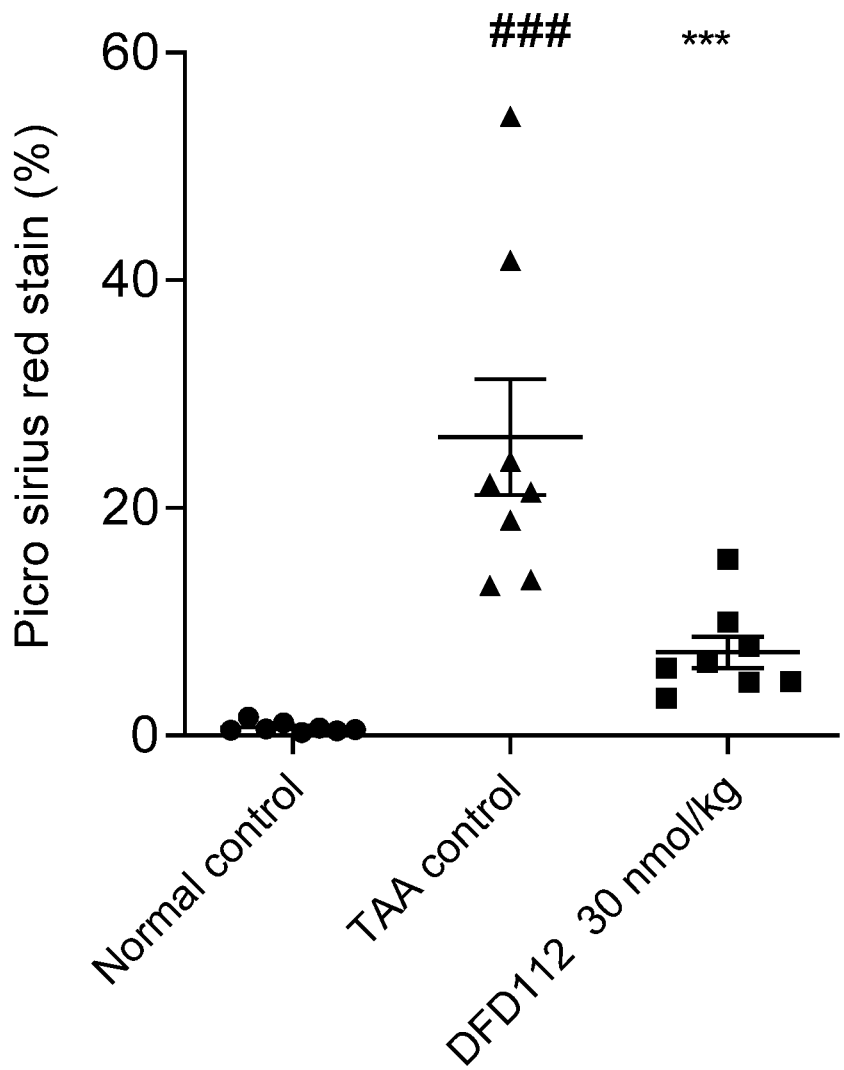
FIG. 17D is a graph showing changes in fibrosis areas in liver, after repeated subcutaneous administration of DFD112 at the interval of 2 days for 8 weeks in a thioacetamide (TAA)-induced hepatic fibrosis rat model. When a fusion protein was administered, fibrosis area reduction effect was observed as compared to the control group (###: P<0.001 vs. Normal control, ***: P<0.001 vs. TAA control).

As shown in FIGS. 16A to 16B, the histopathological examination results from pre- and post-administration showed that the post-administration NAFLD activity score (NAS), as an index for classifying non-alcoholic steatohepatitis grades, was increased or maintained in the vehicle control group, with 8 weeks of repeated administration, as compared to pre-administration score. On the other hand, the NAFLD activity scores were significantly decreased in all subjects in the DFD112 administration group as compared to the pre-administration score. In addition, upon fibrosis degree evaluation, the degree of fibrosis was maintained or worsened in the control group as compared to the pre-administration degree, whereas a significant improving effect was observed (p<0.05) in the DFD112 administration group.

Experimental Example 10. Evaluation of Fusion Protein Activity in TAA-Induced Hepatic Fibrosis Rat Experimental Example 10-1. Evaluation Method of Fusion Protein Activity in TAA-Induced Hepatic Fibrosis Rats The effect of DFD112 was evaluated in a rat model in which hepatic fibrosis was induced by drinking water in order to evaluate the hepatic fibrosis-reducing effect of fusion proteins.

A hepatic fibrosis model was prepared by providing Wistar rats with drinking water containing thioacetamide (TAA) for about 14 weeks. The animals were weighed before administration of the test substance, and randomly assigned into groups such that the average body weight of each group was distributed as evenly as possible. After 8 rats were assigned to each group, DFD112 of 30 nmol/kg was subcutaneously administered repeatedly at the interval of 2 days for 8 weeks. TAA drinking water was continuously provided until the end of the administration. Normal control group was fed with normal drinking water from the start of the test to the end of the administration, and TAA control group was fed with TAA drinking water from the start of the test to the end of the administration.

After the end of the administration, the mice were fasted overnight and blood was collected from the postcaval vein and liver tissues were extracted after inhalation anesthesia and laparotomy. Blood biochemical tests were performed with serum samples isolated from the collected blood samples, and the fixed liver tissues were prepared as specimens and stained with Picrosirius red and histopathological changes were observed in order to compare the degree of fibrosis of liver parenchyme.

Experimental Example 10-2. Method for Evaluation of Fusion Protein Activity in TAA-Induced Hepatic Fibrosis Rats 30 nmol/kg of fusion protein DFD112 was administered to TAA-induced hepatic fibrosis rats repeatedly at the interval of 2 days for 8 weeks, and the effect on hepatic fibrosis was evaluated by blood biochemical tests and histopathological examinations.

As shown in FIGS. 17a to 17d, the TAA control group in which hepatic fibrosis was induced showed significantly higher levels of alkaline phosphatase (ALP), gamma-glutamyltransferase (GGT) and total bilirubin (T-bil) (p<0.01 or p<0.001), as liver damage indicators, as compared to the control group to which normal drinking water was provided.

It was observed that ALT, GGT and T-bil levels were significantly decreased with DFD112 administration as compared to TAA control group. Histopathological examination showed that the proportion of hepatic fibrosis area positively stained with Picrosirius red staining was significantly increased in the TAA control group as compared to the normal control group. In addition, it was observed that the proportion of hepatic fibrosis area was significantly decreased with DFD112 administration as compared to TAA control group (p<0.001).

The invention claimed is:

1. A method for treating hepatitis, hepatic fibrosis, or hepatic cirrhosis in a subject in need thereof, said method comprising administering to the subject a pharmaceutical composition comprising a fusion protein, said fusion protein comprising a fibroblast growth factor 21 (FGF21) mutant protein and an Fc region of an immunoglobulin linked to the FGF21 mutant protein, wherein the FGF21 mutant protein comprises a mutation selected from the group consisting of the following mutations (a), (b), (c), and (d):

(a) a substitution of the amino acids at positions 98 to 101 from the N-terminus of a wild-type FGF21 protein with the amino acid sequence of EIRP (SEQ ID NO: 68);

(b) a substitution of the amino acids at positions 170 to 174 from the N-terminus of a wild-type FGF21 protein with the amino acid sequence of TGLEAV (SEQ ID NO: 69);

(c) a substitution of the amino acids at positions 170 to 174 from the N-terminus of a wild-type FGF21 protein with the amino acid sequence of TGLEAN (SEQ ID NO: 70); and (d) a substitution of the amino acid at position 174 from the N-terminus of a wild-type FGF21 protein with the amino acid N, and wherein the wild-type FGF21 protein in the (a), (b), (c), and (d) comprises the amino acid sequence of SEQ ID NO: 1.

2. The method of claim 1, wherein the fusion protein further comprises a biologically active protein, or a biologically active mutant or biologically active fragment thereof.

3. The method of claim 2, wherein the amino acid residue N of the FGF21 mutant protein introduced by the mutation of (c) or (d) are glycosylated.

4. The method of claim 2, wherein the biologically active protein is one selected from the group consisting of insulin, C-peptide, leptin, glucagon, gastrin, gastric inhibitory polypeptide (GIP), amylin, calcitonin, cholecystokinin, peptide YY, neuropeptide Y, bone morphogenetic protein-6 (BMP-6), bone morphogenetic protein-9 (BMP-9), oxyntomodulin, oxytocin, glucagon-like peptide-1 (GLP-1), glucagon-like peptide-2 (GLP-2), irisin, fibronectin type III domain-containing protein 5 (FNDC5), apelin, adiponectin, C1q and tumor necrosis factor related protein (CTRP family), resistin, visfatin, omentin, retinol binding protein-4 (RBP-4), glicentin, angiopoietin, interleukin-22 (IL-22), exendin-4, and growth hormone.

5. The method of claim 4, wherein the biologically active protein is one selected from GLP-1, a biologically active mutant thereof, and exendin-4.

6. The method of claim 5, wherein the biologically active mutant of GLP-1 comprises the amino acid sequence of any one of SEQ ID NO: 43 to 46.

7. The method of claim 2, wherein the fusion protein comprises, in the order from the N-terminus to the C-terminus, the biologically active protein, the Fc region of the immunoglobulin, and the FGF21 mutant protein.

8. The method of claim 7, wherein the fusion protein further comprises a linker connected between the Fc region of the immunoglobulin and the FGF21 mutant protein.

9. The method of claim 2, wherein the fusion protein comprises any one of the amino acid sequences selected from SEQ ID NO: 65, 66 and 67.

10. The method of claim 2, wherein the FGF21 mutant protein further comprises a substitution of the amino acid at position 180 from the N-terminus of the wild-type FGF21 protein with the amino acid E.

11. The method of claim 2, wherein the mutation is (a) or (d) and the FGF21 mutant protein further comprises a mutation selected from the group consisting of the following mutations (e) and (f):

(e) a substitution of the amino acid at position 170 from the N-terminus of the wild-type FGF21 protein with the amino acid N; and (f) a substitution of the amino acid at position 180 from the N-terminus of the wild-type FGF21 protein with the amino acid E.

12. The method of claim 1, wherein the FGF21 mutant protein comprises the amino acid sequence of any one of SEQ ID NO: 6, 7, 8, 10, 11, 12, 13, 14, 15, 16, 17, 19, 20, 21, 22, or 23.

13. The method of claim 1, wherein the fusion protein further comprises a linker.

14. The method of claim 13, wherein the linker connects the FGF21 mutant protein to the Fc region of the immunoglobulin.

15. The method of claim 14, wherein one end of the linker is connected to the C-terminus of the Fc region of the immunoglobulin and the other end of the linker is connected to the N-terminus of the FGF21 mutant protein.

16. The method of claim 14, wherein the linker is a peptide consisting of 10 to 30 amino acid residues.

17. The method of claim 16, wherein the linker comprises the amino acid sequence of any one of SEQ ID NO: 2 to 5.

18. The method of claim 1, wherein the Fc region of the immunoglobulin is any one of the Fc region of IgG1, IgG2, IgG3, IgG4 and IgD, or a hybrid Fc containing a combination thereof.

19. The method of claim 18, wherein the hybrid Fc comprises an IgG4 region and an IgD region.

20. The method of claim 1, wherein the fusion protein comprises any one of the amino acid sequences selected from SEQ ID NO: 36, 37 and 39.

21. A method of reducing lipid levels in liver of a subject in need thereof, comprising administering to the subject a pharmaceutical composition comprising a fusion protein, said fusion protein comprising a fibroblast growth factor 21 (FGF21) mutant protein and an Fc region of an immunoglobulin linked to the FGF21 mutant protein, wherein the FGF21 mutant protein comprises a mutation selected from the group consisting of the following mutations (a), (b), (c), and (d):
(a) a substitution of the amino acids at positions 98 to 101 from the N-terminus of a wild-type FGF21 protein with the amino acid sequence of EIRP (SEQ ID NO: 68);
(b) a substitution of the amino acids at positions 170 to 174 from the N-terminus of a wild-type FGF21 protein with the amino acid sequence of TGLEAV (SEQ ID NO: 69);
(c) a substitution of the amino acids at positions 170 to 174 from the N-terminus of a wild-type FGF21 protein with the amino acid sequence of TGLEAN (SEQ ID NO: 70); and
(d) a substitution of an amino acid at position 174 from the N-terminus of a wild-type FGF21 protein with the amino acid N, and
wherein the wild-type FGF21 protein in the (a), (b), (c), and (d) comprises the amino acid sequence of SEQ ID NO: 1.

* * * * *

SEQUENCE LISTING

```
<160> NUMBER OF SEQ ID NOS: 83

<210> SEQ ID NO 1
<211> LENGTH: 181
<212> TYPE: PRT
<213> ORGANISM: Homo sapiens

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
```

```
            100                 105                 110
Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 2
<211> LENGTH: 30
<212> TYPE: PRT
<213> ORGANISM: Artificial Sequence
<220> FEATURE:
<223> OTHER INFORMATION: linker

<400> SEQUENCE: 2

Ala Lys Ala Thr Thr Ala Pro Ala Thr Thr Arg Asn Thr Gly Arg Gly
1               5                   10                  15

Gly Glu Glu Lys Lys Lys Glu Lys Glu Lys Glu Glu Gln Glu
            20                  25                  30

<210> SEQ ID NO 3
<211> LENGTH: 17
<212> TYPE: PRT
<213> ORGANISM: Artificial Sequence
<220> FEATURE:
<223> OTHER INFORMATION: linker

<400> SEQUENCE: 3

Ala Lys Ala Thr Thr Ala Pro Ala Thr Thr Arg Asn Thr Gly Arg Gly
1               5                   10                  15

Gly

<210> SEQ ID NO 4
<211> LENGTH: 15
<212> TYPE: PRT
<213> ORGANISM: Artificial Sequence
<220> FEATURE:
<223> OTHER INFORMATION: linker

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: linker

<400> SEQUENCE: 5

Gly Gly Gly Gly Ser Gly Gly Gly Gly Ser Gly Gly Gly Gly Ser Ala
1               5                   10                  15

<210> SEQ ID NO 6
<211> LENGTH: 181
<212> TYPE: PRT
<213> ORGANISM: Artificial Sequence
```

```
<220> FEATURE:
<223> OTHER INFORMATION: FGF21 variant

<400> SEQUENCE: 6

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 7
<211> LENGTH: 182
<212> TYPE: PRT
<213> ORGANISM: Artificial Sequence
<220> FEATURE:
<223> OTHER INFORMATION: FGF21 variant

<400> SEQUENCE: 7

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
```

```
                145                 150                 155                 160
Gly Ser Ser Asp Pro Leu Ser Met Val Thr Gly Leu Glu Ala Val Arg
                    165                 170                 175
Ser Pro Ser Tyr Ala Ser
                180

<210> SEQ ID NO 8
<211> LENGTH: 182
<212> TYPE: PRT
<213> ORGANISM: Artificial Sequence
<220> FEATURE:
<223> OTHER INFORMATION: FGF21 variant

<400> SEQUENCE: 8

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Asn Arg
                    165                 170                 175

Ser Pro Ser Tyr Ala Ser
                180

<210> SEQ ID NO 9
<211> LENGTH: 181
<212> TYPE: PRT
<213> ORGANISM: Artificial Sequence
<220> FEATURE:
<223> OTHER INFORMATION: FGF21 variant

<400> SEQUENCE: 9

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80
```

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Asn Pro Ser Gln Gly Arg Ser
            165                 170                 175

Pro Ser Tyr Ala Ser
            180

<210> SEQ ID NO 10
<211> LENGTH: 181
<212> TYPE: PRT
<213> ORGANISM: Artificial Sequence
<220> FEATURE:
<223> OTHER INFORMATION: FGF21 variant

<400> SEQUENCE: 10

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Asn Arg Ser
            165                 170                 175

Pro Ser Tyr Ala Ser
            180

<210> SEQ ID NO 11
<211> LENGTH: 182
<212> TYPE: PRT
<213> ORGANISM: Artificial Sequence
<220> FEATURE:
<223> OTHER INFORMATION: FGF21 variant

<400> SEQUENCE: 11

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Val Arg
                165                 170                 175

Ser Pro Ser Tyr Ala Ser
            180

<210> SEQ ID NO 12
<211> LENGTH: 182
<212> TYPE: PRT
<213> ORGANISM: Artificial Sequence
<220> FEATURE:
<223> OTHER INFORMATION: FGF21 variant

<400> SEQUENCE: 12

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Asn Arg
                165                 170                 175

Ser Pro Ser Tyr Ala Ser
            180

<210> SEQ ID NO 13
<211> LENGTH: 181
<212> TYPE: PRT
<213> ORGANISM: Artificial Sequence
<220> FEATURE:
<223> OTHER INFORMATION: FGF21 variant

<400> SEQUENCE: 13

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Asn Pro Ser Gln Gly Arg Ser
                165                 170                 175

Pro Ser Tyr Ala Ser
            180
```

<210> SEQ ID NO 14
<211> LENGTH: 181
<212> TYPE: PRT
<213> ORGANISM: Artificial Sequence
<220> FEATURE:
<223> OTHER INFORMATION: FGF21 variant

<400> SEQUENCE: 14

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
```

-continued

```
                115                 120                 125
Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Asn Arg Ser
                165                 170                 175

Pro Ser Tyr Ala Ser
            180

<210> SEQ ID NO 15
<211> LENGTH: 181
<212> TYPE: PRT
<213> ORGANISM: Artificial Sequence
<220> FEATURE:
<223> OTHER INFORMATION: FGF21 variant

<400> SEQUENCE: 15

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Glu Ser
            180

<210> SEQ ID NO 16
<211> LENGTH: 182
<212> TYPE: PRT
<213> ORGANISM: Artificial Sequence
<220> FEATURE:
<223> OTHER INFORMATION: FGF21 variant

<400> SEQUENCE: 16

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45
```

```
Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Val Arg
                165                 170                 175

Ser Pro Ser Tyr Glu Ser
            180

<210> SEQ ID NO 17
<211> LENGTH: 182
<212> TYPE: PRT
<213> ORGANISM: Artificial Sequence
<220> FEATURE:
<223> OTHER INFORMATION: FGF21 variant

<400> SEQUENCE: 17

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Asn Arg
                165                 170                 175

Ser Pro Ser Tyr Glu Ser
            180

<210> SEQ ID NO 18
<211> LENGTH: 181
<212> TYPE: PRT
<213> ORGANISM: Artificial Sequence
<220> FEATURE:
```

<223> OTHER INFORMATION: FGF21 variant

<400> SEQUENCE: 18

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Asn Pro Ser Gln Gly Arg Ser
                165                 170                 175

Pro Ser Tyr Glu Ser
            180
```

<210> SEQ ID NO 19
<211> LENGTH: 181
<212> TYPE: PRT
<213> ORGANISM: Artificial Sequence
<220> FEATURE:
<223> OTHER INFORMATION: FGF21 variant

<400> SEQUENCE: 19

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160
```

Gly Ser Ser Asp Pro Leu Ser Met Val Gly Pro Ser Gln Asn Arg Ser
                165                 170                 175

Pro Ser Tyr Glu Ser
            180

<210> SEQ ID NO 20
<211> LENGTH: 182
<212> TYPE: PRT
<213> ORGANISM: Artificial Sequence
<220> FEATURE:
<223> OTHER INFORMATION: FGF21 variant

<400> SEQUENCE: 20

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Val Arg
                165                 170                 175

Ser Pro Ser Tyr Glu Ser
            180

<210> SEQ ID NO 21
<211> LENGTH: 182
<212> TYPE: PRT
<213> ORGANISM: Artificial Sequence
<220> FEATURE:
<223> OTHER INFORMATION: FGF21 variant

<400> SEQUENCE: 21

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg

```
                    85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Asn Arg
                165                 170                 175

Ser Pro Ser Tyr Glu Ser
            180

<210> SEQ ID NO 22
<211> LENGTH: 181
<212> TYPE: PRT
<213> ORGANISM: Artificial Sequence
<220> FEATURE:
<223> OTHER INFORMATION: FGF21 variant

<400> SEQUENCE: 22

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Asn Pro Ser Gln Gly Arg Ser
                165                 170                 175

Pro Ser Tyr Glu Ser
            180

<210> SEQ ID NO 23
<211> LENGTH: 181
<212> TYPE: PRT
<213> ORGANISM: Artificial Sequence
<220> FEATURE:
<223> OTHER INFORMATION: FGF21 variant

<400> SEQUENCE: 23

His Pro Ile Pro Asp Ser Ser Pro Leu Leu Gln Phe Gly Gly Gln Val
1               5                   10                  15
```

```
Arg Gln Arg Tyr Leu Tyr Thr Asp Asp Ala Gln Gln Thr Glu Ala His
                20                  25                  30

Leu Glu Ile Arg Glu Asp Gly Thr Val Gly Ala Ala Asp Gln Ser
         35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Glu Ile Arg Pro Asp Gly Tyr Asn Val Tyr Gln Ser Glu Ala His
                100                 105                 110

Gly Leu Pro Leu His Leu Pro Gly Asn Lys Ser Pro His Arg Asp Pro
             115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Asn Arg Ser
                165                 170                 175

Pro Ser Tyr Glu Ser
            180

<210> SEQ ID NO 24
<211> LENGTH: 229
<212> TYPE: PRT
<213> ORGANISM: Artificial Sequence
<220> FEATURE:
<223> OTHER INFORMATION: Human IgG4 Fc

<400> SEQUENCE: 24

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
 50                 55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190
```

```
Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys
225

<210> SEQ ID NO 25
<211> LENGTH: 228
<212> TYPE: PRT
<213> ORGANISM: Artificial Sequence
<220> FEATURE:
<223> OTHER INFORMATION: Human IgG4 Fc variant

<400> SEQUENCE: 25

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 26
<211> LENGTH: 223
<212> TYPE: PRT
<213> ORGANISM: Artificial Sequence
<220> FEATURE:
<223> OTHER INFORMATION: Hybrid Fc variant

<400> SEQUENCE: 26

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30
```

```
Pro Glu Val Thr Cys Val Val Asp Val Ser Gln Glu Asp Pro Glu
            35                  40                  45

Val Gln Phe Asn Trp Tyr Val Asp Gly Val Glu Val His Asn Ala Lys
 50                  55                  60

Thr Lys Pro Arg Glu Glu Gln Phe Asn Ser Thr Tyr Arg Val Val Ser
 65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Gln Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
            195                 200                 205

His Asn His Tyr Thr Gln Lys Ser Leu Ser Leu Ser Leu Gly Lys
            210                 215                 220

<210> SEQ ID NO 27
<211> LENGTH: 435
<212> TYPE: PRT
<213> ORGANISM: Artificial Sequence
<220> FEATURE:
<223> OTHER INFORMATION: modified FGF21 variant connected to hybrid Fc

<400> SEQUENCE: 27

Glu Thr Lys Thr Pro Glu Cys Pro Ser His Thr Gln Pro Leu Gly Val
 1               5                  10                  15

Phe Leu Phe Pro Pro Lys Pro Lys Asp Thr Leu Met Ile Ser Arg Thr
                20                  25                  30

Pro Glu Val Thr Cys Val Val Asp Val Ser Gln Glu Asp Pro Glu
            35                  40                  45

Val Gln Phe Asn Trp Tyr Val Asp Gly Val Glu Val His Asn Ala Lys
 50                  55                  60

Thr Lys Pro Arg Glu Glu Gln Phe Asn Ser Thr Tyr Arg Val Val Ser
 65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Gln Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175
```

-continued

```
Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Ala
    210                 215                 220

Lys Ala Thr Thr Ala Pro Ala Thr Thr Arg Asn Thr Gly Arg Gly Gly
225                 230                 235                 240

Glu Glu Lys Lys Lys Glu Lys Glu Lys Glu Glu Gln Glu His Pro Ile
                245                 250                 255

Pro Asp Ser Ser Pro Leu Leu Gln Phe Gly Gly Gln Val Arg Gln Arg
            260                 265                 270

Tyr Leu Tyr Thr Asp Asp Ala Gln Gln Thr Glu Ala His Leu Glu Ile
        275                 280                 285

Arg Glu Asp Gly Thr Val Gly Gly Ala Ala Asp Gln Ser Pro Glu Ser
    290                 295                 300

Leu Leu Gln Leu Lys Ala Leu Lys Pro Gly Val Ile Gln Ile Leu Gly
305                 310                 315                 320

Val Lys Thr Ser Arg Phe Leu Cys Gln Arg Pro Asp Gly Ala Leu Tyr
                325                 330                 335

Gly Ser Leu His Phe Asp Pro Glu Ala Cys Ser Phe Arg Glu Glu Ile
            340                 345                 350

Arg Pro Asp Gly Tyr Asn Val Tyr Gln Ser Glu Ala His Gly Leu Pro
        355                 360                 365

Leu His Leu Pro Gly Asn Lys Ser Pro His Arg Asp Pro Ala Pro Arg
    370                 375                 380

Gly Pro Ala Arg Phe Leu Pro Leu Pro Gly Leu Pro Pro Ala Leu Pro
385                 390                 395                 400

Glu Pro Pro Gly Ile Leu Ala Pro Gln Pro Pro Asp Val Gly Ser Ser
                405                 410                 415

Asp Pro Leu Ser Met Val Thr Gly Leu Glu Ala Val Arg Ser Pro Ser
            420                 425                 430

Tyr Ala Ser
        435

<210> SEQ ID NO 28
<211> LENGTH: 422
<212> TYPE: PRT
<213> ORGANISM: Artificial Sequence
<220> FEATURE:
<223> OTHER INFORMATION: modified FGF21 variant connected to hybrid Fc

<400> SEQUENCE: 28

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95
```

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Gln Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
            195                 200                 205

His Asn His Tyr Thr Gln Lys Ser Leu Ser Leu Ser Leu Gly Lys Ala
            210                 215                 220

Lys Ala Thr Thr Ala Pro Ala Thr Thr Arg Asn Thr Gly Arg Gly Gly
225                 230                 235                 240

His Pro Ile Pro Asp Ser Ser Pro Leu Leu Gln Phe Gly Gly Gln Val
                245                 250                 255

Arg Gln Arg Tyr Leu Tyr Thr Asp Asp Ala Gln Gln Thr Glu Ala His
            260                 265                 270

Leu Glu Ile Arg Glu Asp Gly Thr Val Gly Gly Ala Ala Asp Gln Ser
            275                 280                 285

Pro Glu Ser Leu Leu Gln Leu Lys Ala Leu Lys Pro Gly Val Ile Gln
            290                 295                 300

Ile Leu Gly Val Lys Thr Ser Arg Phe Leu Cys Gln Arg Pro Asp Gly
305                 310                 315                 320

Ala Leu Tyr Gly Ser Leu His Phe Asp Pro Glu Ala Cys Ser Phe Arg
                325                 330                 335

Glu Leu Leu Leu Glu Asp Gly Tyr Asn Val Tyr Gln Ser Glu Ala His
            340                 345                 350

Gly Leu Pro Leu His Leu Pro Gly Asn Lys Ser Pro His Arg Asp Pro
            355                 360                 365

Ala Pro Arg Gly Pro Ala Arg Phe Leu Pro Leu Pro Gly Leu Pro Pro
            370                 375                 380

Ala Leu Pro Glu Pro Pro Gly Ile Leu Ala Pro Gln Pro Pro Asp Val
385                 390                 395                 400

Gly Ser Ser Asp Pro Leu Ser Met Val Thr Gly Leu Glu Ala Val Arg
                405                 410                 415

Ser Pro Ser Tyr Ala Ser
            420

<210> SEQ ID NO 29
<211> LENGTH: 420
<212> TYPE: PRT
<213> ORGANISM: Artificial Sequence
<220> FEATURE:
<223> OTHER INFORMATION: modified FGF21 variant connected to hybrid Fc

<400> SEQUENCE: 29

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

```
Pro Glu Val Thr Cys Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Ser Gly Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Leu
                325                 330                 335

Leu Leu Glu Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
    370                 375                 380

Pro Glu Pro Pro Gly Ile Leu Ala Pro Gln Pro Pro Asp Val Gly Ser
385                 390                 395                 400

Ser Asp Pro Leu Ser Met Val Thr Gly Leu Glu Ala Val Arg Ser Pro
                405                 410                 415

Ser Tyr Ala Ser
            420

<210> SEQ ID NO 30
<211> LENGTH: 420
```

<212> TYPE: PRT
<213> ORGANISM: Artificial Sequence
<220> FEATURE:
<223> OTHER INFORMATION: modified FGF21 variant connected to hybrid Fc

<400> SEQUENCE: 30

```
Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
    195                 200                 205

His Asn His Tyr Thr Gln Lys Ser Leu Ser Leu Ser Leu Gly Lys Gly
    210                 215                 220

Gly Gly Gly Ser Gly Gly Gly Ser Gly Gly Gly Ser His Pro
225                 230                 235                 240

Ile Pro Asp Ser Ser Pro Leu Leu Gln Phe Gly Gly Gln Val Arg Gln
            245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Leu
                325                 330                 335

Leu Leu Glu Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
    370                 375                 380
```

-continued

```
Pro Glu Pro Pro Gly Ile Leu Ala Pro Gln Pro Asp Val Gly Ser
385                 390                 395                 400

Ser Asp Pro Leu Ser Met Val Thr Gly Leu Glu Ala Asn Arg Ser Pro
            405                 410                 415

Ser Tyr Ala Ser
            420

<210> SEQ ID NO 31
<211> LENGTH: 419
<212> TYPE: PRT
<213> ORGANISM: Artificial Sequence
<220> FEATURE:
<223> OTHER INFORMATION: modified FGF21 variant connected to hybrid Fc

<400> SEQUENCE: 31

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
                20                  25                  30

Pro Glu Val Thr Cys Val Val Asp Val Ser Gln Glu Asp Pro Glu
            35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Gln Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Gly Ser Gly Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320
```

-continued

```
Tyr Gly Ser Leu His Phe Asp Pro Glu Ala Cys Ser Phe Arg Glu Leu
            325                 330                 335

Leu Leu Glu Asp Gly Tyr Asn Val Tyr Gln Ser Glu Ala His Gly Leu
        340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
    370                 375                 380

Pro Glu Pro Pro Gly Ile Leu Ala Pro Gln Pro Pro Asp Val Gly Ser
385                 390                 395                 400

Ser Asp Pro Leu Ser Met Val Asn Pro Ser Gln Gly Arg Ser Pro Ser
                405                 410                 415

Tyr Ala Ser

<210> SEQ ID NO 32
<211> LENGTH: 419
<212> TYPE: PRT
<213> ORGANISM: Artificial Sequence
<220> FEATURE:
<223> OTHER INFORMATION: modified FGF21 variant connected to hybrid Fc

<400> SEQUENCE: 32

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser Gln Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Gln Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Ser Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
```

```
                260                 265                 270
Ile Arg Glu Asp Gly Thr Val Gly Ala Ala Asp Gln Ser Pro Glu
            275                 280                 285

Ser Leu Leu Gln Leu Lys Ala Leu Lys Pro Gly Val Ile Gln Ile Leu
        290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Leu
                325                 330                 335

Leu Leu Glu Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
370                 375                 380

Pro Glu Pro Pro Gly Ile Leu Ala Pro Gln Pro Pro Asp Val Gly Ser
385                 390                 395                 400

Ser Asp Pro Leu Ser Met Val Asn Pro Ser Gln Gly Arg Ser Pro Ser
                405                 410                 415

Tyr Ala Ser

<210> SEQ ID NO 33
<211> LENGTH: 419
<212> TYPE: PRT
<213> ORGANISM: Artificial Sequence
<220> FEATURE:
<223> OTHER INFORMATION: modified FGF21 variant connected to hybrid Fc

<400> SEQUENCE: 33

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205
```

His Asn His Tyr Thr Gln Lys Ser Leu Ser Leu Ser Leu Gly Lys Gly
        210                 215                 220

Gly Gly Gly Ser Gly Gly Gly Gly Ser Gly Gly Gly Gly Ser His Pro
225                 230                 235                 240

Ile Pro Asp Ser Ser Pro Leu Leu Gln Phe Gly Gly Gln Val Arg Gln
            245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Leu
            325                 330                 335

Leu Leu Glu Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
    370                 375                 380

Pro Glu Pro Pro Gly Ile Leu Ala Pro Gln Pro Pro Asp Val Gly Ser
385                 390                 395                 400

Ser Asp Pro Leu Ser Met Val Gly Pro Ser Gln Asn Arg Ser Pro Ser
            405                 410                 415

Tyr Ala Ser

<210> SEQ ID NO 34
<211> LENGTH: 419
<212> TYPE: PRT
<213> ORGANISM: Artificial Sequence
<220> FEATURE:
<223> OTHER INFORMATION: modified FGF21 variant connected to hybrid Fc

<400> SEQUENCE: 34

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
            85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

```
Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Ser Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Leu
                325                 330                 335

Leu Leu Glu Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
    370                 375                 380

Pro Glu Pro Pro Gly Ile Leu Ala Pro Gln Pro Pro Asp Val Gly Ser
385                 390                 395                 400

Ser Asp Pro Leu Ser Met Val Gly Pro Ser Gln Gly Arg Ser Pro Ser
                405                 410                 415

Tyr Ala Ser

<210> SEQ ID NO 35
<211> LENGTH: 420
<212> TYPE: PRT
<213> ORGANISM: Artificial Sequence
<220> FEATURE:
<223> OTHER INFORMATION: modified FGF21 variant connected to hybrid Fc

<400> SEQUENCE: 35

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser Gln Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
```

```
                    85                  90                  95

Cys Lys Val Ser Asn Lys Gly Leu Pro Ser Ser Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Gln Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Gly Ser Gly Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Glu
                325                 330                 335

Ile Arg Pro Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
    370                 375                 380

Pro Glu Pro Pro Gly Ile Leu Ala Pro Gln Pro Pro Asp Val Gly Ser
385                 390                 395                 400

Ser Asp Pro Leu Ser Met Val Thr Gly Leu Glu Ala Val Arg Ser Pro
                405                 410                 415

Ser Tyr Ala Ser
            420

<210> SEQ ID NO 36
<211> LENGTH: 420
<212> TYPE: PRT
<213> ORGANISM: Artificial Sequence
<220> FEATURE:
<223> OTHER INFORMATION: modified FGF21 variant connected to hybrid Fc

<400> SEQUENCE: 36

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
```

-continued

Pro Glu Val Thr Cys Val Val Asp Val Ser Gln Glu Asp Pro Glu
         20                  25                  30

Val Gln Phe Asn Trp Tyr Val Asp Gly Val Glu Val His Asn Ala Lys
         35                  40                  45

Thr Lys Pro Arg Glu Glu Gln Phe Asn Ser Thr Tyr Arg Val Val Ser
 65              70                  75                  80

Val Leu Thr Val Leu His Gln Asp Trp Leu Asn Gly Lys Glu Tyr Lys
                     85                  90                  95

Cys Lys Val Ser Asn Lys Gly Leu Pro Ser Ser Ile Glu Lys Thr Ile
                 100                 105                 110

Ser Lys Ala Lys Gly Gln Pro Arg Glu Pro Gln Val Tyr Thr Leu Pro
             115                 120                 125

Pro Ser Gln Glu Glu Met Thr Lys Asn Gln Val Ser Leu Thr Cys Leu
         130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                 165                 170                 175

Asp Gly Ser Phe Phe Leu Tyr Ser Arg Leu Thr Val Asp Lys Ser Arg
             180                 185                 190

Trp Gln Glu Gly Asn Val Phe Ser Cys Ser Val Met His Glu Ala Leu
         195                 200                 205

His Asn His Tyr Thr Gln Lys Ser Leu Ser Leu Ser Leu Gly Lys Gly
     210                 215                 220

Gly Gly Gly Ser Gly Gly Gly Ser Gly Gly Gly Gly Ser His Pro
225                 230                 235                 240

Ile Pro Asp Ser Ser Pro Leu Leu Gln Phe Gly Gly Gln Val Arg Gln
                 245                 250                 255

Arg Tyr Leu Tyr Thr Asp Asp Ala Gln Gln Thr Glu Ala His Leu Glu
             260                 265                 270

Ile Arg Glu Asp Gly Thr Val Gly Gly Ala Ala Asp Gln Ser Pro Glu
         275                 280                 285

Ser Leu Leu Gln Leu Lys Ala Leu Lys Pro Gly Val Ile Gln Ile Leu
     290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Glu
                 325                 330                 335

Ile Arg Pro Asp Gly Tyr Asn Val Tyr Gln Ser Glu Ala His Gly Leu
             340                 345                 350

Pro Leu His Leu Pro Gly Asn Lys Ser Pro His Arg Asp Pro Ala Pro
         355                 360                 365

Arg Gly Pro Ala Arg Phe Leu Pro Leu Pro Gly Leu Pro Pro Ala Leu
     370                 375                 380

Pro Glu Pro Pro Gly Ile Leu Ala Pro Gln Pro Pro Asp Val Gly Ser
385                 390                 395                 400

Ser Asp Pro Leu Ser Met Val Thr Gly Leu Glu Ala Val Arg Ser Pro
                 405                 410                 415

Ser Tyr Glu Ser
         420

<210> SEQ ID NO 37

<211> LENGTH: 420
<212> TYPE: PRT
<213> ORGANISM: Artificial Sequence
<220> FEATURE:
<223> OTHER INFORMATION: modified FGF21 variant connected to hybrid Fc

<400> SEQUENCE: 37

```
Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Gly Ser Gly Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Glu
                325                 330                 335

Ile Arg Pro Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
    370                 375                 380
```

Pro Glu Pro Pro Gly Ile Leu Ala Pro Gln Pro Pro Asp Val Gly Ser
385                 390                 395                 400

Ser Asp Pro Leu Ser Met Val Thr Gly Leu Glu Ala Asn Arg Ser Pro
            405                 410                 415

Ser Tyr Glu Ser
            420

<210> SEQ ID NO 38
<211> LENGTH: 419
<212> TYPE: PRT
<213> ORGANISM: Artificial Sequence
<220> FEATURE:
<223> OTHER INFORMATION: modified FGF21 variant connected to hybrid Fc

<400> SEQUENCE: 38

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
                20                  25                  30

Pro Glu Val Thr Cys Val Val Asp Val Ser Gln Glu Asp Pro Glu
            35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Gln Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Ser Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

```
Tyr Gly Ser Leu His Phe Asp Pro Glu Ala Cys Ser Phe Arg Glu Glu
                325                 330                 335

Ile Arg Pro Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
    370                 375                 380

Pro Glu Pro Pro Gly Ile Leu Ala Pro Gln Pro Pro Asp Val Gly Ser
385                 390                 395                 400

Ser Asp Pro Leu Ser Met Val Asn Pro Ser Gln Gly Arg Ser Pro Ser
                405                 410                 415

Tyr Ala Ser

<210> SEQ ID NO 39
<211> LENGTH: 419
<212> TYPE: PRT
<213> ORGANISM: Artificial Sequence
<220> FEATURE:
<223> OTHER INFORMATION: modified FGF21 variant connected to hybrid Fc

<400> SEQUENCE: 39

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Ser Gly Gly Gly Ser His Pro
225                 230                 235                 240

Ile Pro Asp Ser Ser Pro Leu Leu Gln Phe Gly Gly Gln Val Arg Gln
                245                 250                 255
```

```
Arg Tyr Leu Tyr Thr Asp Asp Ala Gln Gln Thr Glu Ala His Leu Glu
                260                 265                 270

Ile Arg Glu Asp Gly Thr Val Gly Gly Ala Ala Asp Gln Ser Pro Glu
            275                 280                 285

Ser Leu Leu Gln Leu Lys Ala Leu Lys Pro Gly Val Ile Gln Ile Leu
        290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Glu
                325                 330                 335

Ile Arg Pro Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
370                 375                 380

Pro Glu Pro Pro Gly Ile Leu Ala Pro Gln Pro Pro Asp Val Gly Ser
385                 390                 395                 400

Ser Asp Pro Leu Ser Met Val Asn Pro Ser Gln Gly Arg Ser Pro Ser
                405                 410                 415

Tyr Glu Ser

<210> SEQ ID NO 40
<211> LENGTH: 423
<212> TYPE: PRT
<213> ORGANISM: Artificial Sequence
<220> FEATURE:
<223> OTHER INFORMATION: REG(Amgen)

<400> SEQUENCE: 40

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
```

```
                195                 200                 205
His Glu Ala Leu His Asn His Tyr Thr Gln Lys Ser Leu Ser Leu Ser
            210                 215                 220

Pro Gly Lys Gly Gly Gly Ser Gly Gly Gly Ser Gly Gly Gly
225                 230                 235                 240

Gly Ser His Pro Ile Pro Asp Ser Ser Pro Leu Leu Gln Phe Gly Gly
                245                 250                 255

Gln Val Arg Gln Arg Tyr Leu Tyr Thr Asp Asp Ala Gln Gln Thr Glu
            260                 265                 270

Ala His Leu Glu Ile Arg Glu Asp Gly Thr Val Gly Gly Ala Ala Asp
        275                 280                 285

Gln Ser Pro Glu Ser Leu Leu Gln Leu Lys Ala Leu Lys Pro Gly Val
    290                 295                 300

Ile Gln Ile Leu Gly Val Lys Thr Ser Arg Phe Leu Cys Gln Arg Pro
305                 310                 315                 320

Asp Gly Ala Leu Tyr Gly Ser Leu His Phe Asp Pro Glu Ala Cys Ser
                325                 330                 335

Phe Arg Glu Arg Leu Leu Glu Asp Gly Tyr Asn Val Tyr Gln Ser Glu
            340                 345                 350

Ala His Gly Leu Pro Leu His Leu Pro Gly Asn Lys Ser Pro His Arg
        355                 360                 365

Asp Pro Ala Pro Arg Gly Pro Ala Arg Phe Leu Pro Leu Pro Gly Leu
    370                 375                 380

Pro Pro Ala Leu Pro Glu Pro Gly Ile Leu Ala Pro Gln Pro Pro
385                 390                 395                 400

Asp Val Gly Ser Ser Asp Pro Leu Ser Met Val Gly Gly Ser Gln Gly
                405                 410                 415

Arg Ser Pro Ser Tyr Glu Ser
            420

<210> SEQ ID NO 41
<211> LENGTH: 424
<212> TYPE: PRT
<213> ORGANISM: Artificial Sequence
<220> FEATURE:
<223> OTHER INFORMATION: FGF21 connected to Fc(lilly)

<400> SEQUENCE: 41

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
```

```
            130                 135                 140
Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
210                 215                 220

Leu Ser Leu Gly Gly Gly Gly Ser Gly Gly Gly Ser Gly Gly
225                 230                 235                 240

Gly Gly Ser Ala His Pro Ile Pro Asp Ser Ser Pro Leu Leu Gln Phe
                245                 250                 255

Gly Gly Gln Val Arg Gln Arg Tyr Leu Tyr Thr Asp Asp Ala Gln Gln
            260                 265                 270

Thr Glu Cys His Leu Glu Ile Arg Glu Asp Gly Thr Val Gly Cys Ala
            275                 280                 285

Ala Asp Gln Ser Pro Glu Ser Leu Leu Gln Leu Lys Ala Leu Lys Pro
290                 295                 300

Gly Val Ile Gln Ile Leu Gly Val Lys Thr Ser Arg Phe Leu Cys Gln
305                 310                 315                 320

Arg Pro Asp Gly Ala Leu Tyr Gly Ser Leu His Phe Asp Pro Glu Ala
                325                 330                 335

Cys Ser Phe Arg Glu Asp Leu Lys Glu Asp Gly Tyr Asn Val Tyr Gln
            340                 345                 350

Ser Glu Ala His Gly Leu Pro Leu His Leu Pro Gly Asp Lys Ser Pro
            355                 360                 365

His Arg Lys Pro Ala Pro Arg Gly Pro Ala Arg Phe Leu Pro Leu Pro
370                 375                 380

Gly Leu Pro Pro Ala Leu Pro Glu Pro Gly Ile Leu Ala Pro Gln
385                 390                 395                 400

Pro Pro Asp Val Gly Ser Ser Asp Pro Leu Arg Leu Val Glu Pro Ser
                405                 410                 415

Gln Leu Arg Ser Pro Ser Phe Glu
            420

<210> SEQ ID NO 42
<211> LENGTH: 31
<212> TYPE: PRT
<213> ORGANISM: Artificial Sequence
<220> FEATURE:
<223> OTHER INFORMATION: GLP-1

<400> SEQUENCE: 42

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 43
<211> LENGTH: 31
<212> TYPE: PRT
<213> ORGANISM: Artificial Sequence
<220> FEATURE:
<223> OTHER INFORMATION: GLP-1 variant
```

-continued

<400> SEQUENCE: 43

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 44
<211> LENGTH: 31
<212> TYPE: PRT
<213> ORGANISM: Artificial Sequence
<220> FEATURE:
<223> OTHER INFORMATION: GLP-1 variant

<400> SEQUENCE: 44

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 45
<211> LENGTH: 31
<212> TYPE: PRT
<213> ORGANISM: Artificial Sequence
<220> FEATURE:
<223> OTHER INFORMATION: GLP-1 variant

<400> SEQUENCE: 45

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly
            20                  25                  30

<210> SEQ ID NO 46
<211> LENGTH: 31
<212> TYPE: PRT
<213> ORGANISM: Artificial Sequence
<220> FEATURE:
<223> OTHER INFORMATION: GLP-1 variant

<400> SEQUENCE: 46

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 47
<211> LENGTH: 245
<212> TYPE: PRT
<213> ORGANISM: Artificial Sequence
<220> FEATURE:
<223> OTHER INFORMATION: hybrid Fc5

<400> SEQUENCE: 47

Arg Asn Thr Gly Arg Gly Gly Glu Glu Lys Lys Glu Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

-continued

```
Ser Gln Glu Asp Pro Glu Val Gln Phe Asn Trp Tyr Val Asp Gly Val
 65                  70                  75                  80

Glu Val His Asn Ala Lys Thr Lys Pro Arg Glu Glu Gln Phe Asn Ser
             85                  90                  95

Thr Tyr Arg Val Val Ser Val Leu Thr Val Leu His Gln Asp Trp Leu
        100                 105                 110

Asn Gly Lys Glu Tyr Lys Cys Lys Val Ser Asn Lys Gly Leu Pro Ser
    115                 120                 125

Ser Ile Glu Lys Thr Ile Ser Lys Ala Lys Gly Gln Pro Arg Glu Pro
130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 48
<211> LENGTH: 233
<212> TYPE: PRT
<213> ORGANISM: Artificial Sequence
<220> FEATURE:
<223> OTHER INFORMATION: hybrid Fc40

<400> SEQUENCE: 48

Glu Lys Glu Lys Glu Glu Gln Glu Glu Arg Glu Thr Lys Thr Pro Glu
 1               5                  10                  15

Cys Pro Ser His Thr Gln Pro Leu Gly Val Phe Leu Phe Pro Pro Lys
             20                  25                  30

Pro Lys Asp Thr Leu Met Ile Ser Arg Thr Pro Glu Val Thr Cys Val
        35                  40                  45

Val Val Asp Val Ser Gln Glu Asp Pro Glu Val Gln Phe Asn Trp Tyr
    50                  55                  60

Val Asp Gly Val Glu Val His Asn Ala Lys Thr Lys Pro Arg Glu Glu
 65                  70                  75                  80

Gln Phe Asn Ser Thr Tyr Arg Val Val Ser Val Leu Thr Val Leu His
             85                  90                  95

Gln Asp Trp Leu Asn Gly Lys Glu Tyr Lys Cys Lys Val Ser Asn Lys
        100                 105                 110

Gly Leu Pro Ser Ser Ile Glu Lys Thr Ile Ser Lys Ala Lys Gly Gln
    115                 120                 125

Pro Arg Glu Pro Gln Val Tyr Thr Leu Pro Pro Ser Gln Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175
```

```
Tyr Lys Thr Thr Pro Pro Val Leu Asp Ser Asp Gly Ser Phe Phe Leu
            180             185                 190

Tyr Ser Arg Leu Thr Val Asp Lys Ser Arg Trp Gln Glu Gly Asn Val
        195                 200                 205

Phe Ser Cys Ser Val Met His Glu Ala Leu His Asn His Tyr Thr Gln
    210                 215                 220

Lys Ser Leu Ser Leu Ser Leu Gly Lys
225             230
```

<210> SEQ ID NO 49
<211> LENGTH: 276
<212> TYPE: PRT
<213> ORGANISM: Artificial Sequence
<220> FEATURE:
<223> OTHER INFORMATION: GLP-1 variant connected to hybrid Fc5

<400> SEQUENCE: 49

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Asn Thr Gly Arg Gly Gly Glu Glu Lys Lys Glu Lys Glu Lys Glu
        35                  40                  45

Glu Gln Glu Glu Arg Glu Thr Lys Thr Pro Glu Cys Pro Ser His Thr
50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys
        275
```

<210> SEQ ID NO 50
<211> LENGTH: 264

```
<212> TYPE: PRT
<213> ORGANISM: Artificial Sequence
<220> FEATURE:
<223> OTHER INFORMATION: GLP-1 variant connected to hybrid Fc40

<400> SEQUENCE: 50

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys
                260

<210> SEQ ID NO 51
<211> LENGTH: 276
<212> TYPE: PRT
<213> ORGANISM: Artificial Sequence
<220> FEATURE:
<223> OTHER INFORMATION: GLP-1 variant connected to hybrid Fc5

<400> SEQUENCE: 51

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro Glu Cys Pro Ser His Thr
    50                  55                  60
```

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys
        275

<210> SEQ ID NO 52
<211> LENGTH: 264
<212> TYPE: PRT
<213> ORGANISM: Artificial Sequence
<220> FEATURE:
<223> OTHER INFORMATION: GLP-1 variant connected to hybrid Fc40

<400> SEQUENCE: 52

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
130                 135                 140

```
Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys
            260

<210> SEQ ID NO 53
<211> LENGTH: 276
<212> TYPE: PRT
<213> ORGANISM: Artificial Sequence
<220> FEATURE:
<223> OTHER INFORMATION: GLP-1 variant connected to hybrid Fc5

<400> SEQUENCE: 53

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Arg
            20                  25                  30

Asn Thr Gly Arg Gly Gly Glu Lys Lys Lys Glu Lys Glu Lys Glu Glu
        35                  40                  45

Glu Gln Glu Glu Arg Glu Thr Lys Thr Pro Glu Cys Pro Ser His Thr
    50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240
```

```
Val Asp Lys Ser Arg Trp Gln Glu Gly Asn Val Phe Ser Cys Ser Val
            245                 250                 255

Met His Glu Ala Leu His Asn His Tyr Thr Gln Lys Ser Leu Ser Leu
        260                 265                 270

Ser Leu Gly Lys
        275
```

<210> SEQ ID NO 54
<211> LENGTH: 264
<212> TYPE: PRT
<213> ORGANISM: Artificial Sequence
<220> FEATURE:
<223> OTHER INFORMATION: GLP-1 variant connected to hybrid Fc40

<400> SEQUENCE: 54

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys
            260
```

<210> SEQ ID NO 55
<211> LENGTH: 276
<212> TYPE: PRT
<213> ORGANISM: Artificial Sequence
<220> FEATURE:
<223> OTHER INFORMATION: GLP-1 variant connected to hybrid Fc5

<400> SEQUENCE: 55

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Arg
            20                  25                  30

Asn Thr Gly Arg Gly Gly Glu Lys Lys Glu Lys Glu Lys Glu
        35                  40                  45

Glu Gln Glu Glu Arg Glu Thr Lys Thr Pro Glu Cys Pro Ser His Thr
    50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys
        275
```

<210> SEQ ID NO 56
<211> LENGTH: 264
<212> TYPE: PRT
<213> ORGANISM: Artificial Sequence
<220> FEATURE:
<223> OTHER INFORMATION: GLP-1 variant connected to hybrid Fc40

<400> SEQUENCE: 56

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
```

```
                65                  70                  75                  80
Val Asp Val Ser Gln Glu Asp Pro Glu Val Gln Phe Asn Trp Tyr Val
                    85                  90                  95

Asp Gly Val Glu Val His Asn Ala Lys Thr Lys Pro Arg Glu Glu Gln
                100                 105                 110

Phe Asn Ser Thr Tyr Arg Val Val Ser Val Leu Thr Val Leu His Gln
                115                 120                 125

Asp Trp Leu Asn Gly Lys Glu Tyr Lys Cys Lys Val Ser Asn Lys Gly
130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
                180                 185                 190

Asp Ile Ala Val Glu Trp Glu Ser Asn Gly Gln Pro Glu Asn Asn Tyr
                195                 200                 205

Lys Thr Thr Pro Pro Val Leu Asp Ser Asp Gly Ser Phe Phe Leu Tyr
210                 215                 220

Ser Arg Leu Thr Val Asp Lys Ser Arg Trp Gln Gln Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys
                260

<210> SEQ ID NO 57
<211> LENGTH: 275
<212> TYPE: PRT
<213> ORGANISM: Artificial Sequence
<220> FEATURE:
<223> OTHER INFORMATION: Dulaglutide

<400> SEQUENCE: 57

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Ser Gly Gly Gly Ser Ala Glu
            35                  40                  45

Ser Lys Tyr Gly Pro Pro Cys Pro Pro Cys Pro Ala Pro Glu Ala Ala
        50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
                100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
        130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
```

```
                165                 170                 175
Val Tyr Thr Leu Pro Ser Gln Glu Glu Met Thr Lys Asn Gln Val
                180                 185                 190

Ser Leu Thr Cys Leu Val Lys Gly Phe Tyr Pro Ser Asp Ile Ala Val
                195                 200                 205

Glu Trp Glu Ser Asn Gly Gln Pro Glu Asn Asn Tyr Lys Thr Thr Pro
        210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly
        275

<210> SEQ ID NO 58
<211> LENGTH: 461
<212> TYPE: PRT
<213> ORGANISM: Artificial Sequence
<220> FEATURE:
<223> OTHER INFORMATION: GLP1(A2G)-HyFc40-GS3-FGF21(EIRP, TGLEAV)

<400> SEQUENCE: 58

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Glu
                20                  25                  30

Lys Glu Lys Glu Glu Gln Glu Arg Glu Thr Lys Thr Pro Glu Cys
            35                  40                  45

Pro Ser His Thr Gln Pro Leu Gly Val Phe Leu Phe Pro Pro Lys Pro
        50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
                100                 105                 110

Phe Asn Ser Thr Tyr Arg Val Val Ser Val Leu Thr Val Leu His Gln
            115                 120                 125

Asp Trp Leu Asn Gly Lys Glu Tyr Lys Cys Lys Val Ser Asn Lys Gly
        130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
                180                 185                 190

Asp Ile Ala Val Glu Trp Glu Ser Asn Gly Gln Pro Glu Asn Asn Tyr
            195                 200                 205

Lys Thr Thr Pro Pro Val Leu Asp Ser Asp Gly Ser Phe Phe Leu Tyr
        210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
```

```
                245                 250                 255
Ser Leu Ser Leu Ser Leu Gly Lys Gly Gly Gly Ser Gly Gly Gly
            260                 265                 270

Gly Ser Gly Gly Gly Ser His Pro Ile Pro Asp Ser Ser Pro Leu
            275                 280                 285

Leu Gln Phe Gly Gly Gln Val Arg Gln Arg Tyr Leu Tyr Thr Asp Asp
    290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Arg Pro Asp Gly Ala Leu Tyr Gly Ser Leu His Phe Asp
            355                 360                 365

Pro Glu Ala Cys Ser Phe Arg Glu Ile Arg Pro Asp Gly Tyr Asn
            370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Gly Ile Leu
            420                 425                 430

Ala Pro Gln Pro Pro Asp Val Gly Ser Ser Asp Pro Leu Ser Met Val
            435                 440                 445

Thr Gly Leu Glu Ala Val Arg Ser Pro Ser Tyr Ala Ser
    450                 455                 460

<210> SEQ ID NO 59
<211> LENGTH: 473
<212> TYPE: PRT
<213> ORGANISM: Artificial Sequence
<220> FEATURE:
<223> OTHER INFORMATION: GLP1(GE)-HyFc5-GS3-FGF21(EIRP, TGLEAV)

<400> SEQUENCE: 59

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro Glu Cys Pro Ser His Thr
    50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
```

```
                145                 150                 155                 160
        Ile Glu Lys Thr Ile Ser Lys Ala Lys Gly Gln Pro Arg Glu Pro Gln
                        165                 170                 175

Val Tyr Thr Leu Pro Pro Ser Gln Glu Glu Met Thr Lys Asn Gln Val
                        180                 185                 190

Ser Leu Thr Cys Leu Val Lys Gly Phe Tyr Pro Ser Asp Ile Ala Val
                        195                 200                 205

Glu Trp Glu Ser Asn Gly Gln Pro Glu Asn Asn Tyr Lys Thr Thr Pro
                210                 215                 220

Pro Val Leu Asp Ser Asp Gly Ser Phe Phe Leu Tyr Ser Arg Leu Thr
        225                 230                 235                 240

Val Asp Lys Ser Arg Trp Gln Glu Gly Asn Val Phe Ser Cys Ser Val
                        245                 250                 255

Met His Glu Ala Leu His Asn His Tyr Thr Gln Lys Ser Leu Ser Leu
                        260                 265                 270

Ser Leu Gly Lys Gly Gly Gly Gly Ser Gly Gly Gly Ser Gly Gly
                275                 280                 285

Gly Gly Ser His Pro Ile Pro Asp Ser Ser Pro Leu Leu Gln Phe Gly
                290                 295                 300

Gly Gln Val Arg Gln Arg Tyr Leu Tyr Thr Asp Asp Ala Gln Gln Thr
        305                 310                 315                 320

Glu Ala His Leu Glu Ile Arg Glu Asp Gly Thr Val Gly Gly Ala Ala
                        325                 330                 335

Asp Gln Ser Pro Glu Ser Leu Leu Gln Leu Lys Ala Leu Lys Pro Gly
                        340                 345                 350

Val Ile Gln Ile Leu Gly Val Lys Thr Ser Arg Phe Leu Cys Gln Arg
                        355                 360                 365

Pro Asp Gly Ala Leu Tyr Gly Ser Leu His Phe Asp Pro Glu Ala Cys
                        370                 375                 380

Ser Phe Arg Glu Glu Ile Arg Pro Asp Gly Tyr Asn Val Tyr Gln Ser
        385                 390                 395                 400

Glu Ala His Gly Leu Pro Leu His Leu Pro Gly Asn Lys Ser Pro His
                        405                 410                 415

Arg Asp Pro Ala Pro Arg Gly Pro Ala Arg Phe Leu Pro Leu Pro Gly
                        420                 425                 430

Leu Pro Pro Ala Leu Pro Glu Pro Pro Gly Ile Leu Ala Pro Gln Pro
                        435                 440                 445

Pro Asp Val Gly Ser Ser Asp Pro Leu Ser Met Val Thr Gly Leu Glu
        450                 455                 460

Ala Val Arg Ser Pro Ser Tyr Ala Ser
        465                 470

<210> SEQ ID NO 60
<211> LENGTH: 461
<212> TYPE: PRT
<213> ORGANISM: Artificial Sequence
<220> FEATURE:
<223> OTHER INFORMATION: GLP1(GE)-HyFc40-GS3-FGF21(EIRP, TGLEAV)

<400> SEQUENCE: 60

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Glu
                20                  25                  30

Lys Glu Lys Glu Glu Gln Glu Glu Arg Glu Thr Lys Thr Pro Glu Cys
```

-continued

```
            35                  40                  45
Pro Ser His Thr Gln Pro Leu Gly Val Phe Leu Phe Pro Pro Lys Pro
            50                  55                  60
Lys Asp Thr Leu Met Ile Ser Arg Thr Pro Glu Val Thr Cys Val Val
 65                  70                  75                  80
Val Asp Val Ser Gln Glu Asp Pro Glu Val Gln Phe Asn Trp Tyr Val
                85                  90                  95
Asp Gly Val Glu Val His Asn Ala Lys Thr Lys Pro Arg Glu Glu Gln
               100                 105                 110
Phe Asn Ser Thr Tyr Arg Val Val Ser Val Leu Thr Val Leu His Gln
               115                 120                 125
Asp Trp Leu Asn Gly Lys Glu Tyr Lys Cys Lys Val Ser Asn Lys Gly
           130                 135                 140
Leu Pro Ser Ser Ile Glu Lys Thr Ile Ser Lys Ala Lys Gly Gln Pro
145                 150                 155                 160
Arg Glu Pro Gln Val Tyr Thr Leu Pro Pro Ser Gln Glu Glu Met Thr
               165                 170                 175
Lys Asn Gln Val Ser Leu Thr Cys Leu Val Lys Gly Phe Tyr Pro Ser
           180                 185                 190
Asp Ile Ala Val Glu Trp Glu Ser Asn Gly Gln Pro Glu Asn Asn Tyr
           195                 200                 205
Lys Thr Thr Pro Pro Val Leu Asp Ser Asp Gly Ser Phe Phe Leu Tyr
210                 215                 220
Ser Arg Leu Thr Val Asp Lys Ser Arg Trp Gln Glu Gly Asn Val Phe
225                 230                 235                 240
Ser Cys Ser Val Met His Glu Ala Leu His Asn His Tyr Thr Gln Lys
                245                 250                 255
Ser Leu Ser Leu Ser Leu Gly Lys Gly Gly Gly Ser Gly Gly Gly
            260                 265                 270
Gly Ser Gly Gly Gly Gly Ser His Pro Ile Pro Asp Ser Ser Pro Leu
            275                 280                 285
Leu Gln Phe Gly Gly Gln Val Arg Gln Arg Tyr Leu Tyr Thr Asp Asp
            290                 295                 300
Ala Gln Gln Thr Glu Ala His Leu Glu Ile Arg Glu Asp Gly Thr Val
305                 310                 315                 320
Gly Gly Ala Ala Asp Gln Ser Pro Glu Ser Leu Leu Gln Leu Lys Ala
                325                 330                 335
Leu Lys Pro Gly Val Ile Gln Ile Leu Gly Val Lys Thr Ser Arg Phe
            340                 345                 350
Leu Cys Gln Arg Pro Asp Gly Ala Leu Tyr Gly Ser Leu His Phe Asp
            355                 360                 365
Pro Glu Ala Cys Ser Phe Arg Glu Glu Ile Arg Pro Asp Gly Tyr Asn
            370                 375                 380
Val Tyr Gln Ser Glu Ala His Gly Leu Pro Leu His Leu Pro Gly Asn
385                 390                 395                 400
Lys Ser Pro His Arg Asp Pro Ala Pro Arg Gly Pro Ala Arg Phe Leu
                405                 410                 415
Pro Leu Pro Gly Leu Pro Pro Ala Leu Pro Glu Pro Pro Gly Ile Leu
            420                 425                 430
Ala Pro Gln Pro Pro Asp Val Gly Ser Ser Asp Pro Leu Ser Met Val
            435                 440                 445
Thr Gly Leu Glu Ala Val Arg Ser Pro Ser Tyr Ala Ser
            450                 455                 460
```

<210> SEQ ID NO 61
<211> LENGTH: 473
<212> TYPE: PRT
<213> ORGANISM: Artificial Sequence
<220> FEATURE:
<223> OTHER INFORMATION: GLP1(GG)-HyFc5-GS3-FGF21(EIRP, TGLEAV)

<400> SEQUENCE: 61

| | | | | | | | | | | | | | | |
|---|---|---|---|---|---|---|---|---|---|---|---|---|---|---|
| His | Gly | Glu | Gly | Thr | Phe | Thr | Ser | Asp | Val | Ser | Ser | Tyr | Leu | Glu | Gly |
| 1 | | | | 5 | | | | | 10 | | | | | 15 | |
| Gln | Ala | Ala | Lys | Glu | Phe | Ile | Ala | Trp | Leu | Val | Lys | Gly | Gly | Gly | Arg |
| | | | 20 | | | | | 25 | | | | | 30 | | |
| Asn | Thr | Gly | Arg | Gly | Gly | Glu | Glu | Lys | Lys | Lys | Glu | Lys | Glu | Lys | Glu |
| | | | 35 | | | | | 40 | | | | | 45 | | |
| Glu | Gln | Glu | Glu | Arg | Glu | Thr | Lys | Thr | Pro | Glu | Cys | Pro | Ser | His | Thr |
| | 50 | | | | | 55 | | | | | 60 | | | | |
| Gln | Pro | Leu | Gly | Val | Phe | Leu | Phe | Pro | Pro | Lys | Pro | Lys | Asp | Thr | Leu |
| 65 | | | | | 70 | | | | | 75 | | | | | 80 |
| Met | Ile | Ser | Arg | Thr | Pro | Glu | Val | Thr | Cys | Val | Val | Val | Asp | Val | Ser |
| | | | | 85 | | | | | 90 | | | | | 95 | |
| Gln | Glu | Asp | Pro | Glu | Val | Gln | Phe | Asn | Trp | Tyr | Val | Asp | Gly | Val | Glu |
| | | | 100 | | | | | 105 | | | | | 110 | | |
| Val | His | Asn | Ala | Lys | Thr | Lys | Pro | Arg | Glu | Glu | Gln | Phe | Asn | Ser | Thr |
| | | | 115 | | | | | 120 | | | | | 125 | | |
| Tyr | Arg | Val | Val | Ser | Val | Leu | Thr | Val | Leu | His | Gln | Asp | Trp | Leu | Asn |
| | 130 | | | | | 135 | | | | | 140 | | | | |
| Gly | Lys | Glu | Tyr | Lys | Cys | Lys | Val | Ser | Asn | Lys | Gly | Leu | Pro | Ser | Ser |
| 145 | | | | | 150 | | | | | 155 | | | | | 160 |
| Ile | Glu | Lys | Thr | Ile | Ser | Lys | Ala | Lys | Gly | Gln | Pro | Arg | Glu | Pro | Gln |
| | | | | 165 | | | | | 170 | | | | | 175 | |
| Val | Tyr | Thr | Leu | Pro | Pro | Ser | Gln | Glu | Glu | Met | Thr | Lys | Asn | Gln | Val |
| | | | 180 | | | | | 185 | | | | | 190 | | |
| Ser | Leu | Thr | Cys | Leu | Val | Lys | Gly | Phe | Tyr | Pro | Ser | Asp | Ile | Ala | Val |
| | | | 195 | | | | | 200 | | | | | 205 | | |
| Glu | Trp | Glu | Ser | Asn | Gly | Gln | Pro | Glu | Asn | Asn | Tyr | Lys | Thr | Thr | Pro |
| | 210 | | | | | 215 | | | | | 220 | | | | |
| Pro | Val | Leu | Asp | Ser | Asp | Gly | Ser | Phe | Phe | Leu | Tyr | Ser | Arg | Leu | Thr |
| 225 | | | | | 230 | | | | | 235 | | | | | 240 |
| Val | Asp | Lys | Ser | Arg | Trp | Gln | Glu | Gly | Asn | Val | Phe | Ser | Cys | Ser | Val |
| | | | | 245 | | | | | 250 | | | | | 255 | |
| Met | His | Glu | Ala | Leu | His | Asn | His | Tyr | Thr | Gln | Lys | Ser | Leu | Ser | Leu |
| | | | 260 | | | | | 265 | | | | | 270 | | |
| Ser | Leu | Gly | Lys | Gly | Gly | Gly | Gly | Ser | Gly | Gly | Gly | Ser | Gly | Gly |
| | | | 275 | | | | | 280 | | | | | 285 | | |
| Gly | Gly | Ser | His | Pro | Ile | Pro | Asp | Ser | Ser | Pro | Leu | Leu | Gln | Phe | Gly |
| | | | 290 | | | | | 295 | | | | | 300 | | |
| Gly | Gln | Val | Arg | Gln | Arg | Tyr | Leu | Tyr | Thr | Asp | Asp | Ala | Gln | Gln | Thr |
| 305 | | | | | 310 | | | | | 315 | | | | | 320 |
| Glu | Ala | His | Leu | Glu | Ile | Arg | Glu | Asp | Gly | Thr | Val | Gly | Gly | Ala | Ala |
| | | | | 325 | | | | | 330 | | | | | 335 | |
| Asp | Gln | Ser | Pro | Glu | Ser | Leu | Leu | Gln | Leu | Lys | Ala | Leu | Lys | Pro | Gly |
| | | | 340 | | | | | 345 | | | | | 350 | | |
| Val | Ile | Gln | Ile | Leu | Gly | Val | Lys | Thr | Ser | Arg | Phe | Leu | Cys | Gln | Arg |
| | | | 355 | | | | | 360 | | | | | 365 | | |

Pro Asp Gly Ala Leu Tyr Gly Ser Leu His Phe Asp Pro Glu Ala Cys
        370                 375                 380

Ser Phe Arg Glu Glu Ile Arg Pro Asp Gly Tyr Asn Val Tyr Gln Ser
385                 390                 395                 400

Glu Ala His Gly Leu Pro Leu His Leu Pro Gly Asn Lys Ser Pro His
                405                 410                 415

Arg Asp Pro Ala Pro Arg Gly Pro Ala Arg Phe Leu Pro Leu Pro Gly
                420                 425                 430

Leu Pro Pro Ala Leu Pro Glu Pro Pro Gly Ile Leu Ala Pro Gln Pro
        435                 440                 445

Pro Asp Val Gly Ser Ser Asp Pro Leu Ser Met Val Thr Gly Leu Glu
        450                 455                 460

Ala Val Arg Ser Pro Ser Tyr Ala Ser
465                 470

<210> SEQ ID NO 62
<211> LENGTH: 461
<212> TYPE: PRT
<213> ORGANISM: Artificial Sequence
<220> FEATURE:
<223> OTHER INFORMATION: GLP1(GG)-HyFc40-GS3-FGF21(EIRP, TGLEAV)

<400> SEQUENCE: 62

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Glu
                20                  25                  30

Lys Glu Lys Glu Glu Gln Glu Glu Arg Glu Thr Lys Thr Pro Glu Cys
            35                  40                  45

Pro Ser His Thr Gln Pro Leu Gly Val Phe Leu Phe Pro Pro Lys Pro
        50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
                100                 105                 110

Phe Asn Ser Thr Tyr Arg Val Val Ser Val Leu Thr Val Leu His Gln
            115                 120                 125

Asp Trp Leu Asn Gly Lys Glu Tyr Lys Cys Lys Val Ser Asn Lys Gly
        130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

```
Ser Leu Ser Leu Ser Leu Gly Lys Gly Gly Gly Ser Gly Gly Gly
            260                 265                 270

Gly Ser Gly Gly Gly Ser His Pro Ile Pro Asp Ser Ser Pro Leu
        275                 280                 285

Leu Gln Phe Gly Gln Val Arg Gln Arg Tyr Leu Tyr Thr Asp Asp
290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Arg Pro Asp Gly Ala Leu Tyr Gly Ser Leu His Phe Asp
            355                 360                 365

Pro Glu Ala Cys Ser Phe Arg Glu Glu Ile Arg Pro Asp Gly Tyr Asn
370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ser Met Val
            435                 440                 445

Thr Gly Leu Glu Ala Val Arg Ser Pro Ser Tyr Ala Ser
450                 455                 460

<210> SEQ ID NO 63
<211> LENGTH: 473
<212> TYPE: PRT
<213> ORGANISM: Artificial Sequence
<220> FEATURE:
<223> OTHER INFORMATION: GLP1(GEG)-HyFc5-GS3-FGF21(EIRP, TGLEAV)

<400> SEQUENCE: 63

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Arg
                20                  25                  30

Asn Thr Gly Arg Gly Gly Glu Glu Lys Lys Lys Glu Lys Glu Lys Glu
            35                  40                  45

Glu Gln Glu Glu Arg Glu Thr Lys Thr Pro Glu Cys Pro Ser His Thr
50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160
```

Ile Glu Lys Thr Ile Ser Lys Ala Lys Gly Gln Pro Arg Glu Pro Gln
            165                 170                 175

Val Tyr Thr Leu Pro Pro Ser Gln Glu Met Thr Lys Asn Gln Val
        180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
            245                 250                 255

Met His Glu Ala Leu His Asn His Tyr Thr Gln Lys Ser Leu Ser Leu
            260                 265                 270

Ser Leu Gly Lys Gly Gly Gly Ser Gly Gly Gly Ser Gly Gly
            275                 280                 285

Gly Gly Ser His Pro Ile Pro Asp Ser Ser Pro Leu Leu Gln Phe Gly
        290                 295                 300

Gly Gln Val Arg Gln Arg Tyr Leu Tyr Thr Asp Asp Ala Gln Gln Thr
305                 310                 315                 320

Glu Ala His Leu Glu Ile Arg Glu Asp Gly Thr Val Gly Gly Ala Ala
            325                 330                 335

Asp Gln Ser Pro Glu Ser Leu Leu Gln Leu Lys Ala Leu Lys Pro Gly
            340                 345                 350

Val Ile Gln Ile Leu Gly Val Lys Thr Ser Arg Phe Leu Cys Gln Arg
            355                 360                 365

Pro Asp Gly Ala Leu Tyr Gly Ser Leu His Phe Asp Pro Glu Ala Cys
        370                 375                 380

Ser Phe Arg Glu Glu Ile Arg Pro Asp Gly Tyr Asn Val Tyr Gln Ser
385                 390                 395                 400

Glu Ala His Gly Leu Pro Leu His Leu Pro Gly Asn Lys Ser Pro His
            405                 410                 415

Arg Asp Pro Ala Pro Arg Gly Pro Ala Arg Phe Leu Pro Leu Pro Gly
            420                 425                 430

Leu Pro Pro Ala Leu Pro Glu Pro Pro Gly Ile Leu Ala Pro Gln Pro
        435                 440                 445

Pro Asp Val Gly Ser Ser Asp Pro Leu Ser Met Val Thr Gly Leu Glu
    450                 455                 460

Ala Val Arg Ser Pro Ser Tyr Ala Ser
465                 470

<210> SEQ ID NO 64
<211> LENGTH: 461
<212> TYPE: PRT
<213> ORGANISM: Artificial Sequence
<220> FEATURE:
<223> OTHER INFORMATION: GLP1(GEG)-HyFc40-GS3-FGF21(EIRP, TGLEAV)

<400> SEQUENCE: 64

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Glu Arg Glu Thr Lys Thr Pro Glu Cys
        35                  40                  45

```
Pro Ser His Thr Gln Pro Leu Gly Val Phe Leu Phe Pro Pro Lys Pro
     50                  55                  60
Lys Asp Thr Leu Met Ile Ser Arg Thr Pro Glu Val Thr Cys Val Val
 65                  70                  75                  80
Val Asp Val Ser Gln Glu Asp Pro Glu Val Gln Phe Asn Trp Tyr Val
                     85                  90                  95
Asp Gly Val Glu Val His Asn Ala Lys Thr Lys Pro Arg Glu Glu Gln
                100                 105                 110
Phe Asn Ser Thr Tyr Arg Val Val Ser Val Leu Thr Val Leu His Gln
            115                 120                 125
Asp Trp Leu Asn Gly Lys Glu Tyr Lys Cys Lys Val Ser Asn Lys Gly
    130                 135                 140
Leu Pro Ser Ser Ile Glu Lys Thr Ile Ser Lys Ala Lys Gly Gln Pro
145                 150                 155                 160
Arg Glu Pro Gln Val Tyr Thr Leu Pro Pro Ser Gln Glu Glu Met Thr
                165                 170                 175
Lys Asn Gln Val Ser Leu Thr Cys Leu Val Lys Gly Phe Tyr Pro Ser
            180                 185                 190
Asp Ile Ala Val Glu Trp Glu Ser Asn Gly Gln Pro Glu Asn Asn Tyr
        195                 200                 205
Lys Thr Thr Pro Pro Val Leu Asp Ser Asp Gly Ser Phe Phe Leu Tyr
    210                 215                 220
Ser Arg Leu Thr Val Asp Lys Ser Arg Trp Gln Gln Gly Asn Val Phe
225                 230                 235                 240
Ser Cys Ser Val Met His Glu Ala Leu His Asn His Tyr Thr Gln Lys
                245                 250                 255
Ser Leu Ser Leu Ser Leu Gly Lys Gly Gly Gly Ser Gly Gly Gly
            260                 265                 270
Gly Ser Gly Gly Gly Gly Ser His Pro Ile Pro Asp Ser Ser Pro Leu
        275                 280                 285
Leu Gln Phe Gly Gly Gln Val Arg Gln Arg Tyr Leu Tyr Thr Asp Asp
    290                 295                 300
Ala Gln Gln Thr Glu Ala His Leu Glu Ile Arg Glu Asp Gly Thr Val
305                 310                 315                 320
Gly Gly Ala Ala Asp Gln Ser Pro Glu Ser Leu Leu Gln Leu Lys Ala
                325                 330                 335
Leu Lys Pro Gly Val Ile Gln Ile Leu Gly Val Lys Thr Ser Arg Phe
            340                 345                 350
Leu Cys Gln Arg Pro Asp Gly Ala Leu Tyr Gly Ser Leu His Phe Asp
        355                 360                 365
Pro Glu Ala Cys Ser Phe Arg Glu Ile Arg Pro Asp Gly Tyr Asn
    370                 375                 380
Val Tyr Gln Ser Glu Ala His Gly Leu Pro Leu His Leu Pro Gly Asn
385                 390                 395                 400
Lys Ser Pro His Arg Asp Pro Ala Pro Arg Gly Pro Ala Arg Phe Leu
                405                 410                 415
Pro Leu Pro Gly Leu Pro Pro Ala Leu Pro Glu Pro Pro Gly Ile Leu
            420                 425                 430
Ala Pro Gln Pro Pro Asp Val Gly Ser Ser Asp Pro Leu Ser Met Val
        435                 440                 445
Thr Gly Leu Glu Ala Val Arg Ser Pro Ser Tyr Ala Ser
    450                 455                 460
```

<210> SEQ ID NO 65
<211> LENGTH: 461
<212> TYPE: PRT
<213> ORGANISM: Artificial Sequence
<220> FEATURE:
<223> OTHER INFORMATION: GLP1(GEG)-HyFc40-GS3-FGF21(EIRP, TGLEAV, A180E)

<400> SEQUENCE: 65

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Gly Ser Gly Gly Gly
            260                 265                 270

Gly Ser Gly Gly Gly Gly Ser His Pro Ile Pro Asp Ser Ser Pro Leu
        275                 280                 285

Leu Gln Phe Gly Gly Gln Val Arg Gln Arg Tyr Leu Tyr Thr Asp Asp
    290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Arg Pro Asp Gly Ala Leu Tyr Gly Ser Leu His Phe Asp
        355                 360                 365
```

```
Pro Glu Ala Cys Ser Phe Arg Glu Glu Ile Arg Pro Asp Gly Tyr Asn
    370                 375                 380
Val Tyr Gln Ser Glu Ala His Gly Leu Pro Leu His Leu Pro Gly Asn
385                 390                 395                 400
Lys Ser Pro His Arg Asp Pro Ala Pro Arg Gly Pro Ala Arg Phe Leu
                405                 410                 415
Pro Leu Pro Gly Leu Pro Pro Ala Leu Pro Glu Pro Pro Gly Ile Leu
                420                 425                 430
Ala Pro Gln Pro Pro Asp Val Gly Ser Ser Asp Pro Leu Ser Met Val
                435                 440                 445
Thr Gly Leu Glu Ala Val Arg Ser Pro Ser Tyr Glu Ser
    450                 455                 460

<210> SEQ ID NO 66
<211> LENGTH: 461
<212> TYPE: PRT
<213> ORGANISM: Artificial Sequence
<220> FEATURE:
<223> OTHER INFORMATION: GLP1(GEG)-HyFc40-GS3-FGF21(EIRP, TGLEAN, A180E)

<400> SEQUENCE: 66

His Gly Glu Gly Thr Phe Thr Ser Asp Val Ser Ser Tyr Leu Glu Glu
1               5                   10                  15
Gln Ala Ala Lys Glu Phe Ile Ala Trp Leu Val Lys Gly Gly Gly Glu
                20                  25                  30
Lys Glu Lys Glu Glu Gln Glu Arg Glu Thr Lys Thr Pro Glu Cys
                35                  40                  45
Pro Ser His Thr Gln Pro Leu Gly Val Phe Leu Phe Pro Pro Lys Pro
    50                  55                  60
Lys Asp Thr Leu Met Ile Ser Arg Thr Pro Glu Val Thr Cys Val Val
65                  70                  75                  80
Val Asp Val Ser Gln Glu Asp Pro Glu Val Gln Phe Asn Trp Tyr Val
                85                  90                  95
Asp Gly Val Glu Val His Asn Ala Lys Thr Lys Pro Arg Glu Glu Gln
                100                 105                 110
Phe Asn Ser Thr Tyr Arg Val Val Ser Val Leu Thr Val Leu His Gln
                115                 120                 125
Asp Trp Leu Asn Gly Lys Glu Tyr Lys Cys Lys Val Ser Asn Lys Gly
    130                 135                 140
Leu Pro Ser Ser Ile Glu Lys Thr Ile Ser Lys Ala Lys Gly Gln Pro
145                 150                 155                 160
Arg Glu Pro Gln Val Tyr Thr Leu Pro Pro Ser Gln Glu Glu Met Thr
                165                 170                 175
Lys Asn Gln Val Ser Leu Thr Cys Leu Val Lys Gly Phe Tyr Pro Ser
                180                 185                 190
Asp Ile Ala Val Glu Trp Glu Ser Asn Gly Gln Pro Glu Asn Asn Tyr
                195                 200                 205
Lys Thr Thr Pro Pro Val Leu Asp Ser Asp Gly Ser Phe Phe Leu Tyr
    210                 215                 220
Ser Arg Leu Thr Val Asp Lys Ser Arg Trp Gln Glu Gly Asn Val Phe
225                 230                 235                 240
Ser Cys Ser Val Met His Glu Ala Leu His Asn His Tyr Thr Gln Lys
                245                 250                 255
Ser Leu Ser Leu Ser Leu Gly Lys Gly Gly Gly Ser Gly Gly Gly
                260                 265                 270
```

Gly Ser Gly Gly Gly Ser His Pro Ile Pro Asp Ser Ser Pro Leu
            275                 280                 285

Leu Gln Phe Gly Gly Gln Val Arg Gln Arg Tyr Leu Tyr Thr Asp Asp
        290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Arg Pro Asp Gly Ala Leu Tyr Gly Ser Leu His Phe Asp
        355                 360                 365

Pro Glu Ala Cys Ser Phe Arg Glu Glu Ile Arg Pro Asp Gly Tyr Asn
        370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ser Met Val
        435                 440                 445

Thr Gly Leu Glu Ala Asn Arg Ser Pro Ser Tyr Glu Ser
450                 455                 460

<210> SEQ ID NO 67
<211> LENGTH: 460
<212> TYPE: PRT
<213> ORGANISM: Artificial Sequence
<220> FEATURE:
<223> OTHER INFORMATION: GLP1(GEG)-HyFc40-GS3-FGF21(EIRP, G170N, A180E)

<400> SEQUENCE: 67

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

```
Lys Asn Gln Val Ser Leu Thr Cys Leu Val Lys Gly Phe Tyr Pro Ser
                180                 185                 190

Asp Ile Ala Val Glu Trp Glu Ser Asn Gly Gln Pro Glu Asn Asn Tyr
            195                 200                 205

Lys Thr Thr Pro Pro Val Leu Asp Ser Asp Gly Ser Phe Phe Leu Tyr
        210                 215                 220

Ser Arg Leu Thr Val Asp Lys Ser Arg Trp Gln Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Gly Ser Gly Gly Gly
                260                 265                 270

Gly Ser Gly Gly Gly Gly Ser His Pro Ile Pro Asp Ser Ser Pro Leu
                275                 280                 285

Leu Gln Phe Gly Gly Gln Val Arg Gln Arg Tyr Leu Tyr Thr Asp Asp
            290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
                340                 345                 350

Leu Cys Gln Arg Pro Asp Gly Ala Leu Tyr Gly Ser Leu His Phe Asp
            355                 360                 365

Pro Glu Ala Cys Ser Phe Arg Glu Glu Ile Arg Pro Asp Gly Tyr Asn
            370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ser Met Val
            435                 440                 445

Asn Pro Ser Gln Gly Arg Ser Pro Ser Tyr Glu Ser
            450                 455                 460

<210> SEQ ID NO 68
<211> LENGTH: 4
<212> TYPE: PRT
<213> ORGANISM: Artificial Sequence
<220> FEATURE:
<223> OTHER INFORMATION: FGF21 variant

<400> SEQUENCE: 68

Glu Ile Arg Pro
1

<210> SEQ ID NO 69
<211> LENGTH: 6
<212> TYPE: PRT
<213> ORGANISM: Artificial Sequence
<220> FEATURE:
<223> OTHER INFORMATION: FGF21 variant

<400> SEQUENCE: 69

Thr Gly Leu Glu Ala Val
1               5
```

<210> SEQ ID NO 70
<211> LENGTH: 6
<212> TYPE: PRT
<213> ORGANISM: Artificial Sequence
<220> FEATURE:
<223> OTHER INFORMATION: FGF21 variant

<400> SEQUENCE: 70

Thr Gly Leu Glu Ala Asn
1               5

<210> SEQ ID NO 71
<211> LENGTH: 1383
<212> TYPE: DNA
<213> ORGANISM: Artificial Sequence
<220> FEATURE:
<223> OTHER INFORMATION: nucleic acid molecule coding for DFD23

<400> SEQUENCE: 71

```
cacggcgagg ggaccttcac aagcgacgtg tcctcttatc tggaaggaca ggccgctaag    60
gagtttatcg catggctcgt caaaggcaga ggcgaaaagg agaaggaaga gcaggaggag   120
agagaaacca aacacccga gtgtcccagt cacactcagc ctctgggagt gtttctcttc   180
ccacctaagc ccaaggatac ccttatgatt tctaggacac tgaggtgac ctgcgtcgtt   240
gtggacgtga gtcaagagga cccagaggtc cagtttaact ggtatgttga cggcgtggaa   300
gtgcataatg caaaaactaa accccgcgag gaacaattca attcaaccta ccgggtcgtt   360
tctgtgttga cagtgctgca tcaagattgg ctgaacggga aggagtataa gtgtaaagtc   420
agtaataagg gactcccctc tagtatcgaa aaaactattt caaaggccaa aggccagcct   480
agagagccac aggtgtacac ccttcctcca tcccaagagg agatgacaaa gaaccaggtg   540
tctctgactt gtctcgtgaa ggggttctac cctagtgaca tcgctgtcga atgggagtca   600
aacggacagc cagagaataa ttataagaca actcctcccg ttctggattc tgacggcagc   660
ttctttctgt actctaggct tactgtggac aaaagtcgct ggcaagaagg gaacgtcttt   720
tcatgttctg ttatgcacga ggccttgcac aatcattata cacagaagtc tctgagtctc   780
tcactgggca aaggcggggg aggcagcggg ggaggcgggt ccggaggcgg gggatctcat   840
cccatccctg actccagtcc tctcctgcaa ttcggggggcc aagtccggca gcggtacctc   900
tacacagatg atgctcagca gacagaagcc cacctggaga tcagggagga tgggaccgtg   960
gggggcgctg ctgaccagag ccccgaaagt ctcctgcagc tgaaagcctt gaagcctgga  1020
gttattcaaa tcttgggagt caagactagt aggttcctgt gccagcggcc agatggggcc  1080
ctgtatggat ctctccattt tgaccctgag gcctgcagct tccggaggga gatcagaccc  1140
gacggataca atgtttacca gtccgaagcc cacggcctcc ctctgcatct gcccgggaac  1200
aagtctcctc accgggaccc tgcccccaga ggacctgctc gcttcctgcc actcccaggc  1260
ctgcccccg cattgcctga gccacccgga atcctggccc ccagcccc tgatgtggga  1320
tcctctgacc ctctgagcat ggtgacaggc ctggaggccg tgagaagccc cagctacgct  1380
tcc                                                              1383
```

<210> SEQ ID NO 72
<211> LENGTH: 1419
<212> TYPE: DNA
<213> ORGANISM: Artificial Sequence
<220> FEATURE:
<223> OTHER INFORMATION: nucleic acid molecule coding for DFD24

<400> SEQUENCE: 72

```
cacggcgagg ggaccttcac aagcgacgtg tcctcttacc tggaagagca ggccgctaag      60
gaatttatcg catggctcgt caaaggaaga gggaggaaca ccggacgggg cggggaagag     120
aagaagaaag aaaaggagaa ggaagagcag gaggagagag aaaccaaaac acccgagtgt     180
cccagtcaca ctcagcctct gggagtgttt ctcttcccac ctaagcccaa ggatacccett     240
atgatttcta ggacacctga ggtgacctgc gtcgttgtgg acgtgagtca agaggaccca     300
gaggtccagt ttaactggta tgttgacggc gtggaagtgc ataatgcaaa aactaaaccc     360
cgcgaggaac aattcaattc aacctaccgg gtcgtttctg tgttgacagt gctgcatcaa     420
gattggctga acgggaagga gtataagtgt aaagtcagta ataagggact ccctctagt     480
atcgaaaaaa ctatttcaaa ggccaaaggc cagcctagag agccacaggt gtacacccett     540
cctccatccc aagaggagat gacaaagaac caggtgtctc tgacttgtct cgtgaagggg     600
ttctacccta gtgacatcgc tgtcgaatgg gagtcaaacg gacagccaga gaataattat     660
aagacaactc ctcccgttct ggattctgac ggcagcttct ttctgtactc taggcttact     720
gtggacaaaa gtcgctggca agaagggaac gtctttcat gttctgttat gcacgaggcc     780
ttgcacaatc attatacaca gaagtctctg agtctctcac tgggcaaagg cggggaggc     840
agcggggag cgggtccgg aggcggggga tctcatccca tccctgactc cagtcctctc     900
ctgcaattcg ggggccaagt ccggcagcgg tacctctaca cagatgatgc tcagcagaca     960
gaagcccacc tggagatcag ggaggatggg accgtgggg cgctgctga ccagagcccc    1020
gaaagtctcc tgcagctgaa agccttgaag cctggagtta ttcaaatctt gggagtcaag    1080
actagtaggt tcctgtgcca gcggccagat ggggccctgt atggatctct ccattttgac    1140
cctgaggcct gcagcttccg ggaggagatc agacccgacg gatacaatgt ttaccagtcc    1200
gaagcccacg gcctccctct gcatctgccc gggaacaagt ctcctcaccg ggaccctgcc    1260
cccagaggac ctgctcgctt cctgccactc ccaggcctgc cccccgcatt gcctgagcca    1320
cccggaatcc tggccccca gcccctgat gtgggatcct ctgaccctct gagcatggtg    1380
acaggcctgg aggcgtgag aagccccagc tacgcttcc                            1419
```

<210> SEQ ID NO 73
<211> LENGTH: 1383
<212> TYPE: DNA
<213> ORGANISM: Artificial Sequence
<220> FEATURE:
<223> OTHER INFORMATION: nucleic acid molecule coding for DFD25

<400> SEQUENCE: 73

```
cacggcgagg ggaccttcac aagcgacgtg tcctcttacc tggaagagca ggccgctaag      60
gaatttatcg catggctcgt caaaggaaga gggaaaagg agaaggaaga gcaggaggag     120
agagaaacca aaacacccga gtgtcccagt cacactcagc ctctgggagt gtttctcttc     180
ccacctaagc ccaaggatac ccttatgatt tctaggacac ctgaggtgac ctgcgtcgtt     240
gtggacgtga gtcaagagga cccagaggtc cagtttaact ggtatgttga cggcgtggaa     300
gtgcataatg caaaaactaa accccgcgag gaacaattca attcaaccta ccgggtcgtt     360
tctgtgttga cagtgctgca tcaagattgg ctgaacggga aggagtataa gtgtaaagtc     420
agtaataagg gactcccctc tagtatcgaa aaaactattt caaaggccaa aggccagcct     480
agagagccac aggtgtacac ccttcctcca tcccaagagg agatgacaaa gaaccaggtg     540
```

```
tctctgactt gtctcgtgaa ggggttctac cctagtgaca tcgctgtcga atgggagtca      600
aacggacagc cagagaataa ttataagaca actcctcccg ttctggattc tgacggcagc      660
ttctttctgt actctaggct tactgtggac aaaagtcgct ggcaagaagg gaacgtcttt      720
tcatgttctg ttatgcacga ggccttgcac aatcattata cacagaagtc tctgagtctc      780
tcactgggca aaggcggggg aggcagcggg ggaggcgggt ccggaggcgg gggatctcat      840
cccatccctg actccagtcc tctcctgcaa ttcgggggcc aagtccggca gcggtacctc      900
tacacagatg atgctcagca gacagaagcc cacctggaga tcaggagga tgggaccgtg      960 gggggcgctg ctgaccagag ccccgaaagt ctcctgcagc tgaaagcctt gaagcctgga    1020
gttattcaaa tctttgggagt caagactagt aggttcctgt gccagcggcc agatgggcc    1080 ctgtatggat ctctccattt tgaccctgag gcctgcagct tccgggagga gatcagaccc    1140
gacggataca atgtttacca gtccgaagcc cacggcctcc ctctgcatct gcccgggaac    1200
aagtctcctc accgggaccc tgcccccaga ggacctgctc gcttcctgcc actcccaggc    1260 ctgcccccg cattgcctga gccacccgga atcctggccc ccagccccc tgatgtggga    1320 tcctctgacc ctctgagcat ggtgacaggc ctggaggccg tgagaagccc cagctacgct    1380
tcc                                                                   1383
```

<210> SEQ ID NO 74
<211> LENGTH: 1419
<212> TYPE: DNA
<213> ORGANISM: Artificial Sequence
<220> FEATURE:
<223> OTHER INFORMATION: nucleic acid molecule coding for DFD26

<400> SEQUENCE: 74

```
cacggcgagg ggaccttcac aagcgacgtg tcctcttatc tggaaggaca ggccgctaag     60
gagtttatcg catggctcgt caaaggcggc ggcaggaaca ccggacgggg cggggaagag    120
aagaagaaag aaaaggagaa ggaagagcag gaggagagag aaaccaaaac acccgagtgt    180
cccagtcaca ctcagcctct gggagtgttt ctcttccac ctaagcccaa ggatacccctt    240 atgatttcta ggacacctga ggtgacctgc gtcgttgtgg acgtgagtca agaggaccca    300
gaggtccagt ttaactggta tgttgacggc gtggaagtgc ataatgcaaa actaaaccc    360 cgcgaggaac aattcaattc aacctaccgg gtcgttctg tgttgacagt gctgcatcaa    420
gattggctga acgggaagga gtataagtgt aaagtcagta taagggact cccctctagt    480 atcgaaaaaa ctatttcaaa ggccaaaggc cagcctagag agccacaggt gtacacccct    540
cctccatccc aagaggagat gacaaagaac caggtgtctc tgacttgtct cgtgaagggg    600
ttctacccta gtgacatcgc tgtcgaatgg gagtcaaacg gacagccaga gaataattat    660
aagacaactc ctcccgttct ggattctgac ggcagcttct ttctgtactc taggcttact    720
gtggacaaaa gtcgctggca agaagggaac gtcttttcat gttctgttat gcacgaggcc    780
ttgcacaatc attatacaca gaagtctctg agtctctcac tgggcaaagg cgggggaggc    840 agcggggag gcgggtccgg aggcggggga tctcatccca tccctgactc agtcctctc    900 ctgcaattcg ggggccaagt ccggcagcgg tacctctaca cagatgatgc tcagcagaca    960
gaagcccacc tggagatcag ggaggatggg accgtggggg gcgctgctga ccagagcccc    1020
gaaagtctcc tgcagctgaa agccttgaag cctggagtta ttcaaatctt tgggagtcaag    1080 actagtaggt tcctgtgcca gcggccagat ggggccctgt atggatctct ccattttgac    1140
cctgaggcct gcagcttccg ggaggagatc agacccgacg gatacaatgt ttaccagtcc    1200
```

```
gaagcccacg gcctccctct gcatctgccc gggaacaagt ctcctcaccg ggaccctgcc   1260
cccagaggac ctgctcgctt cctgccactc ccaggcctgc cccccgcatt gcctgagcca   1320
cccggaatcc tggcccccca gcccctgat  gtgggatcct ctgaccctct gagcatggtg   1380
acaggcctgg aggccgtgag aagccccagc tacgcttcc                          1419
```

<210> SEQ ID NO 75
<211> LENGTH: 1383
<212> TYPE: DNA
<213> ORGANISM: Artificial Sequence
<220> FEATURE:
<223> OTHER INFORMATION: nucleic acid molecule coding for DFD27

<400> SEQUENCE: 75

```
cacggcgagg ggaccttcac aagcgacgtg tcctcttatc tggaaggaca ggccgctaag    60
gagtttatcg catggctcgt caaaggcggc ggcgaaaagg agaaggaaga gcaggaggag   120
agagaaacca aaacacccga gtgtcccagt cacactcagc ctctgggagt gtttctcttc   180
ccacctaagc ccaaggatac ccttatgatt tctaggacac ctgaggtgac ctgcgtcgtt   240
gtggacgtga gtcaagagga cccagaggtc cagtttaact ggtatgttga cggcgtggaa   300
gtgcataatg caaaaactaa accccgcgag gaacaattca attcaaccta ccgggtcgtt   360
tctgtgttga cagtgctgca tcaagattgg ctgaacggga aggagtataa gtgtaaagtc   420
agtaataagg gactcccctc tagtatcgaa aaaactattt caaaggccaa aggccagcct   480
agagagccac aggtgtacac ccttcctcca tcccaagagg agatgacaaa gaaccaggtg   540
tctctgactt gtctcgtgaa ggggttctac cctagtgaca tcgctgtcga atgggagtca   600
aacggacagc cagagaataa ttataagaca actcctcccg ttctggattc tgacggcagc   660
ttctttctgt actctaggct tactgtggac aaaagtcgct ggcaagaagg gaacgtcttt   720
tcatgttctg ttatgcacga ggccttgcac aatcattata cacagaagtc tctgagtctc   780
tcactgggca aaggcggggg aggcagcggg ggaggcgggt ccggaggcgg gggatctcat   840
cccatccctg actccagtcc tctcctgcaa ttcggggggcc aagtccggca gcggtacctc   900
tacacagatg atgctcagca gacagaagcc cacctggaga tcaggaggga tgggaccgtg   960 ggggggcgctg ctgaccagag ccccgaaagt ctcctgcagc tgaaagcctt gaagcctgga  1020
gttattcaaa tcttgggagt caagactagt aggttcctgt gccagcggcc agatggggcc  1080
ctgtatggat ctctccattt tgaccctgag gcctgcagct ccgggaagga gatcagaccc  1140
gacggataca atgtttacca gtccgaagcc cacgcctcc ctctgcatct gcccgggaac  1200
aagtctcctc accgggaccc tgccccaga ggacctgctc gcttcctgcc actcccaggc  1260 ctgcccccg cattgcctga ccacccgga atcctggccc ccagccccc tgatgtggga  1320 tcctctgacc ctctgagcat ggtgacaggc ctggaggccg tgagaagccc cagctacgct  1380
tcc                                                                1383
```

<210> SEQ ID NO 76
<211> LENGTH: 1419
<212> TYPE: DNA
<213> ORGANISM: Artificial Sequence
<220> FEATURE:
<223> OTHER INFORMATION: nucleic acid molecule coding for DFD28

<400> SEQUENCE: 76

```
cacggcgagg ggaccttcac aagcgacgtg tcctcttacc tggaagagca ggccgctaag    60
```

| | |
|---|---|
| gaatttatcg catggctcgt caaaggaggc gggaggaaca ccggacgggg cggggaagag | 120 |
| aagaagaaag aaaaggagaa ggaagagcag gaggagagag aaaccaaaac acccgagtgt | 180 |
| cccagtcaca ctcagcctct gggagtgttt ctcttcccac ctaagcccaa ggatacccct | 240 |
| atgatttcta ggacacctga ggtgacctgc gtcgttgtgg acgtgagtca agaggaccca | 300 |
| gaggtccagt ttaactggta tgttgacggc gtggaagtgc ataatgcaaa actaaaccc | 360 |
| cgcgaggaac aattcaattc aacctaccgg gtcgtttctg tgttgacagt gctgcatcaa | 420 |
| gattggctga acgggaagga gtataagtgt aaagtcagta ataagggact ccctctagt | 480 |
| atcgaaaaaa ctatttcaaa ggccaaaggc cagcctagag agccacaggt gtacacccctt | 540 |
| cctccatccc aagaggagat gacaaagaac caggtgtctc tgacttgtct cgtgaagggg | 600 |
| ttctacccta gtgacatcgc tgtcgaatgg gagtcaaacg gacagccaga gaataattat | 660 |
| aagacaactc ctcccgttct ggattctgac ggcagcttct ttctgtactc taggcttact | 720 |
| gtggacaaaa gtcgctggca agaagggaac gtcttttcat gttctgttat gcacgaggcc | 780 |
| ttgcacaatc attatacaca gaagtctctg agtctctcac tgggcaaagg cgggggaggc | 840 |
| agcgggggag gcgggtccgg aggcggggga tctcatccca tccctgactc cagtcctctc | 900 |
| ctgcaattcg ggggccaagt ccggcagcgg tacctctaca cagatgatgc tcagcagaca | 960 |
| gaagcccacc tggagatcag ggaggatggg accgtgggcg cgctgctga ccagagcccc | 1020 |
| gaaagtctcc tgcagctgaa agccttgaag cctggagtta ttcaaatctt gggagtcaag | 1080 |
| actagtaggt tcctgtgcca gcggccagat ggggccctgt atggatctct ccattttgac | 1140 |
| cctgaggcct gcagcttccg ggaggagatc agacccgacg gatacaatgt ttaccagtcc | 1200 |
| gaagcccacg gcctccctct gcatctgccc gggaacaagt ctcctcaccg ggaccctgcc | 1260 |
| cccagaggac ctgctcgctt cctgccactc ccaggcctgc cccccgcatt gcctgagcca | 1320 |
| cccggaatcc tggccccca gcccctgat gtgggatcct ctgaccctct gagcatggtg | 1380 |
| acaggcctgg aggccgtgag aagccccagc tacgcttcc | 1419 |

<210> SEQ ID NO 77
<211> LENGTH: 1383
<212> TYPE: DNA
<213> ORGANISM: Artificial Sequence
<220> FEATURE:
<223> OTHER INFORMATION: nucleic acid molecule coding for DFD29

<400> SEQUENCE: 77

| | |
|---|---|
| cacggcgagg ggaccttcac aagcgacgtg tcctcttacc tggaagagca ggccgctaag | 60 |
| gaatttatcg catggctcgt caaaggaggc ggggaaaagg agaaggaaga gcaggaggag | 120 |
| agagaaacca aaacacccga gtgtcccagt cacactcagc ctctgggagt gtttctcttc | 180 |
| ccacctaagc ccaaggatac ccttatgatt tctaggacac ctgaggtgac ctgcgtcgtt | 240 |
| gtggacgtga gtcaagagga cccagaggtc cagtttaact ggtatgttga cggcgtggaa | 300 |
| gtgcataatg caaaaactaa accccgcgag gaacaattca attcaaccta ccgggtcgtt | 360 |
| tctgtgttga cagtgctgca tcaagattgg ctgaacggga aggagtataa gtgtaaagtc | 420 |
| agtaataagg gactcccctc tagtatcgaa aaactatttt caaaggccaa aggccagcct | 480 |
| agagagccac aggtgtacac ccttcctcca tcccaagagg agatgacaaa gaaccaggtg | 540 |
| tctctgactt gtctcgtgaa ggggttctac cctagtgaca tcgctgtcga atgggagtca | 600 |
| aacggacagc cagagaataa ttataagaca actcctcccg ttctggattc tgacggcagc | 660 |
| ttctttctgt actctaggct tactgtggac aaaagtcgct ggcaagaagg gaacgtcttt | 720 |

-continued

```
tcatgttctg ttatgcacga ggccttgcac aatcattata cacagaagtc tctgagtctc      780
tcactgggca aaggcggggg aggcagcggg ggaggcgggt ccggaggcgg gggatctcat      840
cccatccctg actccagtcc tctcctgcaa ttcgggggcc aagtccggca gcggtacctc      900
tacacagatg atgctcagca gacagaagcc cacctggaga tcagggagga tgggaccgtg      960
gggggcgctg ctgaccagag ccccgaaagt ctcctgcagc tgaaagcctt gaagcctgga     1020
gttattcaaa tcttgggagt caagactagt aggttcctgt gccagcggcc agatggggcc     1080
ctgtatggat ctctccattt tgaccctgag gcctgcagct tccgggagga gatcagaccc     1140
gacggataca atgtttacca gtccgaagcc cacggcctcc ctctgcatct gcccgggaac     1200
aagtctcctc accgggaccc tgcccccaga ggacctgctc gcttcctgcc actcccaggc     1260 ctgcccccog cattgcctga gccacccgga atcctggccc ccagccccc tgatgtggga     1320 tcctctgacc ctctgagcat ggtgacaggc ctggaggccg tgagaagccc cagctacgct     1380
tcc                                                                  1383
```

<210> SEQ ID NO 78
<211> LENGTH: 1383
<212> TYPE: DNA
<213> ORGANISM: Artificial Sequence
<220> FEATURE:
<223> OTHER INFORMATION: nucleic acid molecule coding for DFD69

<400> SEQUENCE: 78

```
cacggcgagg ggaccttcac aagcgacgtg tcctcttacc tggaagagca ggccgctaag       60
gaatttatcg catggctcgt caaaggaggc ggggaaaagg agaaggaaga gcaggaggag      120
agagaaacca aaacacccga gtgtcccagt cacactcagc ctctgggagt gtttctcttc      180
ccacctaagc ccaaggatac ccttatgatt tctaggacac tgaggtgac  ctgcgtcgtt      240 gtggacgtga tcaagagga cccagaggtc cagtttaact ggtatgttga cggcgtggaa      300
gtgcataatg caaaaactaa accccgcgag gaacaattca attcaaccta ccgggtcgtt      360
tctgtgttga cagtgctgca tcaagattgg ctgaacggga aggagtataa gtgtaaagtc      420
agtaataagg gactcccctc tagtatcgaa aaaactattt caaaggccaa aggccagcct      480
agagagccac aggtgtacac ccttcctcca tcccaagagg agatgacaaa gaaccaggtg      540
tctctgactt gtctcgtgaa gggggttctac cctagtgaca tcgctgtcga atgggagtca      600
aacggacagc cagagaataa ttataagaca actcctcccg ttctggattc tgacggcagc      660
ttctttctgt actctaggct tactgtggac aaaagtcgct ggcaagaagg gaacgtcttt      720
tcatgttctg ttatgcacga ggccttgcac aatcattata cacagaagtc tctgagtctc      780
tcactgggca aaggcggggg aggcagcggg ggaggcgggt ccggaggcgg gggatctcat      840
cccatccctg actccagtcc tctcctgcaa ttcgggggcc aagtccggca gcggtacctc      900
tacacagatg atgctcagca gacagaagcc cacctggaga tcagggagga tgggaccgtg      960
gggggcgctg ctgaccagag ccccgaaagt ctcctgcagc tgaaagcctt gaagcctgga     1020
gttattcaaa tcttgggagt caagactagt aggttcctgt gccagcggcc agatggggcc     1080
ctgtatggat ctctccattt tgaccctgag gcctgcagct tccgggagga gatcagaccc     1140
gacggataca atgtttacca gtccgaagcc cacggcctcc ctctgcatct gcccgggaac     1200
aagtctcctc accgggaccc tgcccccaga ggacctgctc gcttcctgcc actcccaggc     1260 ctgcccccog cattgcctga gccacccgga atcctggccc ccagccccc tgatgtggga     1320
```

```
tcctctgacc ctctgagcat ggtgacaggc ctggaggccg tgagaagccc cagctacgag   1380
tcc                                                                 1383
```

<210> SEQ ID NO 79
<211> LENGTH: 1383
<212> TYPE: DNA
<213> ORGANISM: Artificial Sequence
<220> FEATURE:
<223> OTHER INFORMATION: nucleic acid molecule coding for DFD112

<400> SEQUENCE: 79

```
cacggcgagg ggaccttcac aagcgacgtg tcctcttacc tggaagagca ggccgctaag    60
gaatttatcg catggctcgt caaaggaggc ggggaaaagg agaaggaaga gcaggaggag   120
agagaaacca aaacacccga gtgtcccagt cacactcagc ctctgggagt gtttctcttc   180
ccacctaagc ccaaggatac ccttatgatt tctaggacac ctgaggtgac ctgcgtcgtt   240
gtggacgtga gtcaagagga cccagaggtc cagtttaact ggtatgttga cggcgtggaa   300
gtgcataatg caaaaactaa accccgcgag gaacaattca attcaaccta ccgggtcgtt   360
tctgtgttga cagtgctgca tcaagattgg ctgaacggga aggagtataa gtgtaaagtc   420
agtaataagg gactcccctc tagtatcgaa aaaactattt caaaggccaa aggccagcct   480
agagagccac aggtgtacac ccttcctcca tcccaagagg agatgacaaa gaaccaggtg   540
tctctgactt gtctcgtgaa ggggttctac cctagtgaca tcgctgtcga atgggagtca   600
aacggacagc cagagaataa ttataagaca actcctcccg ttctggattc tgacggcagc   660
ttctttctgt actctaggct tactgtggac aaaagtcgct ggcaagaagg gaacgtcttt   720
tcatgttctg ttatgcacga ggccttgcac aatcattata cacagaagtc tctgagtctc   780
tcactgggca aggcggggg aggcagcggg ggaggcgggt ccggaggcgg gggatctcat   840
cccatccctg actccagtcc tctcctgcaa ttcgggggcc aagtccggca gcggtacctc   900
tacacagatg atgctcagca gacagaagcc cacctggaga tcaggaggag tgggaccgtg   960
gggggcgctg ctgaccagag ccccgaaagt ctcctgcagc tgaaagcctt gaagcctgga  1020
gttattcaaa tcttgggagt caagactagt aggttcctgt gccagcggcc agatggggcc  1080
ctgtatggat ctctccattt tgaccctgag gcctgcagct tccgggagga gatcagaccc  1140
gacggataca tgtttaccag gtccgaagcc cacggcctcc ctctgcatct gcccgggaac  1200
aagtctcctc accgggaccc tgcccccaga ggacctgctc gcttcctgcc actcccaggc  1260 ctgcccccg cattgcctga gccaccggga atcctggccc ccagccccc tgatgtggga  1320 tcctctgacc ctctgagcat ggtgacaggc ctggaggcca acagaagccc cagctacgag  1380
tcc                                                                1383
```

<210> SEQ ID NO 80
<211> LENGTH: 1380
<212> TYPE: DNA
<213> ORGANISM: Artificial Sequence
<220> FEATURE:
<223> OTHER INFORMATION: nucleic acid molecule coding for DFD114

<400> SEQUENCE: 80

```
cacggcgagg ggaccttcac aagcgacgtg tcctcttacc tggaagagca ggccgctaag    60
gaatttatcg catggctcgt caaaggaggc ggggaaaagg agaaggaaga gcaggaggag   120
agagaaacca aaacacccga gtgtcccagt cacactcagc ctctgggagt gtttctcttc   180
ccacctaagc ccaaggatac ccttatgatt tctaggacac ctgaggtgac ctgcgtcgtt   240
```

```
gtggacgtga gtcaagagga cccagaggtc cagtttaact ggtatgttga cggcgtggaa    300
gtgcataatg caaaaactaa accccgcgag gaacaattca attcaaccta ccgggtcgtt    360
tctgtgttga cagtgctgca tcaagattgg ctgaacggga aggagtataa gtgtaaagtc    420
agtaataagg gactcccctc tagtatcgaa aaaactattt caaaggccaa aggccagcct    480
agagagccac aggtgtacac ccttcctcca tcccaagagg agatgacaaa gaaccaggtg    540
tctctgactt gtctcgtgaa ggggttctac cctagtgaca tcgctgtcga atgggagtca    600
aacggacagc cagagaataa ttataagaca actcctcccg ttctggattc tgacggcagc    660
ttctttctgt actctaggct tactgtggac aaaagtcgct ggcaagaagg gaacgtcttt    720
tcatgttctg ttatgcacga ggccttgcac aatcattata cacagaagtc tctgagtctc    780
tcactgggca aaggcggggg aggcagcggg ggaggcgggt ccggaggcgg gggatctcat    840
cccatccctg actccagtcc tctcctgcaa ttcggggggcc aagtccggca gcggtacctc    900
tacacagatg atgctcagca gacagaagcc cacctggaga tcagggagga tgggaccgtg    960
gggggcgctg ctgaccagag ccccgaaagt ctcctgcagc tgaaagcctt gaagcctgga   1020
gttattcaaa tcttgggagt caagactagt aggttcctgt gccagcggcc agatggggcc   1080
ctgtatggat ctctccattt tgaccctgag gcctgcagct ccgggagga gatcagaccc   1140 gacggataca atgtttacca gtccgaagcc cacggcctcc ctctgcatct gcccgggaac   1200
aagtctcctc accgggaccc tgcccccaga ggacctgctc gcttcctgcc actcccaggc   1260 ctgcccccg cattgcctga gccacccgga atcctggccc ccagccccc tgatgtggga   1320 tcctctgacc ctctgagcat ggtgaaccct tcccagggca gaagcccag ctacgagtcc   1380
```

<210> SEQ ID NO 81
<211> LENGTH: 4
<212> TYPE: PRT
<213> ORGANISM: Artificial Sequence
<220> FEATURE:
<223> OTHER INFORMATION: Position 98-101 of FGF21

<400> SEQUENCE: 81

Leu Leu Leu Glu
1

<210> SEQ ID NO 82
<211> LENGTH: 5
<212> TYPE: PRT
<213> ORGANISM: Artificial Sequence
<220> FEATURE:
<223> OTHER INFORMATION: Position 170-174 of FGF21

<400> SEQUENCE: 82

Gly Pro Ser Gln Gly
1               5

<210> SEQ ID NO 83
<211> LENGTH: 25
<212> TYPE: PRT
<213> ORGANISM: Artificial Sequence
<220> FEATURE:
<223> OTHER INFORMATION: Leader sequence

```
<400> SEQUENCE: 83

Met Asp Ala Met Leu Arg Gly Leu Cys Cys Val Leu Leu Leu Cys Gly
1               5                   10                  15

Ala Val Phe Val Ser Pro Ser His Ala
            20                  25
```